(12) United States Patent
Lizardi et al.

(10) Patent No.: US 11,046,999 B2
(45) Date of Patent: Jun. 29, 2021

(54) METHODS AND COMPOSITIONS FOR GENOMIC TARGET ENRICHMENT AND SELECTIVE DNA SEQUENCING

(71) Applicant: PetaOmics, Inc., San Antonio, TX (US)

(72) Inventors: Paul M. Lizardi, San Antonio, TX (US); Brent W. Ferguson, Cedar Creek, TX (US)

(73) Assignee: PetaOmics, Inc., San Marcos, TX (US)

( * ) Notice: Subject to any disclaimer, the term of this patent is extended or adjusted under 35 U.S.C. 154(b) by 625 days.

(21) Appl. No.: 15/268,403

(22) Filed: Sep. 16, 2016

(65) Prior Publication Data

US 2017/0073748 A1 Mar. 16, 2017

Related U.S. Application Data

(60) Provisional application No. 62/219,332, filed on Sep. 16, 2015.

(51) Int. Cl.
| | | |
|---|---|---|
| *C12Q 1/68* | (2018.01) | |
| *C12Q 1/6839* | (2018.01) | |
| *C12Q 1/6806* | (2018.01) | |

(52) U.S. Cl.
CPC ......... *C12Q 1/6839* (2013.01); *C12Q 1/6806* (2013.01)

(58) Field of Classification Search
CPC ............................ C12Q 1/6869; C12Q 1/6806
See application file for complete search history.

(56) References Cited

U.S. PATENT DOCUMENTS

| | | |
|---|---|---|
| 5,766,855 A | 6/1998 | Buchardt |
| 5,846,729 A | 12/1998 | Wu |
| 5,977,296 A | 11/1999 | Nielsen |
| 5,986,053 A | 11/1999 | Ecker |
| 6,063,569 A | 5/2000 | Gildea |
| 6,344,357 B1 | 2/2002 | Rickwood |
| 6,388,061 B1 | 5/2002 | Bergmann |
| 6,475,721 B2 | 11/2002 | Kleiber |
| 6,613,873 B1 | 9/2003 | Buchardt |
| 6,664,045 B1 * | 12/2003 | Hyldig-Nielsen ..... C07H 21/00 435/6.12 |
| 6,710,164 B1 | 3/2004 | Nielsen |
| 6,753,421 B2 | 6/2004 | Stender |
| 6,770,738 B1 | 8/2004 | Ecker |
| 6,777,544 B2 | 8/2004 | Uhlmann |
| 6,979,536 B1 | 12/2005 | Naesby |
| 7,105,294 B2 | 9/2006 | Dongen |
| 7,125,972 B2 | 10/2006 | Kleiber |
| 7,241,886 B2 | 7/2007 | Alexander |
| 7,368,245 B2 | 5/2008 | Dongen |
| 7,378,485 B2 | 5/2008 | Buchardt |
| 7,642,057 B2 | 1/2010 | Van Dongen |
| 7,855,054 B2 | 12/2010 | Schneider |
| 8,093,063 B2 | 1/2012 | Albitar |
| 8,753,821 B2 | 6/2014 | Hyldig-Nielsen |
| 8,912,312 B2 | 12/2014 | Hyldig-Nielsen |
| 2001/0010915 A1 | 8/2001 | Frank-Kamenetskii et al. |
| 2014/0128570 A1 | 5/2014 | Ly |

FOREIGN PATENT DOCUMENTS

WO 2013176992 11/2013

OTHER PUBLICATIONS

Bahal, et al., "D. Sequence-Unrestricted, Watson-Crick Recognition of Double Helical B-DNA by (R)-MiniPEG-gPNAs", Chem Bio Chem, 13:56-60 (2012).
Bahal, et al., "Nanoparticle for delivery of antisense ³PNA oligomers targeting CCR5", Artificial DNA PNA XNA, 4(2):49-57 (2013).
Bahal, et al., "Single-stranded ³PNAs for in vivo site-specific genome editing via Watson-Crick recognition",Curr Gene Ther. 14(5):331-42 (2014).
Brudno, et al., "An in vitro translation, selection and amplification system for peptide nucleic acids", Nat Chem Biol.,6(2):148-155 (2010).
Burgtorf, et al., "Clone-based systematic haplotyping (CSH): a procedure for physical haplotyping of whole genomes", Genome Res., 13(12):2717-24 (2003).
Buske, et al., "Triplex-Inspector: an analysis tool for triplex-mediated targeting of genomic loci", Bioinformatics, 29(15):1895-7 (2013).
Cantor, et al., "Sequence-specific manipulation of DNA", Genomics: The Science and Technology Behind the Human Genome Project. Publisher: Wiley-Interscience; 1 edition (Feb. 2, 1999).
Chung, et al., "Constructing Hepitypes: Phasing Local Genotype and DNA Methylation", J Neurosci Neuroengin, 2:1-12, 2013.
Clark, et al., "Enhanced 5-methylcytosine detection in single-molecule, real-time sequencing via Tet1 oxidation", BMC Biol.,11. 4. doi: 10.1186/1741-7007-11-4 (2013).

(Continued)

*Primary Examiner* — Jezia Riley
(74) *Attorney, Agent, or Firm* — PABST Patent Group LLP

(57) ABSTRACT

It has been established that one or more large double stranded DNA fragments (each 2,000 to 40,000 base pairs in size) can be captured and isolated from genomic DNA fragments using sequence specific PNA hybridization probes. Compositions and methods for enrichment of a multiplicity of long DNA sequences selected from the genome of any eukaryote are provided. Capture is performed using multiple PNA molecules with gamma-modified chiral backbones, comprising a mixture of neutral and positive chemical groups. Two or more PNA probes with covalently bound haptens, preferably biotin, target each DNA domain of interest for capture, isolation, and subsequent sequencing analysis of the multiplicity of enriched targets, including DNA methylation sequencing. The methods include enhancement of probe-DNA binding specificity through single strand binding proteins (SSB).

79 Claims, 5 Drawing Sheets

Specification includes a Sequence Listing.

(56) References Cited

OTHER PUBLICATIONS

De Costa, et al., "Differential DNA and RNA sequence discrimination by PNA having charged side chains", Bioorg Med Chem Lett., 24(10):2360-3 (2014).
De Costa, et al., "Evaluating the effect of ionic strength on duplex stability for PNA having negatively or positively charged side chains", PLoS One, 8(3):e58670 (2013).
Demidov, et al., "Duplex DNA capture", Curr Issues Mol Biol., 2(1):31-5 (2000).
Dragulescu-Andrasi, et al., "A simple gamma-backbone modification preorganizes peptide nucleic acid into a helical structure", J Am Chem Soc., 128(131):10258-67 (2006).
Dueholm, et al., "Peptide nucleic acid (PNA) with a chiral backbone based on alanine", Bioorg. Med. Chem. Lett., 4:1077-80 (1994).
Edgar, "Search and clustering orders of magnitude faster than BLAST", Bioinformatics. 26(19):2460-1 (2010).
Egholm, et al., "Peptide nucleic acids (PNA). Oligonucleotide analogues with an achiral peptide backbone", J. Am. Chem. Soc. 114:1895-7 (1992).
Englund and Appella, "Synthesis of $^3$-substituted peptide nucleic acids: A new place to attach fluorophores without affecting DNA binding", Org. Lett., 7(16):3465-7 (2005).
Gambari, "Peptide nucleic acids: a review on recent patents and technology transfer", Expert Opinion Ther. Pat., 24(3):267-94 (2014).
Gnirke, et al., "Solution hybrid selection with ultra-long oligonucleotides for massively parallel targeted sequencing", Nat Biotechnol. ,27(2):182-9 (2009).
Guo et al., "Direct fluorescence analysis of genetic polymorphisms by hybridization with oligonucleotide arrays on glass supports", Nucleic acids Res. 22:5456-65 (1994).
Guo, et al., "Single-cell methylome landscapes of mouse embryonic stem cells and early embryos analyzed using reduced representation bisulfite sequencing", Genome Res., 23(12):2126-35 (2013).
Hansen, et al., "High-affinity triplex targeting of double stranded DNA using chemically modified peptide nucleic acid oligomers", Nucleic acids Res., 37(13):4498-507 (2009).
Hasmats, et al., "Assessment of whole genome amplification for sequence capture and massively parallel sequencing", PLoS One, 9(1):e84785. doi: 10.1371 (2014).
He, et al., "Strand invasion of extended, mixed-sequence B-DNA by gammaPNAs", J Am Chem Soc., 131(34):12088-90 (2009).
He, et al., "The structure of a gamma-modified peptide nucleic acid duplex", Mol Biosyst., 6(9):1619-29 (2010).
Herrmann, et al., "Pipeline for large-scale microdroplet bisulfite PCR-based sequencing allows the tracking of hepitype evolution in tumors", PLoS One., 6(7):e21332 (2011).
Hodges, et al., "Genome-wide in situ exon capture for selective re-sequencing", Nat Genet., 39(12):1522-7 (2007).
Hodges, et al., "Hybrid selection of discrete genomic intervals on custom-designed microarrays for massively parallel sequencing", Nat Protoc., 2009;4(6):960-74 (2009).
Huang, et al., "Preparation and Determination of Optical Purity of $^3$-Lysine Modified Peptide nucleic acid Analogues", Arch Pharm Res., 35(3):517-22 (2012).
International Search Report for corresponding PCT application PCT/US2016/052317 dated Dec. 14, 2016.
Ishizuka, et al., "Chiral introduction of positive charges to PNA for double-duplex invasion to versatile sequences", Nucleic acids Res., 36(5):1464-71 (2008).
Ishizuka, et al., "SSB-assisted duplex invasion of preorganized PNA into double-stranded DNA", Chembiochem., 10(16):2607-12 (2009a).
Ishizuka, et al., "Strand invasion of conventional PNA to arbitrary sequence in DNA assisted by single-stranded DNA binding protein", Chem Commun (Camb)., 14; (10):1225-7 (2009b).
Ito, et al., "Sequence-specific DNA purification by triplex affinity capture", PNAS, 89(2):495-8 (1992a).
Ito, et al., "Triplex affinity capture of a single copy clone from a yeast genomic library", Nucleic acids Res., 20(13):3524 (1992b).
Khrapko, et al., "Hybridization of DNA with oligonucleotides immobilized in a gel: a convenient method for recording single base replacements", Mol Biol (Mosk) (USSR) 25:718-730 (1991) Abstract Only.
Kuhn, et al., "Sequence specificity at targeting double-stranded DNA with a $^3$-PNa oligomer modified with guanidinium G-clamp nucleobases", Artif DNA PNA XNA.,1(1):45-53 (2010).
Kuleshov, et al., "Wholoe-genome haplotyping using ong reads and statistical methods", Nat. Biotechnology, doi:10.1038/nbt.2833 (2014).
Letsinger, et al., "Cholesteryl-conjugated oligonucleotides: synthesis, properties, and activity as inhibitors of replication of human immunodeficiency virus in cell culture", PNAS, 86:6553 6 (1989).
Lohse, et al., "Double duplex invasion by peptide nucleic acid: a general principle for sequence-specific targeting of double-stranded DNA", PNAS, 96(21):11804-8 (1999).
Lonkar, et al., "Targeted correction of a thalassemia-associated beta-globin mutation induced by pseudo-complementary peptide nucleic acids", Nucleic acids Res., 37(11):3635-44 (2009).
Mikhailov, et al., "Affinity capture of specific DNA fragments with short synthetic sequences", Ru J Bioorganic Chem., 39(1):72-6 (2013).
Murphy, et al., "Human leukocyte antigen haplotype phasing by allele-specific enrichment with peptide nucleic acid probes", Moler Genet Genomic Med., 2(3):245-53 (2014).
Nielsen, et al., "An introduction to peptide nucleic acid", Curr Iss Mole Biol., 1(1-2):89-104 (1999).
Nielsen, et al., "Sequence selective recognition of DNA by strand displacement with a thymine substituted polyamide", Science, 254:1497-1500 (1991).
Orum, "Purification of nucleic acids by hybridization to affinity tagged PNA probes", Curr Issues Mol Biol., 1(1-2):105-10 (1999).
Panyutin, et al., "Targeting linear duplex DNA with mixed-base peptide nucleic acid oligomers facilitated by bisPNA openers", Analy Biochem., 362:145-7 (2007).
Pasquali, et al., "Pancreatic islet enhancer clusters enriched in type 2 diabetes risk-associated variants", Nat Genet.,46(2):136-43 (2014).
Pease, et al., "Light-generated oligonucleotide arrays for rapid DNA sequence analysis", PNAS, 91(11):5022-6 (1994).
Pham, et al., "Single-locus enrichment without amplification for sequencing and direct detection of epigenetic modifications", Mol Genet Genomics, 291:1491-1504 (2016).
Ray and Norden, "Peptide nucleic acid (PNA): its medical and biotechnical applications and promise for the future", FASEB J., 14(9):1041-60 (2000).
Sahu, et al., "Synthesis and characterization of conformationally preorganized, (R)-diethylene glycol-containing $^3$-peptide nucleic acids with superior hybridization properties and water solubility", J Org Chem., 76(14):5614-27 (2011).
Santa Lucia, "A unified view of polymer, dumbbell, and oligonucleotide DNA nearest-neighbor thermodynamics", PNAS, 95(4):1460-5 (1998).
Schleifman, et al., "Peptide nucleic acid-mediated recombination for targeted genomic repair and modification", Methods Mol Biol., 1050:207-22 (2014).
Schleifman, et al., "Site-specific Genome Editing in PBMCs With PLGA Nanoparticle-delivered PNAs Confers HIV-1 Resistance in Humanized Mice", Mol Ther Nucleic Acids.,2:e135. doi: 10.1038/mtna (2013).
Shigi, et al., "Affinity isolation of desired restriction fragment from human genome using double-duplex invasion of biotin-bound pseudo-complementary PNA", Chem Soc Japan, 44:1569-71 plus supporting information (2015).
Smulevitch, et al., "Enhancement of strand invasiom by oligonucleotides through manipulation of backbone charge", Nature Biotech., 14:1700-4 (1996).
Stimpson, et al., "Real-time detection of DNA hybridization and melting on oligonucleotide arrays by using optical wave guid", PNAS, 92:6379-83 (1995).
Sugiyama and Kittaka, "Chiral peptide nucleic acids with a substituent in the N-(2-aminoethy)glycine backbone", Molecules.,18(1):287-310 (2013).
Syvanen, et al., "Fast quantification of nucleic acid hybrids by affinity-based hybrid collection", Nucleic acids Res., 14:5037 (1986).

(56) References Cited

OTHER PUBLICATIONS

Tanaka, et al., "Ribonuclease A as effective promoter for unimolecular invasion of peptide nucleic acid to double-stranded DNA", Chem Soc of Japan, 45:767-9 (2016).
Tedeschi, et al., "Synthesis of new chiral PNAs bearing a dipeptide-mimic monomer with two lysine-derived stereogenic centres", Tetrahedron Lett., 46:8395-9 (2005).
Tewhey, et al., "Enrichment of sequencing targets from the human genome by solution hybridization", Genome Biol.,10(10):R116. (2009).
Tilani, et al., "Differential DNA and RNA sequence discrimination by PNA having charged side chains", Bioorganic & Medicinal Chemistry Lett., 24:2360-3 (2014).
Totsingan, et al., "Helix control in polymers: case of peptide nucleic acids (PNAs)", Artif DNA PNA XNA, 3(2):31-44 (2012).
Wang, et al., "PacBio-LITS: a large-insert targeted sequencing method for characterization of human disease-associated chromosomal structural variations", BMC Genomics.,16(1):214 (2015).
Yeh, et al., "Crystal structure of chiral $^3$PNA with complementary DNA strand: Insights into the stability and specificity of recognition and conformational preorganization", J. Am. Chem. Soc., 132:10717-27 (2010).

\* cited by examiner

FIGS. 1A-D

METHODS AND COMPOSITIONS FOR GENOMIC TARGET ENRICHMENT AND SELECTIVE DNA SEQUENCING

CROSS-REFERENCE TO RELATED APPLICATIONS

This application claims priority to U.S. Ser. No. 62/219,332, filed on Sep. 16, 2015, which where permissible is incorporated by reference in its entirety.

REFERENCE TO SEQUENCE LISTING

The Sequence Listing submitted Sep. 16, 2016 as a text file named "PETOM_100_ST25.txt," created on Sep. 14, 2016, and having a size of 7,047 bytes is hereby incorporated by reference pursuant to 37 C.F.R. § 1.52(e)(5).

FIELD OF THE INVENTION

The disclosed invention is generally related to methods for sequence-specific capture of fragments of double-stranded DNA from a mixture or library of fragments, specifically for preserving the native quantity, structure, methylation status, or a combination thereof, of genomic DNA molecules greater than 2 kilobases in length.

BACKGROUND OF THE INVENTION

Using thousands of distinct DNA probes bound to the surface of microarrays, it was possible to isolate most of the exon sequences of the human genome (Hodges et al., 2007), as well as thousands of specific genomic intervals of biological interest (Hodges et al., 2009). More recently, there has been increased interest in isolating and sequencing long DNA reads to enable construction of phased haplotypes, which consist of sequence assemblies corresponding to a single pure paternal or maternal DNA strand. A phased haplotype will contain an ordered set of single nucleotide polymorphisms (SNPs) that contain valuable genetic information about the genetic linkage structure of genetically determined variability over long distances in the human genome.

A large amount of literature summarizes recent advances in sequence-specific DNA capture and genomic sequencing methods (Tewhey, et al., Genome Biology, 10:R116 (2009); Wang, et al. BMC Genomics 16:214, (2015); Orum, Current Issues Molec. Biol. 1(2): 105-110 (1999)). The most widely used technology for genomic sequence capture is solution DNA capture, using either DNA or RNA probes complementary to genomic regions of interest (Gnirke et al., 2009, Tewhey et al., 2009). However, DNA capture is difficult to achieve when target molecules consist of long, single stranded DNA which rapidly undergo intermolecular re-association via hybridization of mutually complementary, repetitive sequences that are ubiquitous in almost all eukaryotic genomes. Through this re-association process, partially double-stranded complexes are rapidly formed that bring together many unrelated genomic domains via interaction with multiple repetitive DNA segments present in the vast majority of long DNA molecules. These multiple events of inter-molecular re-association lead to the formation of DNA polymer networks that make it difficult to isolate specific DNA target sequences from long, single stranded DNA.

Alternative methods aimed at selectively enriching long genomic DNA domains consist of molecular cloning using fosmid vectors (Burgtorf et al., 2003). However, fosmid cloning is time consuming and has the disadvantage of eliminating DNA methylation information present in the DNA of the cells of interest.

Sequence capture of long DNA, followed by DNA sequencing has also been reported by PACIFIC BIOSCIENCES® and Nimblegen (subsidiary of Roche, Inc.) in a collaborative effort with an academic group (Wang, et al., 2015). The final product, a large insert capture library with PacBio SMRT bell adaptors ligated to both ends of the inserts, is loaded onto the PacBio platform for long read-length sequencing. However, this method is time-consuming and utilizes ligation-mediated (LM) PCR, resulting in potential imbalances in the ratio of maternal and paternal alleles in the final DNA library.

The most efficient method yet reported for the construction of whole-genome phased haplotypes is Statistically Aided Long Read Haplotyping (SLRH, Kuleshov, et al., 2014). Using SLRH, Kuleshov et al. (2014) demonstrated the phasing of 99% of single-nucleotide variants in three human genomes into long haplotype blocks 0.2-1 Mbp in length. However, genome-wide association studies, which are based on the underlying principle of linkage disequilibrium (LD) in which a disease predisposing allele co-segregates with a particular allele of a SNP, have been hampered by the lack of whole-genome genotyping methodologies.

Just like SNPs can be ordered by phasing of long DNA sequencing reads, it is possible, in theory, to assemble phased "hepitypes," containing an ordered set of positions of variable cytosine methylation status (i.e., methylated or unmethylated) that contains valuable epigenetic information about the epigenetic linkage structure of epigenetically determined variability, over relatively long distances in the human genome. However, DNA methylation sequencing technologies yield sequencing reads no longer than 250 bases, which are unsuitable for construction of phased haplotypes.

Thus, there remains a lack of suitable methods for isolating and sequencing large double-stranded DNA fragments for the construction of phased haplotypes that preserve the cytosine methylation status of the organism (Guo, et al., Genome Res., 23(12):2126-35 (2013)).

Accordingly, improved methods for sequence-specific capture and sequencing of long double-stranded genomic DNA fragments are needed.

Therefore, it is an object of the invention to provide sensitive and/or efficient methods for enrichment of one or more long DNA sequence domains (greater than 2,000 bases in size) selected from the genome of eukaryotic cells.

It is also an object of the invention to provide sensitive and efficient methods for enrichment of a large multiplicity of long DNA sequence domains (each 2,000 to 40,000 bases in size) selected from the genome of eukaryotic cells.

It is also an object of the invention to provide methods for genomic target enrichment to generate DNA fragments that preserve mutations, insertions, deletions, methylation status, or a combination thereof, of long DNA sequences.

It is also an object of the invention to provide methods for sequencing of DNA obtained by genomic target enrichment that yields long DNA fragments, whereby the DNA sequencing data contains information that enables identification of short insertions and short deletions that are very difficult to identify when DNA is enriched by conventional methods that yield short DNA fragments.

It is also an object of the invention to provide methods for sequencing of DNA obtained by genomic target enrichment that yields long DNA fragments, whereby the DNA sequencing data contains base modification information that enables identification of long patterns of variation in long DNA methylation patterns among different samples, said variation in patterns of DNA methylation being impossible to identify when DNA is enriched by conventional methods that yield short DNA fragments.

It is also an object of the invention to provide methods for isolating, accessing, and processing large genomic DNA fragments that enable the phasing of DNA methylation reads across large target sequence domains.

It is also an object of the invention to provide methods for isolating, accessing, and processing large genomic DNA fragments that enable the phasing of DNA methylation reads across large paternal or maternal sequence domains.

It is also an object of the invention to provide methods for isolating, accessing, and processing large genomic DNA fragments that enable the phasing of DNA methylation reads in the range of 60,000 to 1,000,000 bases.

It is also an object of the invention to provide methods to rapidly screen probes to identify probes of high specificity for improved sequence-specific enrichment.

It is also an object of the invention to provide methods to rapidly screen probes that perform with poor specificity and to replace these with probes of higher specificity for improved sequence-specific enrichment.

BRIEF SUMMARY OF THE INVENTION

Disclosed are methods and compositions for selectively enriching one or more nucleic acid fragments from a mixture of nucleic acid fragments. Some forms of the disclosed methods and compositions are particularly useful for selectively enriching large genomic DNA fragments. Doing so enables linkage analysis of DNA modifications, such as methylation patterns, that are difficult to perform in other ways.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to their target sequence in a nucleic acid fragment, thereby forming nucleic acid fragments bound by PNA probes; (c) capturing the nucleic acid fragments bound by PNA probes via the capture tag and removing the uncaptured components of the reaction mix from the captured nucleic acid fragments bound by PNA probes; and (d) eluting the captured nucleic acid fragments from the PNA probes to form an enriched nucleic acid sample. This form of the method can thus result in nucleic acid fragments targeted by the PNA probes being enriched in the enriched nucleic acid sample as compared to the first nucleic acid sample. In this form of the method, the PNA probes in the same set of two or more PNA probes are designed to target a different sequence in the same nucleic acid fragment, the PNA probes in different sets of two or more PNA probes are designed to target different nucleic acid fragments, and the PNA probes each include one or more capture tags. In some forms, the step of capturing the nucleic acid fragments bound by PNA probes via the capture tag also captures the unbound PNA probes. In some forms, the method can also include, following step (b) and prior to step (c), removing unbound PNA probes from the reaction mix. In some forms, the method can also include, simultaneous with capturing the nucleic acid fragments bound by PNA probes, capturing unbound PNA probes via the capture tag.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to their target sequence in a nucleic acid fragment, thereby forming nucleic acid fragments bound by PNA probes; (c) removing unbound PNA probes from the reaction mix; (d) capturing the nucleic acid fragments bound by PNA probes via the capture tag and removing the uncaptured components of the reaction mix from the captured nucleic acid fragments bound by PNA probes; and (e) eluting the captured nucleic acid fragments from the PNA probes to form an enriched nucleic acid sample. This form of the method can thus result in nucleic acid fragments targeted by the PNA probes being enriched in the enriched nucleic acid sample as compared to the first nucleic acid sample. In this form of the method, the PNA probes in the same set of two or more PNA probes are designed to target a different sequence in the same nucleic acid fragment, the PNA probes in different sets of two or more PNA probes are designed to target different nucleic acid fragments, and the PNA probes each include one or more capture tags.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to their target sequence in a nucleic acid fragment, thereby forming nucleic acid fragments bound by PNA probes; (c) capturing both the nucleic acid fragments bound by PNA probes via the capture tag and the unbound PNA probes via the capture tag and removing the uncaptured components of the reaction mix from the captured nucleic acid fragments bound by PNA probes; and (d) eluting the captured nucleic acid fragments from the PNA probes to form an enriched nucleic acid sample. In these forms, the unbound PNA probes are separated from the nucleic acid fragments bound by PNA probes by elution of the captured nucleic acid fragments but not the captured unbound PNA probes. The unbound PNA probes remain captured when the captured nucleic acid fragments are eluted.

In some forms of the method, the PNA probes each include one or more capture tags, where at least one of the PNA probes includes one or more peptide nucleic acid residues that are derivatized with a charged moiety on the alpha carbon, beta carbon, gamma carbon, or combinations thereof and one or more peptide nucleic acid residues that are derivatized with a neutral moiety on the alpha carbon, beta carbon, gamma carbon, or combinations thereof.

In some forms of the method, the PNA probes in at least one of the sets of two or more PNA probes has 18 or 19 peptide nucleic acid residues, where at or between three to five of the peptide nucleic acid residues of the PNA probes in the at least one of the sets of two or more PNA probes are derivatized with the charged moieties, where the charged moieties are selected from the group consisting of gamma-L-lysine PNA, gamma-L-thialysine PNA, and combinations thereof, where at or between two to six of the peptide nucleic acid residues of the PNA probes in the at least one of the sets of two or more PNA probes that are not derivatized with the charged moieties are derivatized with diethylene glycol, and where the capture tag of the PNA probes in at least one of the sets of two or more PNA probes is biotin.

In some forms of the method, in one or more of the PNA probes there are independently at or between one to three peptide nucleic acid residues that are not derivatized with a charged moiety between every peptide nucleic acid residue that is derivatized with a charged moiety. In some forms of the method, in all of the PNA probes there are independently at or between one to three peptide nucleic acid residues that are not derivatized with a charged moiety between every peptide nucleic acid residue that is derivatized with a charged moiety. In some forms of the method, in one or more of the PNA probes there is an average of at or between 1.0 to 5.0 peptide nucleic acid residues that are not derivatized with a charged moiety between every peptide nucleic acid residue that is derivatized with a charged moiety. In some forms of the method, in all of the PNA probes there is an average of at or between 1.0 to 5.0 peptide nucleic acid residues that are not derivatized with a charged moiety between every peptide nucleic acid residue that is derivatized with a charged moiety.

In some forms of the method, in one or more of the PNA probes there are independently at or between zero to two peptide nucleic acid residues that are not derivatized with a moiety between every peptide nucleic acid residue that is derivatized with a moiety. In some forms of the method, in all of the PNA probes there are independently at or between zero to two peptide nucleic acid residues that are not derivatized with a moiety between every peptide nucleic acid residue that is derivatized with a moiety. In some forms of the method, in one or more of the PNA probes there is an average of at or between 0.5 to 1.5 peptide nucleic acid residues that are not derivatized with a moiety between every peptide nucleic acid residue that is derivatized with a moiety. In some forms of the method, in all of the PNA probes there is an average of at or between 0.5 to 1.5 peptide nucleic acid residues that are not derivatized with a moiety between every peptide nucleic acid residue that is derivatized with a moiety.

In some forms, at least one of the PNA probes includes (a) one or more peptide nucleic acid residues that are derivatized with a charged moiety on the alpha carbon, beta carbon, gamma carbon, or combinations thereof, (b) one or more peptide nucleic acid residues that are derivatized with a neutral moiety on the alpha carbon, beta carbon, gamma carbon, or combinations thereof, or (c) combinations thereof. In some forms, the reaction mix can further include a single-strand binding protein. In some forms, the first nucleic acid sample has high sequence complexity. In some forms, the first nucleic acid sample includes double stranded DNA. In some forms, the first nucleic acid sample includes genomic DNA.

In some forms, the enriched nucleic acid fragments have an average length of at least 2,000 base pairs. In some forms, the enriched nucleic acid fragments have an average length of at least 10,000 base pairs. In some forms, the enriched nucleic acid fragments have an average length of at least 15,000 base pairs. In some forms, each of the enriched nucleic acid fragments has a length of at least 2,000 base pairs. In some forms, each of the enriched nucleic acid fragments has a length of at least 10,000 base pairs. In some forms, each of the enriched nucleic acid fragments has a length of at least 15,000 base pairs. In some forms, the nucleic acid fragments targeted by the PNA probes are enriched to constitute at least 90% of the enriched nucleic acid sample.

Also disclosed are peptide nucleic acid (PNA) hybridization probes. In some forms, the PNA probe is designed to target a sequence in a nucleic acid fragment. In some forms, the PNA probe includes one or more capture tags. In some forms, the PNA probe is designed to target a sequence in a nucleic acid fragment. In some forms, the PNA probe includes (a) one or more peptide nucleic acid residues that are derivatized with a charged moiety on the alpha carbon, beta carbon, gamma carbon, or combinations thereof, (b) one or more peptide nucleic acid residues that are derivatized with a neutral moiety on the alpha carbon, beta carbon, gamma carbon, or combinations thereof, or (c) combinations thereof.

In some forms, the PNA probe includes two to six peptide nucleic acid residues that independently are derivatized with a charged moiety on the alpha, beta, or gamma carbon. In some forms, one or more of the peptide nucleic acid residues that are derivatized with the charged moiety are derivatized with the charged moiety on the gamma carbon. In some forms, all of the peptide nucleic acid residues that are derivatized with the charged moiety are derivatized with the charged moiety on the gamma carbon. In some forms, one or more of the charged moieties are lysine. In some forms, all of the charged moieties are lysine. In some forms, one or more of the charged moieties are L-lysine. In some forms, all of the charged moieties are L-lysine.

In some forms, the PNA probe includes one or more peptide nucleic acid residues that are derivatized with a short-chain oligoethylene moiety on the alpha, beta, or gamma carbon. In some forms, the PNA probe includes one to nineteen peptide nucleic acid residues that independently are derivatized with the short-chain oligoethylene moiety on the alpha, beta, or gamma carbon. In some forms, one or more of the peptide nucleic acid residues that are derivatized with the short-chain oligoethylene moiety are derivatized with the short-chain oligoethylene moiety on the gamma carbon. In some forms, all of the peptide nucleic acid residues that are derivatized with the short-chain oligoethylene moiety are derivatized with the short-chain oligoethylene moiety on the gamma carbon. In some forms, one or more of the short-chain oligoethylene moieties are diethylene glycol. In some forms, all of the short-chain oligoethylene moieties are diethylene glycol.

In some forms, the capture tag is biotin or streptavidin. In some forms, the PNA probe is derivatized with one or more charged moieties on at least one of the terminal PNA residues. In some forms, the charged moiety derivatizing the terminal PNA probe is one or more amino acids. In some forms, the charged moiety derivatizing the terminal PNA probe is two or more lysine residues.

Also disclosed are sets of peptide nucleic acid (PNA) hybridization probes. In some forms, a set includes two or more PNA probes, where each of the PNA probes in the set are designed to target a different sequence in the same nucleic acid fragment. In some forms, multiples of these sets are used. In some forms, the PNA probes in different sets of two or more PNA probes are designed to target different nucleic acid fragments. In some forms, one or more of the PNA probes in a set includes one or more capture tags. In some forms, each of the PNA probes in a set includes one or more capture tags. In some forms, one or more of the PNA probes includes (a) one or more peptide nucleic acid residues that are derivatized with a charged moiety on the alpha carbon, beta carbon, gamma carbon, or combinations thereof, (b) one or more peptide nucleic acid residues that are derivatized with a neutral moiety on the alpha carbon, beta carbon, gamma carbon, or combinations thereof, or (c) combinations thereof. In some forms, each of the PNA probes in a set includes (a) one or more peptide nucleic acid residues that are derivatized with a charged moiety on the alpha carbon, beta carbon, gamma carbon, or combinations thereof, (b) one or more peptide nucleic acid residues that are derivatized with a neutral moiety on the alpha carbon, beta carbon, gamma carbon, or combinations thereof, or (c) combinations thereof. In some forms, all of the PNA probes include (a) one or more peptide nucleic acid residues that are derivatized with a charged moiety on the alpha carbon, beta carbon, gamma carbon, or combinations thereof, (b) one or more peptide nucleic acid residues that are derivatized with a neutral moiety on the alpha carbon, beta carbon, gamma carbon, or combinations thereof, or (c) combinations thereof.

In some forms, one or more of the PNA probes independently include two to six peptide nucleic acid residues that independently are derivatized with the charged moiety on the alpha, beta, or gamma carbon. In some forms, all of the PNA probes independently include two to six peptide nucleic acid residues that independently are derivatized with the charged moiety on the alpha, beta, or gamma carbon. In some forms, independently in one or more of the PNA probes one or more of the peptide nucleic acid residues that are derivatized with the charged moiety are derivatized with the charged moiety on the gamma carbon. In some forms, in one or more of the PNA probes all of the peptide nucleic acid residues that are derivatized with the charged moiety are derivatized with the charged moiety on the gamma carbon. In some forms, in all of the PNA probes one or more of the peptide nucleic acid residues that are derivatized with the charged moiety are derivatized with the charged moiety on the gamma carbon. In some forms, in all of the PNA probes all of the peptide nucleic acid residues that are derivatized with the charged moiety are derivatized with the charged moiety on the gamma carbon.

In some forms of the probe, the PNA probe has at or between 10 to 26 peptide nucleic acid residues. In some forms of the probe, the PNA probe is designed to target a sequence in a nucleic acid fragment. In some forms of the probe, the PNA probe includes one or more peptide nucleic acid residues that are derivatized with a charged moiety on the alpha, beta, or gamma carbon or combinations thereof, and one or more peptide nucleic acid residues that are derivatized with or a neutral moiety on the alpha, beta, or gamma carbon, or combinations thereof. In some forms of the probe, the PNA probe includes one or more capture tags.

In some forms of the probe, the probe includes at or between 16 to 22 peptide nucleic acid residues. In some forms of the probe, the probe includes 18 or 19 peptide nucleic acid residues. In some forms of the probe, at or between three to five of the peptide nucleic acid residues are derivatized with the charged moieties, where the charged moieties are selected from the group consisting of gamma-L-lysine PNA, gamma-L-thialysine PNA, and combinations thereof, where at or between two to six of the peptide nucleic acid residues that are not derivatized with the charged moieties are derivatized with diethylene glycol, and where the capture tag is biotin. In some forms of the probe, four of the peptide nucleic acid residues are gamma-L-lysine PNA, where four of the peptide nucleic acid residues that are derivatized with diethylene glycol, and where the capture tag is biotin. In some forms of the probe, four of the peptide nucleic acid residues are gamma-L-thialysine PNA, where four of the peptide nucleic acid residues that are derivatized with diethylene glycol, and where the capture tag is biotin.

In some forms of the probe, independently at or between one to three peptide nucleic acid residues that are not derivatized with a charged moiety between every peptide nucleic acid residue that is derivatized with a charged moiety. In some forms of the probe, there is an average of at or between 1.0 to 5.0 peptide nucleic acid residues that are not derivatized with a charged moiety between every peptide nucleic acid residue that is derivatized with a charged moiety. In some forms of the probe, there are independently at or between zero to two peptide nucleic acid residues that are not derivatized with a moiety between every peptide nucleic acid residue that is derivatized with a moiety. In some forms of the probe, there is an average of at or between 0.5 to 1.5 peptide nucleic acid residues that are not derivatized with a moiety between every peptide nucleic acid residue that is derivatized with a moiety. In some forms of the probe, every peptide nucleic acid residue is derivatized with a moiety.

In some forms, one or more of the charged moieties are lysine. In some forms, all of the charged moieties are lysine. In some forms, one or more of the charged moieties are L-lysine. In some forms, all of the charged moieties are L-lysine.

In some forms, one or more of the PNA probes independently include one or more peptide nucleic acid residues that are derivatized with a short-chain oligoethylene moiety on the alpha, beta, or gamma carbon. In some forms, one or more of the PNA probes independently include one to nineteen peptide nucleic acid residues that independently are derivatized with the short-chain oligoethylene moiety on the alpha, beta, or gamma carbon. In some forms, all of the PNA probes independently include one to nineteen peptide nucleic acid residues that independently are derivatized with the short-chain oligoethylene moiety on the alpha, beta, or gamma carbon. In some forms, independently in one or more of the PNA probes one or more of the peptide nucleic acid residues that are derivatized with the short-chain oligoethylene moiety are derivatized with the short-chain oligoethylene moiety on the gamma carbon. In some forms, in one or more of the PNA probes all of the peptide nucleic acid residues that are derivatized with the short-chain oligoethylene moiety are derivatized with the short-chain oligoethylene moiety on the gamma carbon. In some forms, in all of the PNA probes one or more of the peptide nucleic acid residues that are derivatized with the short-chain oligoethylene moiety are derivatized with the short-chain oligoethylene moiety on the gamma carbon. In some forms, in all of the PNA probes all of the peptide nucleic acid residues that are derivatized with the short-chain oligoethylene moiety are derivatized with the short-chain oligoethylene moiety on the gamma carbon. In some forms, one or more of the short-chain oligoethylene moieties are diethylene glycol. In some forms, all of the short-chain oligoethylene moieties are diethylene glycol.

In some forms, one or more of the PNA probes can independently include one or more peptide nucleic acid residues having a pseudo-complementary nucleobase as the base moiety of the peptide nucleic acid residue. In some forms, one or more of the PNA probes can independently include one to twenty-two peptide nucleic acid residues having a pseudo-complementary nucleobase as the base moiety of the peptide nucleic acid residue. In some forms, all of the PNA probes can independently include one to twenty-two peptide nucleic acid residues having a pseudo-complementary nucleobase as the base moiety of the peptide nucleic acid residue.

In some forms, the pseudo-complementary nucleobases are independently selected from the group consisting of pseudouridine (5-ribosyluracil); 7-Deaza-2'-deoxyguanosine; 2,6-Diaminopurine-2'-deoxyriboside; N4-Ethyl-2'-deoxycytidine; 2-thiothymidine; 2-aminoadenine; 2-aminopurine-riboside; 2,6-diaminopurine-riboside; 2'-deoxyisoguanosine; and 5-hydroxymethyl-2'-deoxycytidine.

In some forms, the one or more of the PNA probes that include one or more peptide nucleic acid residues having a pseudo-complementary nucleobase as the base moiety of the peptide nucleic acid residue is a subset of the PNA probes in the one or more sets of PNA probes. In some forms, the subset of the PNA probes in the one or more sets of PNA probes includes a subset of the PNA probes in the one or more sets of PNA probes that are predicted to be capable of interacting with one or more of the other PNA probes in the one or more sets of PNA probes. In some forms, the subset of the PNA probes in the one or more sets of PNA probes is a subset of the PNA probes in the one or more sets of PNA probes that are predicted to be capable of interacting with one or more of the other PNA probes in the one or more sets of PNA probes.

In some forms, the capture tag is biotin or streptavidin. In some forms, one or more of the PNA probes are derivatized with one or more amino acids on at least one of the terminal PNA residues. In some forms, one or more of the PNA probes are derivatized with two or more lysine residues on at least one of the terminal PNA residues.

In some forms, the method can also include amplifying one or more of the nucleic acid fragments in the enriched nucleic acid sample. In some forms, substantially all of the nucleic acid fragments in the enriched nucleic acid sample are amplified. In some forms, the nucleic acid fragments are amplified by whole genome amplification.

Methods for the sequence-specific capture of long nucleic acid sequences (i.e., between 2,000 and 40,000 base pairs in length, or more than 40,000 base pairs in length) have been developed using multiple PNA molecules with modified backbones. Such modifications can include a mixture of neutral and positive chemical groups. Particularly PNA molecules have gamma-modified chiral backbones that include a mixture of neutral and positive chemical groups. Some forms of PNA molecule have alpha-modified chiral backbones that include a mixture of neutral and positive chemical groups.

Two or more PNA probes with covalently bound haptens are used to target each nucleic acid of interest for capture, isolation, and subsequent sequencing analysis of all the targets enriched by sequence capture, including DNA methylation sequencing. Single-strand binding proteins (SSB) can be employed to enhance binding specificity. These principles have been utilized to develop a number of methods useful for enrichment of a multiplicity of genomic DNA regions by capturing very long (2-40 kb) double-stranded DNA molecules.

Methods of selectively enriching nucleic acids from a nucleic acid sample include the steps of (a) bringing into contact one or more sets of two or more peptide nucleic acid (PNA) probes with a first nucleic acid sample to form a reaction mix; (b) incubating the reaction mix under conditions that allow target-specific strand invasion binding by the PNA probes to a target sequence in a nucleic acid, thereby forming nucleic acid bound by PNA probes; (c) capturing the nucleic acid bound by PNA probes via a capture tag and removing the uncaptured components of the reaction mix from the captured nucleic acid bound by PNA probes; and (d) eluting the captured nucleic acids from the PNA probes to form an enriched nucleic acid sample. In some forms, the nucleic acid sample includes a multiplicity of complex nucleic acid sequences, such as nuclear DNA and mitochondrial DNA. In some forms, the step of capturing the nucleic acids bound by PNA probes via the capture tag also captures the unbound PNA probes. For such forms the capture medium preferably includes enough capturing components (such as capture docks) to capture all of the PNA probes, both bound and unbound.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to their target sequence in a nucleic acid, thereby forming nucleic acids bound by PNA probes; (c) removing unbound PNA probes from the reaction mix; (d) capturing the nucleic acids bound by PNA probes via the capture tag and removing the uncaptured components of the reaction mix from the captured nucleic acids bound by PNA probes; and (e) eluting the captured nucleic acids from the PNA probes to form an enriched nucleic acid sample. This form of the method can thus result in nucleic acids targeted by the PNA probes being enriched in the enriched nucleic acid sample as compared to the first nucleic acid sample.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to a target sequence in a nucleic acid, thereby forming nucleic acid bound by PNA probes; (c) capturing both the nucleic acid bound by PNA probes via the capture tag and unbound PNA probes via the capture tag and removing the uncaptured components of the reaction mix from the captured nucleic acids bound by PNA probes; and (d) eluting the captured nucleic acids from the PNA probes to form an enriched nucleic acid sample. In these forms, the unbound PNA probes are separated from the nucleic acids bound by PNA probes by elution of the captured nucleic acids but not the captured unbound PNA probes. The unbound PNA probes remain captured when the captured nucleic acids are eluted.

Therefore, the methods include selectively enriching large genomic DNA fragments from a genomic DNA sample. In some forms, the genomic DNA fragment is a large, double-stranded genomic DNA fragment of between 2,000 and 40,000 base pairs in length.

In an exemplary method, the invasion-capture reaction is incubated for up to 16 hours and the reaction mixture is then passed through a purification matrix twice in succession to remove approximately 99.75%, or more than 99.75% of the unbound biotinylated probes. Eluted material can be recovered and mixed with an affinity tag-specific capture dock immobilized onto a matrix such as Streptavidin-coated paramagnetic beads. Preferably the final concentration of unbound (free) biotinylated PNA probes in the reaction is less than 0.5 µM. Paramagnetic beads capable of binding a maximum of 1.5 µM biotin can be used. Typically, the DNA fragments targeted by the PNA probes are enriched in the enriched DNA sample as compared to the first DNA sample.

In some forms, the PNA probes in the same set of two or more PNA probes are designed to target a different sequence in the same DNA fragment. The PNA probes in different sets of two or more PNA probes can be designed to target different DNA fragments. In some forms the PNA probes each include one or more peptide nucleic acid residues derivatized with a charged moiety. The charged moiety can be on the alpha, beta, or gamma carbon. In some forms the PNA probes each include one or more capture tags.

Typically, the first DNA sample has high sequence complexity, for example, a genomic DNA sample. The enriched DNA fragments can have an average length of at least 2,000 base pairs, an average length of at least 10,000 base pairs, an average length of at least 15,000 base pairs, or an average length of more than 40,000 base pairs. Each of the enriched DNA sequences can have a length of at least 2,000 base pairs, a length of at least 10,000 base pairs, a length of at least 15,000 base pairs or a length of more than 40,000 base pairs. In some forms, the first and enriched nucleic acid samples include intact double-stranded nucleic acid fragments, such as nucleic acid that is not fully denatured or substantially denatured. The methods do not require denaturation of the target DNA. Therefore, in some forms, when the first nucleic acid sample includes target nucleic acid that is intact double-stranded nucleic acid that is never fully denatured or never substantially denatured, the enriched sample will also include intact double-stranded nucleic acid that is never fully denatured or never substantially denatured.

In some forms, one or more of the PNA probes independently include two to six peptide nucleic acid residues that independently are derivatized with the charged moiety on the alpha, beta, or gamma carbon. In some forms, all of the PNA probes independently include two to six peptide nucleic acid residues that independently are derivatized with the charged moiety on the alpha, beta, or gamma carbon. For example, one or more of the PNA probes can include one or more peptide nucleic acid residues that are derivatized with the charged moiety on the gamma carbon; derivatized with the charged moiety on the alpha carbon; or derivatized with the charged moiety on the beta carbon. Within a single probe molecule, the position for backbone modification is preferably always the same. For example, one or more of the PNA probes can include one or more peptide nucleic acid residues that are derivatized with the charged moiety solely on the gamma carbon; derivatized with the charged moiety solely on the alpha carbon; or derivatized with the charged moiety solely on the beta carbon. The preferred chemical composition within a PNA probe molecule includes chiral modifications of a single type, for example, a probe with all modifications in the gamma position, or a probe with all modifications in the alpha position.

In some forms, one or more of the charged moieties is lysine, for example, all of the charged moieties can be lysine. In some forms, one or more of the charged moieties in is L-lysine, for example, all of the charged moieties can be L-lysine. It is preferred that when L-lysine is used, the peptide nucleic acid residues are derivatized at the gamma carbon. It is preferred that when D-lysine is used, the peptide nucleic acid residues are derivatized at the alpha carbon. The choice between dextro (D) and levo (L) amino acids introduced in the PNA backbone can be informed or directed by the ability of each enantiomer to induce a right-handed conformation in the PNA backbone. This is affected by the position of the derivatizations of the peptide nucleic acid residues, with derivatizations at the gamma carbon favoring a right-handed conformation in the PNA backbone when used with L amino acids and with derivations at the alpha carbon favoring a right-handed conformation in the PNA backbone when used with D amino acids. For similar reasons, and on the same terms, the choice between derivatizations on the gamma carbon or the alpha carbon in the PNA backbone can be informed or directed by the ability of each enantiomer to induce a right-handed conformation in the PNA backbone. This is affected by the chiral form of the amino acid, with dextro (D) amino acids favoring a right-handed conformation in the PNA backbone when derivatized at the alpha carbon and with levo (L) amino acids favoring a right-handed conformation in the PNA backbone when derivatized at the gamma carbon.

In some forms, one or more of the PNA probes utilized by the methods independently include one or more peptide nucleic acid residues derivatized with a short-chain oligoethylene moiety on the alpha, beta, or gamma carbon. For example, one or more of the PNA probes can independently include one to nineteen peptide nucleic acid residues that independently are derivatized with the short-chain oligoethylene moiety on the alpha, beta, or gamma carbon. Therefore, in a particular form, all of the PNA probes independently include one to nineteen peptide nucleic acid residues that independently are derivatized with the short-chain oligoethylene moiety on the alpha, beta, or gamma carbon. In some forms, in one or more of the PNA probes utilized by the methods one or more of the peptide nucleic acid residues is derivatized with a short-chain oligoethylene moiety on the gamma carbon, for example, all of the PNA probes are derivatized with the short-chain oligoethylene moiety on the gamma carbon.

In some forms, one or more of the short-chain oligoethylene moieties is diethylene glycol, for example, all of the short-chain oligoethylene moieties can be diethylene glycol. When the PNA monomer modification is to be placed in the gamma position, the short-chain oligoethylene moiety, such as diethylene glycol, is preferably synthesized starting with L-serine. When the PNA monomer modification is to be placed in the alpha position, the short-chain oligoethylene moiety, such as diethylene glycol, is preferably synthesized starting with D-serine. The choice of serine enantiomer used for synthesis of PNA monomers can be informed or directed by the desire to induce a right-handed conformation on the backbone of the PNA probe.

Within the backbone of a single PNA probe, the gamma carbon modifications with short-chain oligoethylene moieties, such as diethylene glycol, based on monomer synthesis starting from L-serine, can be combined with additional backbone modifications based on a charged L-lysine on the gamma carbon. Conversely, within the backbone of a single PNA probe, the alpha carbon modifications with short-chain oligoethylene moieties, such as diethylene glycol, based on monomer synthesis starting from D-serine, can be combined with additional backbone modifications based on a charged D-lysine on the alpha carbon. The choice of compatible enantiomers can be informed or directed by the desire to induce a right-handed conformation in the backbone of the PNA probe. In further forms the capture tag is biotin or streptavidin.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows a single PNA oligomer that recognizes a single strand of dsDNA to form a triplex PNA-DNA complex. FIG. 1B shows a stable triplex invasion complex formed by interaction of two PNA oligomers with the same DNA strand, in which the unbound strand of DNA has been displaced. FIG. 1C shows a duplex invasion complex formed by a single PNA oligomer, resulting in displacement of a single DNA strand. FIG. 1D shows a double duplex invasion complex formed by pseudo-complementary PNA oligomers.

DETAILED DESCRIPTION OF THE INVENTION

Figure 1:
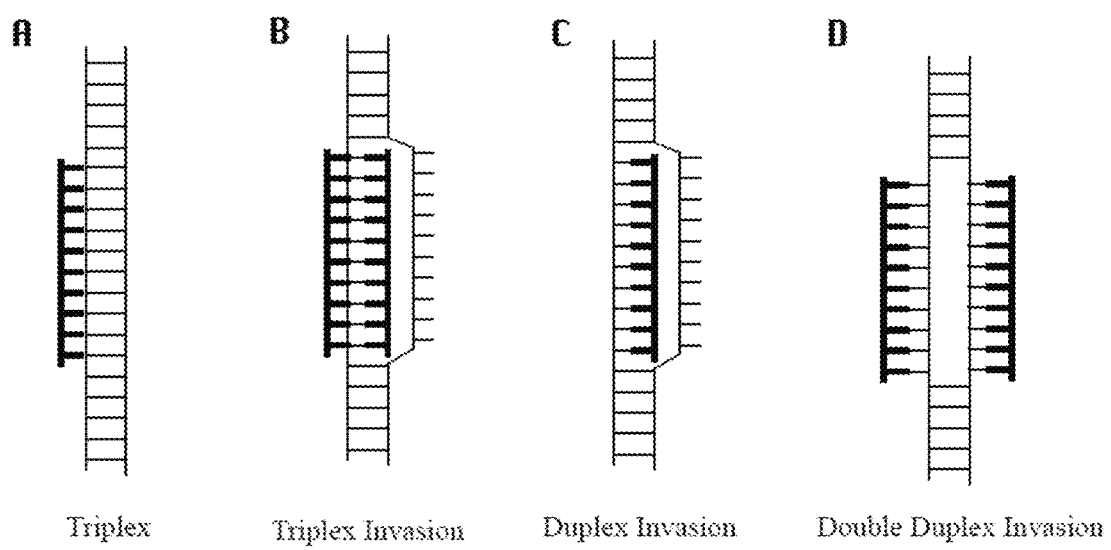
FIGS. 1A-1D are schematic representations of four modes of PNA oligomer interaction with double-stranded DNA (dsDNA). PNA oligomers are shown in bold.

The disclosed methods and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

It has been discovered that one or more large nucleic acid fragments (each between 2,000 base pairs in length and 40,000 base pairs in length) can be targeted and enriched from a mixture of nucleic acid fragments using sets of two or more sequence-specific PNA hybridization probes. For example, one or more large double-stranded DNA fragments can be targeted and enriched from a mixture of genomic DNA fragments using sets of two or more sequence-specific PNA hybridization probes.

Definitions

As used herein, "enrich" and "enrichment" refer to an increase in the proportion of a component relative to other components present or originally present. In the context of nucleic acids, enrichment of nucleic acids in a sample refers to an increase in the proportion of the nucleic acids in the sample relative to other molecules in the sample. "Selective enrichment" is enrichment of particular components relative to other components of the same type. In the context of nucleic acid fragments, selective enrichment of a particular nucleic acid fragment refers to an increase in the proportion of the particular nucleic acid fragment in a sample relative to other nucleic acid fragments present or originally present in the sample. The measure of enrichment can be referred to in different ways. For example, enrichment can be stated as the percentage of all of the components that is made up by the enriched component. For example, particular nucleic acid fragments can be enriched in an enriched nucleic acid sample to at least 90% of the enriched nucleic acid sample.

As used herein, "nucleic acid fragment" refers to a portion of a larger nucleic acid molecule. A "contiguous nucleic acid fragment" refers to a nucleic acid fragment that represents a single, continuous, contiguous sequence of the larger nucleic acid molecule. A "naturally occurring nucleic acid fragment" refers to a nucleic acid fragment that represents a single, continuous, contiguous sequence of a naturally occurring nucleic acid sequence.

As used herein, "DNA fragment" refers to a portion of a larger DNA molecule. A "contiguous DNA fragment" refers to a DNA fragment that represents a single, continuous, contiguous sequence of the larger DNA molecule. A "naturally occurring DNA fragment" refers to a DNA fragment that represents a single, continuous, contiguous sequence of a naturally occurring DNA sequence.

As used herein, "denatured nucleic acid" or "denatured DNA" refers to a nucleic acid that is denatured relative to a prior existing "native" or "non-denatured" state. For example, double-stranded nucleic acids, such as naturally-occurring dsDNA strands are completely denatured when separated into two corresponding single-stranded nucleic acid strands. Denaturation of nucleic acids can occur by chemical or physical means, such as exposure to salts or increased temperatures above the melting temperature of the dsDNA, or by interaction of dsDNA with a denaturing molecule, such as an antibody or enzyme. Denaturation can be partial, for example, resulting in partially or substantially denatured DNA, or complete, resulting in completely denatured DNA. Nucleic acid that has never been subjected to partial or complete denaturation is referred to as "never-denatured nucleic acid", such as never-denatured dsDNA.

As used herein, "naturally occurring" refers to a molecule that has the same structure or sequence as the corresponding molecule as it exists in nature. A naturally occurring molecule or sequence can still be considered naturally occurring when it is coupled to or incorporated into another molecule or sequence.

As used herein, "nucleic acid sample" refers to a composition, such as a solution, that contains or is suspected of containing nucleic acid molecules. An "enriched nucleic acid sample" is a nucleic acid sample in which nucleic acids, particular nucleic acid fragments, or a combination thereof, are enriched.

As used herein, "DNA sample" refers to a composition, such as a solution, that contains or is suspected of containing DNA molecules. An "enriched DNA sample" is a DNA sample in which DNA, particular DNA fragments, or a combination thereof, are enriched.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

As used herein, a "residue" of a chemical species refers to the moiety that is the resulting product of the chemical species in a particular reaction scheme or subsequent formulation or chemical product, regardless of whether the moiety is actually obtained from the chemical species. Thus, an ethylene glycol residue in a polymer refers to one or more —OCH$_2$CH$_2$O— units in the polymer, regardless of whether ethylene glycol was used to prepare the polyester. As another example, in a polymer of monomer subunits, the incorporated monomer subunits can be referred to as residues of the un-polymerized monomer.

As used herein, the term "nucleotide" refers to a molecule that contains a base moiety, a sugar moiety and a phosphate moiety. Nucleotides can be linked together through their phosphate moieties and sugar moieties creating an inter-nucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

As used herein, the term "nucleotide analog" refers to a nucleotide which contains some type of modification to the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

As used herein, the term "nucleotide substitute" refers to a nucleotide molecule having similar functional properties to nucleotides, but which does not contain a phosphate moiety. An exemplary nucleotide substitute is peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein. It is also possible to link other types of molecules (conjugates) to nucleotides or nucleotide analogs to enhance for example, interaction with DNA. Conjugates can be chemically linked to the nucleotide or nucleotide analogs. Exemplary conjugates include but are not limited to lipid moieties such as a cholesterol moiety. (Letsinger, et al., Proc. Natl. Acad. Sci. USA, 86:6553-6556 (1989)). There are many varieties of these types of molecules available in the art and available herein.

As used herein, the term "Watson-Crick interaction" refers to at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

As used herein, the term "Hoogsteen interaction" refers to the interaction that takes place on the Hoogsteen face of a nucleotide or nucleotide analog, which is exposed in the major groove of duplex DNA. The Hoogsteen face includes the N7 position and reactive groups (NH$_2$ or O) at the C6 position of purine nucleotides.

As used herein, the terms "oligonucleotide" or a "polynucleotide" are synthetic or isolated nucleic acid polymers including a plurality of nucleotide subunits.

As used herein, the term "non-natural amino acid" refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

As used herein, the term "peptide" refers to a class of compounds composed of amino acids chemically bound together. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides.

The term "modified" is often used herein to describe polymers and means that a particular monomeric unit that would typically make up the pure polymer has been replaced by another monomeric unit that shares a common polymerization capacity with the replaced monomeric unit. Thus, for example, it is possible to substitute diol residues for glycol in poly (ethylene glycol), in which case the poly (ethylene glycol) will be "modified" with the diol. If the poly (ethylene glycol) is modified with a mole percentage of the diol, then such a mole percentage is based upon the total number of moles of glycol that would be present in the pure polymer but for the modification. Thus, in a poly (ethylene glycol) that has been modified by 50 mole % with a diol, the diol and glycol residues are present in equimolar amounts.

The terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed oligonucleotides, nucleotide analogs, or nucleotide substitutes thereof and proteins disclosed herein, is through defining the variants and derivatives in terms of homology to specific known sequences. This identity of particular sequences disclosed herein is also discussed elsewhere herein. In general, variants of oligonucleotides, nucleotide analogs, or nucleotide substitutes thereof and proteins disclosed herein typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence.

Those of skill in the art readily understand how to determine the homology of two proteins or nucleic acids, such as genes. For example, the homology can be calculated after aligning the two sequences so that the homology is at its highest level. Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein. For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

As used herein, reference to there being some number of residues of a first description (such as residues not derivatized with a moiety) "between every residue" of a second description (such as residues derivatized with a moiety) means that, between every two residues of the second description that do not have any other residue of the second description between them, the specified number of residues of the first description are present. Thus, for example, the probe T*gTgC*cTccC*gTtTT*gTcC* (SEQ ID NO:6) is an example of a probe where, at different locations, zero, one, or two residues are not derivatized with a moiety between the residues that are derivatized with a moiety. If a residue of the second description is the last residue of the second description before the end of the probe (which can be referred to as an end-proximal residue of the second description), the reference to there being some number of residues of the first description between every residue of the second description does not apply to the residues between the end-proximal residue and the end of the probe. Thus, the average spacing between residues of the second description counts only the internal spacings without considering residues of the first description between each end and their respective end-proximal residue of the second description.

The residues of a first description between the end-proximal residue of a second description and the end of the probe can be referred to as flanking residues of the first description. For example, the probe T*gTgC*cTccC*gTtTT*gTcC* (SEQ ID NO:6) has a total of zero residues not derivatized with a moiety between both of the end-proximal derivatized residues and their respective ends of the probe and so has zero flanking residues not derivatized with a moiety. As another example, the probe cT*tCaT*CtCgT*cTaC*aaT*a (SEQ ID NO:10) has a total of two residues not derivatized with a moiety between both of the end-proximal derivatized residues and their respective ends of the probe and so has two flanking residues not derivatized with a moiety. As another example, the probe agT*CgTtC*tTcT*aTCaT*cT (SEQ ID NO:20) has a total of two residues not derivatized with a moiety between both of the end-proximal derivatized residues and their respective ends of the probe and so has two flanking residues not derivatized with a moiety.

As another example, the probe T*gTgC*cTccC*gTtTT*gTcC* (SEQ ID NO:6) has a total of zero residues not derivatized with a charged moiety between both of the end-proximal residues derivatized with a charged moiety and their respective ends of the probe and so has zero flanking residues not derivatized with a charged moiety. As another example, the probe cT*tCaT*CtCgT*cTaC*aaT*a (SEQ ID NO:10) has a total of one residue not derivatized with a charged moiety between both of the end-proximal residues derivatized with a charged moiety and their respective ends of the probe and so has one flanking residue not derivatized with a charged moiety. As another example, the probe agT*CgTtC*tTcT*aTCaT*cT (SEQ ID NO:20) has a total of four residues not derivatized with a charged moiety between both of the end-proximal residues derivatized with a charged moiety and their respective ends of the probe and so has four flanking residues not derivatized with a charged moiety.

Materials

Disclosed are materials, compositions, and components that can be used for the disclosed methods. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a matched set of peptide nucleic acid (PNA) hybridization probes is disclosed and discussed and a number of modifications that can be made to a number of molecules including the peptide nucleic acids of each of the probes are discussed, each and every combination and permutation of peptide nucleic acids and the modifications that are possible are specifically contemplated unless specifically indicated to the contrary. Thus, if a class of modifications A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Compounds

1. PNA Hybridization Probes

PNA hybridization probes (PNA probes) are oligomers of nucleic acid base pairing residues that include at least one peptide nucleic acid residue and are designed to and are capable of invading double-stranded DNA and hybridizing to a target sequence via Watson-Crick base pairing. In some forms, PNA probes include one or more capture tags. In some forms, the PNA probe is designed to target a sequence in a nucleic acid fragment. In some forms, the PNA probe includes one or more capture tags. In some forms, the PNA probe is designed to target a sequence in a nucleic acid fragment. In some forms, the PNA probe includes (a) one or more peptide nucleic acid residues that are derivatized with a charged moiety on the alpha carbon, beta carbon, gamma carbon, or combinations thereof, (b) one or more peptide nucleic acid residues that are derivatized with a neutral moiety on the alpha carbon, beta carbon, gamma carbon, or combinations thereof, or (c) combinations thereof.

In some forms, the PNA probe includes two to six peptide nucleic acid residues that independently are derivatized with a charged moiety on the alpha, beta, or gamma carbon. In some forms, one or more of the peptide nucleic acid residues that are derivatized with the charged moiety are derivatized with the charged moiety on the gamma carbon. In some forms, all of the peptide nucleic acid residues that are derivatized with the charged moiety are derivatized with the charged moiety on the gamma carbon. In some forms, one or more of the charged moieties are lysine. In some forms, all of the charged moieties are lysine. In some forms, one or more of the charged moieties are L-lysine. In some forms, all of the charged moieties are L-lysine.

In some forms, the PNA probe includes one or more peptide nucleic acid residues that are derivatized with a short-chain oligoethylene moiety on the alpha, beta, or gamma carbon. In some forms, the PNA probe includes one to nineteen peptide nucleic acid residues that independently are derivatized with the short-chain oligoethylene moiety on the alpha, beta, or gamma carbon. In some forms, one or more of the peptide nucleic acid residues that are derivatized with the short-chain oligoethylene moiety are derivatized with the short-chain oligoethylene moiety on the gamma carbon. In some forms, all of the peptide nucleic acid residues that are derivatized with the short-chain oligoethylene moiety are derivatized with the short-chain oligoethylene moiety on the gamma carbon. In some forms, one or more of the short-chain oligoethylene moieties are diethylene glycol. In some forms, all of the short-chain oligoethylene moieties are diethylene glycol.

In some forms, one or more of the PNA probes can independently include one or more peptide nucleic acid residues having a pseudo-complementary nucleobase as the base moiety of the peptide nucleic acid residue. In some forms, one or more of the PNA probes can independently include one to twenty-two peptide nucleic acid residues having a pseudo-complementary nucleobase as the base moiety of the peptide nucleic acid residue. In some forms, all of the PNA probes can independently include one to twenty-two peptide nucleic acid residues having a pseudo-complementary nucleobase as the base moiety of the peptide nucleic acid residue.

In some forms, the pseudo-complementary nucleobases are independently selected from the group consisting of pseudouridine (5-ribosyluracil); 7-Deaza-2'-deoxyguanosine; 2,6-Diaminopurine-2'-deoxyriboside; N4-Ethyl-2'-deoxycytidine; 2-thiothymidine; 2-aminoadenine; 2-aminopurine-riboside; 2,6-diaminopurine-riboside; 2'-deoxyisoguanosine; and 5-hydroxymethyl-2'-deoxycytidine.

In some forms, the one or more of the PNA probes that include one or more peptide nucleic acid residues having a pseudo-complementary nucleobase as the base moiety of the peptide nucleic acid residue is a subset of the PNA probes in the one or more sets of PNA probes. In some forms, the subset of the PNA probes in the one or more sets of PNA probes includes a subset of the PNA probes in the one or more sets of PNA probes that are predicted to be capable of interacting with one or more of the other PNA probes in the one or more sets of PNA probes. In some forms, the subset of the PNA probes in the one or more sets of PNA probes is a subset of the PNA probes in the one or more sets of PNA probes that are predicted to be capable of interacting with one or more of the other PNA probes in the one or more sets of PNA probes.

In some forms, the capture tag is biotin or streptavidin. In some forms, the PNA probe is derivatized with one or more amino acids on at least one of the terminal PNA residues. In some forms, the PNA probe is derivatized with two or more lysine residues on at least one of the terminal PNA residues.

In some forms the hybridization probes include peptide nucleic acid (PNA) oligomers that combine PNA monomers modified at the gamma position with neutral and charged moieties.

Sets of two or more PNA hybridization probes including a combination of charged and neutral gamma modifications can be designed to target any nucleic acid sequence (such as DNA or RNA sequence). For example, PNA probes can be designed to be complementary to a target nucleotide sequence unique to a particular gene, nucleic acid fragment, or DNA fragment from a highly complex nucleic acid sample, such as a whole genomic DNA sample. The target nucleic acid sequence can be any suitable length. For example, the target nucleic acid sequence can be between 8 and 30 nucleotides in length, typically between 15 and 25 nucleotides. A preferred nucleic acid target sequence is between 18 and 22 nucleotides in length, inclusive, for example, 20 nucleotides in length.

In some forms, PNA probes are designed to combine PNA monomers with gamma Mini-PEG modifications and PNA monomers with gamma L-Lysine modifications for optimal solubility, rapid hybridization kinetics, high melting temperature after DNA hybridization, as well as good mismatch discrimination. The positively-charged Lysine residues undergo charge repulsion when contacting other PNA molecules. For this reason, PNA probes with 2 or more gamma-L-Lysine modifications are less likely to undergo intermolecular hybridization associations with other probes of different sequence present in a mixture containing thousands of different PNA sequences, designed to invade different DNA targets. Exemplary PNA probes are provided in Table 1. Each hybridization probe includes one or more capture tags, such as a biotin moiety, to enable isolation of the target nucleic acid fragments by, for example, affinity chromatography. Each hybridization probe optionally includes amino-acid adducts to enhance aqueous solubility, for example, two lysine residues.

PNA hybridization probes can be readily synthesized using techniques generally known to synthetic organic chemists.

i. Target Nucleic Acid Sequences

Short PNA probes can be designed and used as capture probes for enrichment of a specific nucleic acid target sequence. The design of hybridization probes for sequence-specific nucleic acid capture according to the disclosed methods requires knowledge of two or more target sequences within each different target nucleic acid fragment. Typically, multiple distinct target sequences for the short PNA hybridization probes are prevalent in large nucleic acid molecules.

The term "k-mers" refers to short nucleic acid sequences, where "k" denotes the number of positions in a short string of nucleotide bases. Typically, each probe in a set of probes designed for use according to the disclosed methods should be complementary to a short (preferably 18 to 22 bases) nucleotide sequence that is unique in the sequences present in the nucleic acid sample. For example, for enrichment of genomic DNA fragments the probe should be complementary to a short (preferably 18 to 22 bases) nucleotide sequence that is unique in the sequences present in the genome.

Typically, the hybridization probes are designed as matched sets of two or more probes that target nucleotide sequences within the same desired DNA fragment. The optimal number of different hybridization probes designed to target a nucleic acid fragment by the described methods can vary depending upon the size of the nucleic acid fragment being targeted. Preferably, two or more probes may be used to target fragments up to 20,000 base pairs in length, three or more probes may be used to target fragments up to 30,000 base pairs in length, and four or more probes may be used to target fragments up to 40,000 base pairs in length.

It is possible to design PNA probes that work in pairs by hybridizing to each strand of the target DNA. Therefore, although not preferred, the two or more target sequences can be overlapping, partially overlapping or non-overlapping, for example, adjacent or contiguous sequences in the target nucleic acid fragment. In some forms, target sequences that are overlapping, partially overlapping, or both can be excluded. In some forms, two or more target sequences are separated by one or more nucleotides. In some forms, the hybridization probes are designed to induce duplex invasion or triplex invasion of the target nucleic acid. Therefore, although not preferred, hybridization probes can include two or more target sequences that are partially overlapping, or non-overlapping on the target nucleic acid fragment. In some forms, hybridization probes that are capable of inducing triplex invasion of the target nucleic acid are designed to induce triplex invasion of the target nucleic acid, or both, can be excluded. In some forms, although not preferred, a matched pair of two hybridization probes include palindromic (self-complementary) sequences can be used in methods for double-duplex invasion of a target DNA fragment.

Hybridization probes having target sequences that are not unique can target, invade and capture multiple sequences in the genome. Therefore, in some forms, a set of two or probes designed for use according to the disclosed methods performs multiplexed double stranded DNA sequence capture most specifically when each probe in the set is complementary to a DNA sequence for which the number of k-mers in the genome that differ by only one base is zero. Capture by each probe in a probe set is more specific when the number of k-mers in the genome that differ by only two bases is zero. Capture by each probe in a probe set is even more specific when the number of k-mers in the genome that differ by only three bases is zero. Bioinformatics tools can be used to identify in the genome candidate probe sequences that meet the desired uniqueness requirement: absence at other genomic positions of closely related sequences that differ by one or two or even three mismatches.

Bioinformatics tools for sequence information of the human genome is available from multiple sources, for example, the UCSC database (version hg12; Jun. 28, 2002) (internet site genome.ucsc.edu/goldenPath/28jun2002) developed by the International Human Genome Mapping Consortium.

Preferably, probe candidates do not include k-mers capable of self-folding to form a stable secondary structure. These k-mers have a lower probability of interacting with a target sequence, since they are trapped into a thermodynamically stable self-folding configuration.

TABLE 1

Examples of PNA probes.

| Probe No. | Capture Tag | Total number of base-containing residues | Total number of PNA residues | Total number of underivatized PNA residues | Total number of PNA residues derivatized with a charged moiety | Total number of PNA residues derivatized with a neutral moiety | Charged residues on terminal PNA residue |
|---|---|---|---|---|---|---|---|
| 1 | Yes | 20 | 20 | 0 | 2 | 18 | 2 |
| 2 | Yes | 20 | 20 | 0 | 3 | 17 | 2 |
| 3 | Yes | 20 | 20 | 0 | 4 | 16 | 2 |
| 4 | Yes | 20 | 20 | 0 | 5 | 15 | 2 |
| 5 | Yes | 20 | 20 | 0 | 6 | 14 | 2 |

TABLE 1-continued

Examples of PNA probes.

| Probe No. | Capture Tag | Total number of base-containing residues | Total number of PNA residues | Total number of underivatized PNA residues | Total number of PNA residues derivatized with a charged moiety | Total number of PNA residues derivatized with a neutral moiety | Charged residues on terminal PNA residue |
|---|---|---|---|---|---|---|---|
| 6 | Yes | 20 | 20 | 1 | 2 | 17 | 2 |
| 7 | Yes | 20 | 20 | 1 | 3 | 16 | 2 |
| 8 | Yes | 20 | 20 | 1 | 4 | 15 | 2 |
| 9 | Yes | 20 | 20 | 1 | 5 | 14 | 2 |
| 10 | Yes | 20 | 20 | 1 | 6 | 13 | 2 |
| 11 | Yes | 20 | 20 | 2 | 2 | 16 | 2 |
| 12 | Yes | 20 | 20 | 2 | 3 | 15 | 2 |
| 13 | Yes | 20 | 20 | 2 | 4 | 14 | 2 |
| 14 | Yes | 20 | 20 | 2 | 5 | 13 | 2 |
| 15 | Yes | 20 | 20 | 2 | 6 | 12 | 2 |
| 16 | Yes | 20 | 20 | 3 | 2 | 15 | 2 |
| 17 | Yes | 20 | 20 | 3 | 3 | 14 | 2 |
| 18 | Yes | 20 | 20 | 3 | 4 | 13 | 2 |
| 19 | Yes | 20 | 20 | 3 | 5 | 12 | 2 |
| 20 | Yes | 20 | 20 | 3 | 6 | 11 | 2 |
| 21 | Yes | 20 | 20 | 4 | 2 | 14 | 2 |
| 22 | Yes | 20 | 20 | 4 | 3 | 13 | 2 |
| 23 | Yes | 20 | 20 | 4 | 4 | 12 | 2 |
| 24 | Yes | 20 | 20 | 4 | 5 | 11 | 2 |
| 25 | Yes | 20 | 20 | 4 | 6 | 10 | 2 |
| 26 | Yes | 20 | 20 | 5 | 2 | 13 | 2 |
| 27 | Yes | 20 | 20 | 5 | 3 | 12 | 2 |
| 28 | Yes | 20 | 20 | 5 | 4 | 11 | 2 |
| 29 | Yes | 20 | 20 | 5 | 5 | 10 | 2 |
| 30 | Yes | 20 | 20 | 5 | 6 | 9 | 2 |
| 31 | Yes | 20 | 20 | 6 | 2 | 12 | 2 |
| 32 | Yes | 20 | 20 | 6 | 3 | 11 | 2 |
| 33 | Yes | 20 | 20 | 6 | 4 | 10 | 2 |
| 34 | Yes | 20 | 20 | 6 | 5 | 9 | 2 |
| 35 | Yes | 20 | 20 | 6 | 6 | 8 | 2 |
| 36 | Yes | 20 | 20 | 7 | 2 | 11 | 2 |
| 37 | Yes | 20 | 20 | 7 | 3 | 10 | 2 |
| 38 | Yes | 20 | 20 | 7 | 4 | 9 | 2 |
| 39 | Yes | 20 | 20 | 7 | 5 | 8 | 2 |
| 40 | Yes | 20 | 20 | 7 | 6 | 7 | 2 |
| 41 | Yes | 20 | 20 | 8 | 2 | 10 | 2 |
| 42 | Yes | 20 | 20 | 8 | 3 | 9 | 2 |
| 43 | Yes | 20 | 20 | 8 | 4 | 8 | 2 |
| 44 | Yes | 20 | 20 | 8 | 5 | 7 | 2 |
| 45 | Yes | 20 | 20 | 8 | 6 | 6 | 2 |
| 46 | Yes | 20 | 20 | 9 | 2 | 9 | 2 |
| 47 | Yes | 20 | 20 | 9 | 3 | 8 | 2 |
| 48 | Yes | 20 | 20 | 9 | 4 | 7 | 2 |
| 49 | Yes | 20 | 20 | 9 | 5 | 6 | 2 |
| 50 | Yes | 20 | 20 | 9 | 6 | 5 | 2 |
| 51 | Yes | 20 | 20 | 10 | 2 | 8 | 2 |
| 52 | Yes | 20 | 20 | 10 | 3 | 7 | 2 |
| 53 | Yes | 20 | 20 | 10 | 4 | 6 | 2 |
| 54 | Yes | 20 | 20 | 10 | 5 | 5 | 2 |
| 55 | Yes | 20 | 20 | 10 | 6 | 4 | 2 |
| 56 | Yes | 20 | 20 | 11 | 2 | 7 | 2 |
| 57 | Yes | 20 | 20 | 11 | 3 | 6 | 2 |
| 58 | Yes | 20 | 20 | 11 | 4 | 5 | 2 |
| 59 | Yes | 20 | 20 | 11 | 5 | 4 | 2 |
| 60 | Yes | 20 | 20 | 11 | 6 | 3 | 2 |
| 61 | Yes | 20 | 20 | 12 | 2 | 6 | 2 |
| 62 | Yes | 20 | 20 | 12 | 3 | 5 | 2 |
| 63 | Yes | 20 | 20 | 12 | 4 | 4 | 2 |
| 64 | Yes | 20 | 20 | 12 | 5 | 3 | 2 |
| 65 | Yes | 20 | 20 | 12 | 6 | 2 | 2 |
| 66 | Yes | 20 | 20 | 13 | 2 | 5 | 2 |
| 67 | Yes | 20 | 20 | 13 | 3 | 4 | 2 |
| 68 | Yes | 20 | 20 | 13 | 4 | 3 | 2 |
| 69 | Yes | 20 | 20 | 13 | 5 | 2 | 2 |
| 70 | Yes | 20 | 20 | 13 | 6 | 1 | 2 |
| 71 | Yes | 20 | 20 | 14 | 2 | 4 | 2 |
| 72 | Yes | 20 | 20 | 14 | 3 | 3 | 2 |
| 73 | Yes | 20 | 20 | 14 | 4 | 2 | 2 |
| 74 | Yes | 20 | 20 | 14 | 5 | 1 | 2 |

TABLE 1-continued

Examples of PNA probes.

| Probe No. | Capture Tag | Total number of base-containing residues | Total number of PNA residues | Total number of underivatized PNA residues | Total number of PNA residues derivatized with a charged moiety | Total number of PNA residues derivatized with a neutral moiety | Charged residues on terminal PNA residue |
|---|---|---|---|---|---|---|---|
| 75 | Yes | 20 | 20 | 14 | 6 | 0 | 2 |
| 76 | Yes | 20 | 20 | 15 | 2 | 3 | 2 |
| 77 | Yes | 20 | 20 | 15 | 3 | 2 | 2 |
| 78 | Yes | 20 | 20 | 15 | 4 | 1 | 2 |
| 79 | Yes | 20 | 20 | 15 | 5 | 0 | 2 |
| 80 | Yes | 16 | 16 | 6 | 6 | 4 | 2 |
| 81 | Yes | 17 | 17 | 7 | 6 | 4 | 2 |
| 82 | Yes | 18 | 18 | 8 | 6 | 4 | 2 |
| 83 | Yes | 19 | 19 | 9 | 6 | 4 | 2 |
| 84 | Yes | 21 | 21 | 11 | 6 | 4 | 2 |
| 85 | Yes | 22 | 22 | 12 | 6 | 4 | 2 |
| 86 | Yes | 23 | 23 | 13 | 6 | 4 | 2 |
| 87 | Yes | 24 | 24 | 14 | 6 | 4 | 2 |
| 88 | Yes | 25 | 25 | 15 | 6 | 4 | 2 |
| 89 | Yes | 26 | 26 | 16 | 6 | 4 | 2 |
| 90 | Yes | 16 | 16 | 8 | 6 | 2 | 2 |
| 91 | Yes | 17 | 17 | 9 | 6 | 2 | 2 |
| 92 | Yes | 18 | 18 | 10 | 6 | 2 | 2 |
| 93 | Yes | 19 | 19 | 11 | 6 | 2 | 2 |
| 94 | Yes | 21 | 21 | 13 | 6 | 2 | 2 |
| 95 | Yes | 22 | 22 | 14 | 6 | 2 | 2 |
| 96 | Yes | 23 | 23 | 15 | 6 | 2 | 2 |
| 97 | Yes | 24 | 24 | 16 | 6 | 2 | 2 |
| 98 | Yes | 25 | 25 | 17 | 6 | 2 | 2 |
| 99 | Yes | 26 | 26 | 18 | 6 | 2 | 2 |
| 100 | Yes | 16 | 16 | 9 | 6 | 1 | 2 |
| 101 | Yes | 17 | 17 | 10 | 6 | 1 | 2 |
| 102 | Yes | 18 | 18 | 11 | 6 | 1 | 2 |
| 103 | Yes | 19 | 19 | 12 | 6 | 1 | 2 |
| 104 | Yes | 21 | 21 | 14 | 6 | 1 | 2 |
| 105 | Yes | 22 | 22 | 15 | 6 | 1 | 2 |
| 106 | Yes | 23 | 23 | 16 | 6 | 1 | 2 |
| 107 | Yes | 24 | 24 | 17 | 6 | 1 | 2 |
| 108 | Yes | 25 | 25 | 18 | 6 | 1 | 2 |
| 109 | Yes | 26 | 26 | 19 | 6 | 1 | 2 |

Computer programs are available to identify those undesirable self-folding k-mers. Short k-mer sequences, typically 18 to 22 bases in length, that are unique and also suitable for specific targeting and capture by strand invasion can occur at a frequency that is less than 1,000 in 10,000 base pairs.

Typically, DNA target sequences of hybridization probes designed for use according to the disclosed methods are characterized by having a melting temperature that is relatively low. For example, for a sequence of 20 contiguous nucleotides in a genome, the expected melting temperature can be calculated using values for entropy and enthalpy characteristic of each dinucleotide, as described by Santa Lucia, Proc. Natl. Acad. Sci. USA, Vol. 95, pp. 1460-1465 (1998). Therefore, in an exemplary genomic domain of 30,000 base pairs, 29,980 k-mers each of 20 base pairs can be enumerated. A computer-based algorithm can be used to calculate the predicted melting temperature of all 29,980 k-mers in this genomic interval.

A useful 20-base DNA target sequences according to the disclosed methods is characterized by having a melting temperature that belongs to the lowest half (50%) of all computed 20-base DNA melting temperatures. A particularly 20-base DNA target sequences according to this invention is characterized by having a melting temperature that belongs to the lowest one-third (33%) of all computed 20-base DNA melting temperatures.

In order to use a multiplicity of hybridization probes in a single reaction volume it is preferred that all the probe sequences in the set are unable to hybridize with each other. This requirement is satisfied when each possible PNA sequence alignment between all possible combinations of all probe pairs has at least 3 mismatched bases, or more preferably at least 4 mismatches, or more preferably at least 5 mismatches, or even more preferably at least 6 mismatches. Any computer programs known in the art can be used to examine the likelihood of cross-reactivity amongst all PNA probe candidates in a set of several thousand probe candidates, to make sure that the preferred condition of no inter-probe cross-hybridization is met by all probe pairs.

a. Exemplary Targets

Exemplary target sequences for target-specific enrichment include one or more components of a specific genome, for example, the human genome. Exemplary human genomic DNA that can be targeted and enriched includes DNA located in the MHC region. For example, in particular forms, target sequences include genetic elements of human genomic DNA located in the MHC region of chromosome 6.

In some forms, target sequences for target-specific enrichment include genomic components of the MHC known to be associated with one or more specific immunological features or phenotypes. Exemplary immunological features or phenotypes include having predisposition to autoimmune diseases, or showing symptoms of autoimmune diseases. Therefore, in some forms, target sequences enrich regions of genomic DNA where sequence variation is associated with immunological features such as autoimmune diseases. Exemplary genes associated with sequence variation relating to autoimmune diseases include, among others, the DRB1 and DQA1 genes. Therefore, in some forms, targeted genomic DNA fragments include the DRB1 gene, or fragments of the DRB1 gene. In some forms, targeted genomic DNA fragments include the DQA1 gene, or fragments of the DQA1 gene. In some forms, targeted DNA fragments include the DQA1 gene, or fragments of the DQA1 gene and the DRB1 gene, or fragments of the DRB1 gene. An exemplary genomic target region is 90,000 bases in length and spans the genomic co-ordinates chr6:32522981-32612981 (coordinates based on human genome build hg19). In some forms, targeted human genomic DNA is located in the Major Histocompatibility Complex (MHC) region of chromosome 6, for example, the DRB1 and DQA1 genes.

In some forms, targeted genomic DNA includes a 40,000 base window that spans a region starting at −22,000 bases upstream of the human FOXP3 (Forkhead Box P3, expressed in regulatory T-cells) promoter, and ending 18,000 bases downstream of the FOXP3 promoter. Therefore, in some forms the targeted genomic DNA includes the human FOXP3 gene, or fragments of the FOXP3 gene. An exemplary genomic target region is the sequence spanning the genomic coordinates chrX:49103288-49143288 (coordinates based on human genome build hg19). Exemplary targeted genomic DNA from this region includes seven sequences, separated from each other by an average of 5,714 base pairs in the genome.

In some forms, target sequences include genetic elements associated with one or more diseases or conditions, or having a known correlation with development of one or more disease or conditions (i.e., associated with disease risk). Exemplary diseases are autoimmune diseases, diabetes, and the metabolic syndrome, and cancer. For example, in a particular form, target sequences include genetic elements from more than 40 or 50 mega-bases of human genomic DNA located within enhancer elements associated with disease risk for autoimmune diseases, or enhancer elements associated with disease risk for diabetes and the metabolic syndrome. For example, in some forms, targeted DNA includes enhancer clusters associated with important diseases, such as Type II diabetes. 3,677 enhancer clusters have been identified which mapped near genes with strong pancreatic islet-enriched expression (Pasquali et al., Nat Genet. 2014 February; 46(2):136-43 (2014)). Therefore, in some forms, targeted DNA includes genomic DNA windows of 30,000 to 150,000 base pairs to encompass all of the enhancers within a cluster. For example, targeted sequences can be of unique sequence at an average distance of 5,000 to 7,000 bases from each other within each cluster.

Other target sequences include enhancer elements associated with the differentiation of different subsets of white blood cells.

In some forms, target sequences include entire subsets of genomic DNA from a single genome, or mixtures of two or more genomes from the same or different species, such as mitochondrial DNA. For example, in a particular form, target sequences include components of the human mitochondrial genome. In some forms, target sequences include the dog mitochondrial genome, or the cat mitochondrial genome.

In further forms, target sequences include genomic DNA of one or more species of bacteria, archaea, fungi, protozoa, or mixtures of two or more of these. Therefore, target sequences can be sequences of genomic DNA of one or more species of bacteria present in the human oral cavity, one or more species of bacteria present in the human airway, or present in the human urogenital tract, or known to exist in human blood or feces.

ii. Peptide Nucleic Acid (PNA)

Peptide nucleic acid (PNA) is a nucleic acid mimic where the native nucleic acid sugar-phosphate backbone is replaced by an N-(2-aminoethyl) glycine unit. Thus, unlike DNA and other DNA analogs, PNAs do not include phosphate groups or pentose sugar moieties. A methyl carbonyl linker connects natural as well as unusual (in some cases) nucleotide bases to this backbone at the amino nitrogens. Un-modified PNAs are non-ionic, achiral, neutral molecules and are not susceptible to hydrolytic (enzymatic) cleavage. The term "un-modified PNA residues" refers to a PNA residue including an N-(2-aminoethyl)-glycine backbone (see Formula III). The term "derivatized PNA" or "modified PNA" refers to a PNA residue having one or more substitutions or derivatized groups at one or more positions of the un-modified PNA structure.

PNA can be synthesized and modified by any means known in the art. Typically, the procedures for PNA synthesis are similar to those employed for peptide synthesis, using standard solid-phase manual or automated synthesis. Suitable experimental methods for making and derivatizing compounds including PNA and modified PNA are described in Bahal, et al., Current Gene Therapy, Vol. 14, No. 5 (2014); Bahal, et al., Artificial DNA: PNA & XNA 4:2, 49-57 (2013); De Costa, et al., PLOS One, Vol. 8, (3) e58670 (2013); Dragulescu-Andrasi, J. Am. Chem. Soc. 128, 10258-10267 (2006); Englund, et al., Org. Lett., Vol. 7, No. 16, 3465-3467 (2005); Ishizuka, et al., Nucleic acids Research, Vol. 36, No. 5, 1464-1471 (2008); Huang, et al., Arch Pharm Res Vol 35, No 3, 517-522, (2012); Kuhn, et al., Artificial DNA: PNA & XNA 1:1, 45-53 (2010); Sugiyama, et al., Molecules, 18, 287-310 (2013); Sahu, et al., J Org Chem. 15; 76(14): 5614-5627 (2011); and Yeh, et al., J Am Chem Soc.; 132(31): 10717-10727 (2010), which are incorporated by reference in their entireties.

Despite variations from natural nucleic acids, PNA is still capable of sequence-specific binding to DNA as well as RNA obeying the Watson-Crick hydrogen bonding rules. PNA shows potential in many applications, including biosensing and therapeutics, due to its high binding affinity and selectivity for DNA and RNA. PNA forms highly stable complexes with target DNA and PNA-DNA complexes have a higher thermal melting temperature ($T_m$), as compared to the corresponding DNA-DNA or DNA-RNA duplexes formed by the same nucleotide sequence. In addition, hybridization of PNAs with target DNA can occur virtually independent of salt concentration and the $T_m$ of PNA-DNA duplex is generally not affected by low ionic strength. Therefore, PNAs can hybridize to DNA or RNA sequences involved in secondary structures, which are destabilized by low ionic strength.

In contrast to DNA, PNA can bind in either a parallel or antiparallel manner and PNA hybridization probes will bind to either single-stranded DNA or to double-stranded DNA.

PNA hybridization probes are capable of invading complementary target sequences in DNA duplexes in vitro, as well as in living cells. Strand invasion of double stranded DNA by peptide nucleic acids (PNA) has been extensively described in the literature (Ito et al., 1992a; Ito, Smith, Cantor (1992b)). Early published examples of the use of PNA for DNA capture rely on the ability of PNA molecules to engage in DNA triplex interactions that are readily formed in DNA sequences that contain homo-purine-rich sequences. For example, PNAs were used to isolate specific sequence repeats from a human genomic library, as well as for isolation of a single copy clone from a yeast genomic library. However, PNA triplex interactions are not preferred because it is difficult to design sufficiently specific triplex probes for capture of a multiplicity of different loci in the genome.

Strand invasion by PNA is more efficient in vitro, at low salt concentrations, and slower at physiological salt concentrations. Several methods have been applied to sequence-specific enrichment of DNA by PNA-based capture. For example, PNAs containing diaminopurine-thiouracil base pairs bind with high specificity and efficiency to complementary targets in double-stranded DNA by a mechanism termed "double duplex invasion" in which the duplex is unwound and both DNA strands are targeted simultaneously, each by a different PNA containing pseudo-complementary bases (Lohse et. al, 1999) (see FIG. 1). When two PNA probes, each containing pseudo-complementary bases are used to target a specific DNA sequence, the two PNAs are unable to hybridize with each other due to the steric clashes of the pseudo-complementary bases. By contrast, the interactions with each of the DNA strands are highly stable. Double duplex invasion has been used successfully for targeted correction of a thalassemia-associated beta globin mutation (Lonkar, et al., 2009).

a. Modifications of PNA

PNA probes can include PNA modified by any means known in the art to change the structural and functional features of the probes. In some forms, chemical modifications of PNA change one or more structural characteristics of the PNA.

PNA monomers including any of the modifications described herein can be incorporated into oligomers. Therefore, PNA probes can be PNA oligomers including modified PNA monomers, unmodified PNA monomers, and combinations thereof. In some forms, PNA probes include a multiplicity of variously modified PNA monomers. For example, matched pairs of self-complementary PNA probes can be modified to reduce the thermal stability of the PNA:PNA duplex formed by the probes in each pair. In addition, PNA probes can include PNA monomers modified to enhance sequence-specificity and affinity of DNA-PNA duplexes; and to reduce non-specific interactions.

Although not preferred, PNA oligomers can include bis-PNA oligomers. Bis-PNA binds specific target sequences to form a looped-out single strand and an internal, triple-stranded invaded complex. Bis-PNA can be prepared in a continuous synthesis process by connecting two PNA segments via a flexible linker composed of multiple units of either 8-amino-3,6-dioxaoctanoic acid or 6-aminohexanoic acid (Ray and Norden, The FASEB Journal, vol. 14 no. 9 1041-1060 (2000)). In some forms, bis-PNA oligomers can be excluded.

(A) Pseudo-Complementary Bases

Pseudo-complementary (PC) nucleobases are non-standard bases that have significantly reduced affinity for forming duplexes with each other due to chemical modification, but retain strong base pairs with natural DNA or RNA targets and can readily hybridize to unmodified nucleic acids. Therefore, the differential hybridization properties of pc-nucleic acids provides for efficient sequence-specific targeting of duplex DNA by double duplex invasion strategies. When pseudo-complementary invading PNA pairs are utilized for DNA strand invasion, the total number of probes used for DNA capture is effectively doubled, as compared to a single invading PNA.

A non-limiting list of pseudo-complementary nucleobases includes Pseudouridine (5-Ribosyluracil); 7-Deaza-2'-deoxyguanosine; 2,6-Diaminopurine-2'-deoxyriboside; N4-Ethyl-2'-deoxycytidine; 2-Thiothymidine; 2-aminoadenine; 2-Aminopurine-riboside; 2,6-Diaminopurine-riboside; 2'-Deoxyisoguanosine; and 5-Hydroxymethyl-2'-deoxycytidine (see Formula I). Pseudo-complementary invading PNA pairs form stable Watson:Crick interactions with natural DNA bases, but are not capable of stable hydrogen bonding among themselves (Lohse et al 1999), as depicted in Formula II. For example, Diaminopurine can form an extra hydrogen bond with thymine, whereas a steric clash occurs between diaminopurine and thiouracil.

In some forms, PNA probes are designed for use in a capture method based on pseudo-complementary invading PNA pairs. For example, PNA probes can be designed for double duplex invasion by pseudo-complementary PNA to achieve sequence-specific capture of a multiplicity of double-stranded DNA domains from eukaryotic genomes.

Chemical structures of non-standard nucleobases

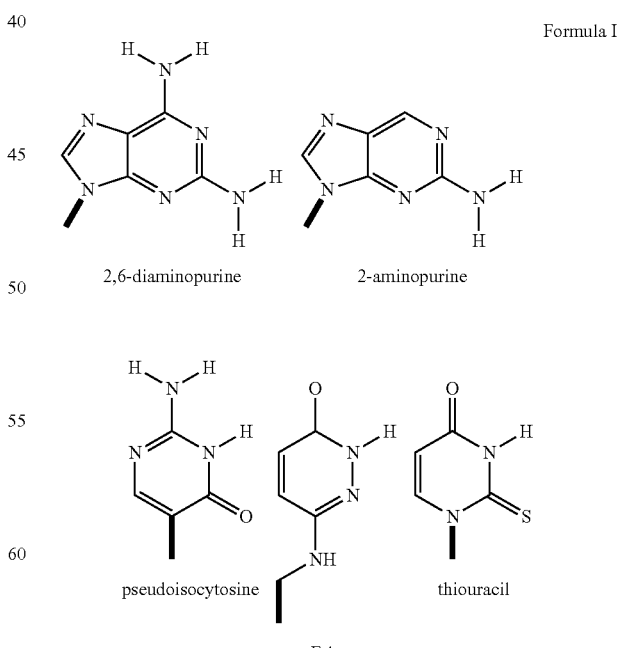

Formula I 2,6-diaminopurine    2-aminopurine pseudoisocytosine    thiouracil

E-base adenine-thymidine; diaminopurine-thymidine; adenine-thiouracil, and adenine-thiouracil base pairs.

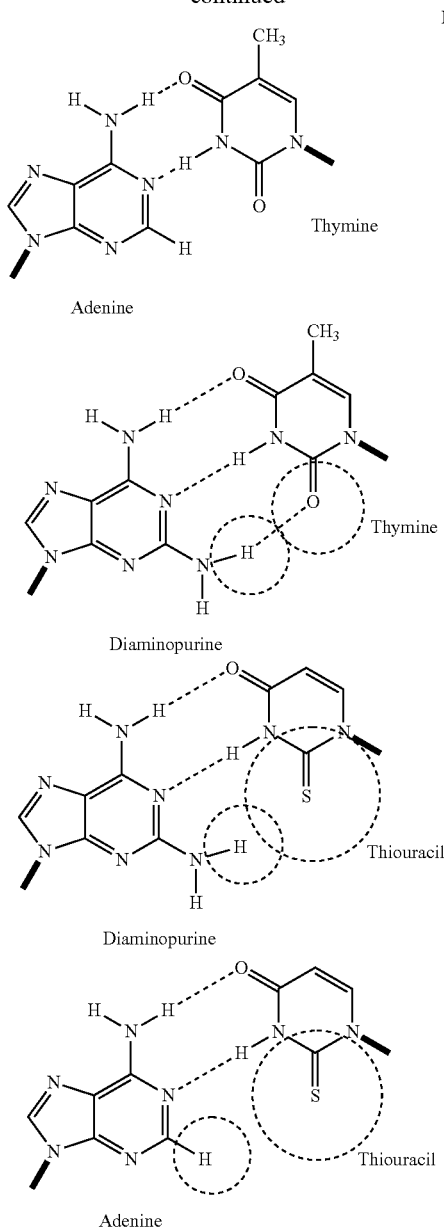

Formula II

Adenine / Thymine

Diaminopurine / Thymine

Diaminopurine / Thiouracil

Adenine / Thiouracil

Pseudo-complementary bases can be useful for incorporating into PNA probes when numerous different PNA probes in a single capture reaction. For example, pseudo-complementary bases can be useful when thousands of PNA probes are used together to capture numerous target sequences. In certain such forms, the pseudo-complementary bases can be incorporated, for example, just into a particular subset of PNA probes. For example, the pseudo-complementary bases can be incorporated into a subset of PNA probes that computer analysis predicts to be capable of interacting with each other. Use of such PNA probes can reduce or eliminate undesired probe-probe interactions. In some forms, use of pseudo-complementary bases in PNA probes can be excluded.

In some forms, one or more of the PNA probes can independently include one or more peptide nucleic acid residues having a pseudo-complementary nucleobase as the base moiety of the peptide nucleic acid residue. In some forms, one or more of the PNA probes can independently include one to twenty-two peptide nucleic acid residues having a pseudo-complementary nucleobase as the base moiety of the peptide nucleic acid residue. In some forms, all of the PNA probes can independently include one to twenty-two peptide nucleic acid residues having a pseudo-complementary nucleobase as the base moiety of the peptide nucleic acid residue.

In some forms, the pseudo-complementary nucleobases are independently selected from the group consisting of pseudouridine (5-ribosyluracil); 7-Deaza-2'-deoxyguanosine; 2,6-Diaminopurine-2'-deoxyriboside; N4-Ethyl-2'-deoxycytidine; 2-thiothymidine; 2-aminoadenine; 2-aminopurine-riboside; 2,6-diaminopurine-riboside; 2'-deoxyisoguanosine; and 5-hydroxymethyl-2'-deoxycytidine.

In some forms, the one or more of the PNA probes that include one or more peptide nucleic acid residues having a pseudo-complementary nucleobase as the base moiety of the peptide nucleic acid residue is a subset of the PNA probes in the one or more sets of PNA probes. In some forms, the subset of the PNA probes in the one or more sets of PNA probes includes a subset of the PNA probes in the one or more sets of PNA probes that are predicted to be capable of interacting with one or more of the other PNA probes in the one or more sets of PNA probes. In some forms, the subset of the PNA probes in the one or more sets of PNA probes is a subset of the PNA probes in the one or more sets of PNA probes that are predicted to be capable of interacting with one or more of the other PNA probes in the one or more sets of PNA probes.

(B) Chiral Backbone Modifications of PNA

In some forms, chemical modifications in the structure of the PNA backbone can give rise to changes in functional characteristics of PNA. Functional characteristics of PNA that can be modified include binding affinity, binding specificity, aqueous solubility, thermal stability, and combinations thereof. For example, addition of side chains at the gamma-position of the PNA backbone can pre-organize the backbone to increase binding affinity, and enable a diverse range of chemical functionalities to be incorporated via addition of amino acid building blocks. A large number of chemical modifications of the original aminoethyl glycine PNA backbone are known. Some are shown in Formula III.

Chemical structures of a selection of PNA monomer units

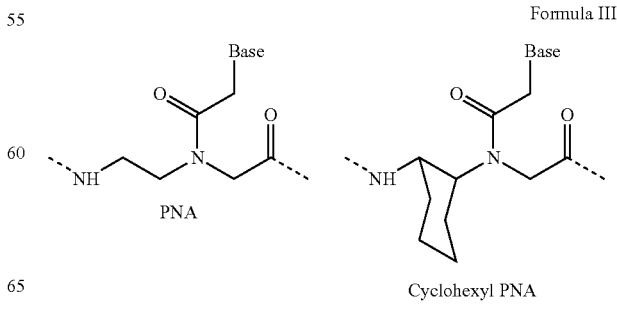

Formula III

PNA / Cyclohexyl PNA

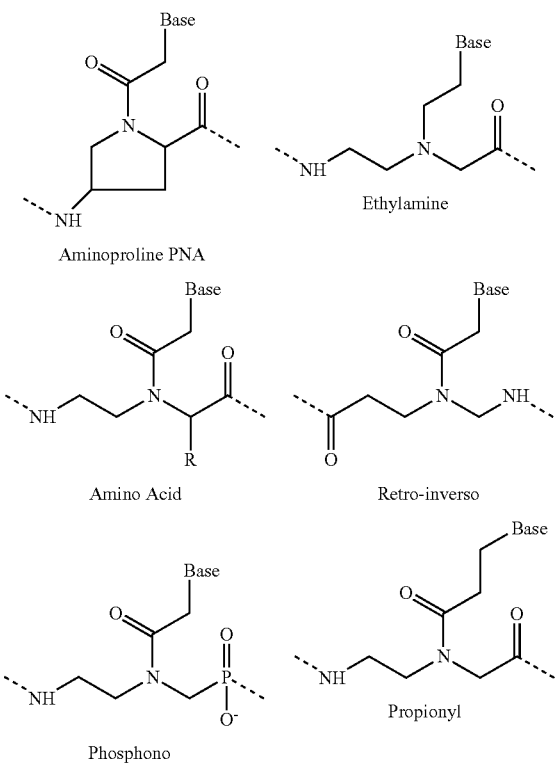

Aminoproline PNA
Ethylamine
Amino Acid
Retro-inverso
Phosphono
Propionyl

PNA can be modified by substitution of the glycine moiety of the PNA backbone with a chiral moiety. Therefore, in some forms, modified PNA monomers are chiral PNA monomers. The modification can be at the alpha (α), beta (β) or gamma (γ) positions of the PNA monomer (see Formula IV). For example, the glycine moiety of the PNA backbone can be substituted by alanine (Nielsen et al., 1994).

Chemical structures of DNA, achiral PNA, and alpha, beta, and gamma-PNAs.

Formula IV

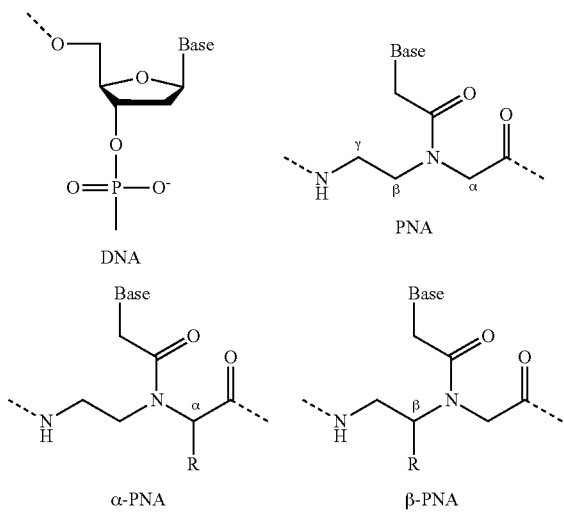

DNA
PNA
α-PNA
β-PNA

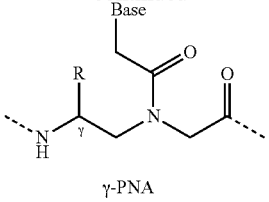

γ-PNA

Modified chiral monomers can be synthesized from L- or D-forms of chiral amino acids and incorporated into oligomers. Therefore, chiral PNA monomers can be in the form of L-PNA or D-PNA monomers (Sugiyama and Kitatta, 2013).

Different chiral isoforms of PNA monomers can have distinct functional properties. Therefore, the thermal stability of a PNA-DNA duplex containing D-form or L-form PNA monomers can be the same as, similar or different to that of the original PNA with a glycine backbone. For example, the thermal stability of a PNA-DNA duplex containing D-form monomers can be similar to that of the original PNA with a glycine backbone, whereas the thermal stability of a PNA-DNA duplex containing L-form monomers can be reduced relative to a PNA-DNA duplex containing the original PNA.

(C) Modifications of PNA Charge

Chemical substitutions at the backbone of PNA monomers can introduce negative or positive charges. For example, PNA having positively charged side-chains shows higher selectivity with DNA, while PNA having negatively charged side-chains shows higher selectivity with RNA (De Costa & Heemstra, 2013, 2014).

Charged moieties can be introduced to defined positions in PNA probes. For example, the modification can be at the alpha (α), beta (β) or gamma (γ) positions of the PNA monomer (see chemical structures of Formula IV). In some forms the net charge of the backbone is the prevailing factor influencing duplex stability as a function of ionic strength. In some forms, charge-modified PNA strands provide sufficient local perturbation to account for the observed differences in selectivity. For example, aspartic acid and lysine monomers have slightly different side chain lengths, with the lysine placing the charged atom two carbons farther away from the PNA backbone relative to the aspartic acid (De Costa & Heemstra, 2014).

PNA probes including chiral PNA with modifications of the backbone introducing a positive charge (for example, gamma-Lysine) have improved double-stranded DNA invasion properties due to induction of helical pre-organization in the polyamide backbone, as well as electrostatic interactions with the negatively charged backbone of natural DNA. Thus, PNA probes designed to include charge-modified PNAs show superior binding selectivity with DNA as compared to equivalent, unmodified PNA strands. Therefore, in some forms, PNA probes include one or more PNA monomers with modifications of the backbone introducing a charge.

PNA duplex stability with DNA or RNA targets can vary with changes in salt concentrations. At low salt concentrations, positively charged PNA probes bind more strongly to DNA and RNA than do negatively charged PNA probes. However, at medium to high salt concentrations, this trend is reversed, and negatively charged PNA probes show higher affinity for DNA and RNA than do positively charged PNA probes. Thus, charge screening by counter ions in solution enables negatively charged side chains to be incorporated into the PNA backbone without reducing duplex stability with DNA and RNA. Thus, introduction of negatively charged side chains, such as aspartic acid, is not significantly detrimental to PNA binding affinity at physiological ionic strength and PNA probes can be designed to incorporate a negative charge without reducing binding affinity.

Sequence-selectivity for charge modified PNAs having positively or negatively charged gamma side chains can be directly compared using any means known in the art. For example, circular dichroism (CD) studies can reveal whether side chain modifications significantly alter the overall structure of the PNA:DNA duplexes.

In some forms PNA probes include PNA monomers modified by the addition of a chiral charged side-chain at the gamma (γ) position (γ-PNA) (Formula V).

chiral PNA containing a charged group modification (R) in the gamma position of the backbone (De Costa & Heemstra, 2013).

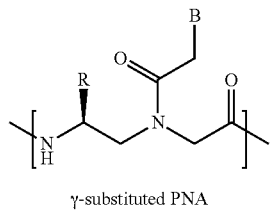

Formula V

γ-substituted PNA

The first gamma-chiral PNA monomer was reported in 1994, and oligomers carrying γ-chiral units was reported in 2005 (Tedeschi et al., 2005, Englund et al., 2005). Spectroscopic studies of serine- or alanine-based γ-PNAs established that gamma-backbone modification pre-organize single-stranded PNA oligomers into a right-handed helical structure that is very similar to that of PNA-DNA duplex (Dragulescu, et al (2006)). Helical induction is sterically driven and stabilized by base stacking. Thus, gamma-PNAs can bind DNA with very high affinity and high sequence selectivity. For example, a fully gamma-modified decameric PNA formed an exceptionally stable PNA-DNA duplex with an increase of 19° C. of the melting temperature compared to the unmodified PNA (Dragulescu, et al (2006)). The crystal structure of a PNA-DNA duplex with complete gamma-backbone modification of the PNA illustrates that gamma-PNA possesses conformational flexibility while maintaining sufficient structural integrity to adopt the P-helical conformation on hybridization with DNA (Yeh, et al., 2010). Gamma-PNAs in the single-strand state (determined by NMR) and in the hybrid duplex state (determined by X-ray crystallography) adopt a very similar conformation.

Thus, it is possible to use PNA molecules with chiral backbones to target double stranded DNA for strand invasion mediated by Watson-Crick base paring, not depended on the formation of DNA triplex structures. For example, gamma-PNAs with a length of 15-20 nucleotides were shown to invade duplex DNA without the need to attach any ancillary agents to PNAs (He et al., 2009).

Exemplary PNA monomers that are charged at neutral pH are PNA monomers modified by the addition of a positively-charged side-chain lysl ($(CCH_2)_4NH_2$) group (i.e., a lysine side-chain), or a thialysine side chain. In some forms the lysine side-chain is added at the gamma position of the PNA backbone (gamma-lysine). The preferred lysine isomer at the gamma position for optimal PNA:DNA hybrid stability is the L-isomer (i.e., Gamma-L-Lysine PNA Formula VI).

Chemical structure of chiral PNA containing a gamma-L-lysine modification in the backbone. "B" in the PNA unit denotes a nucleobase.

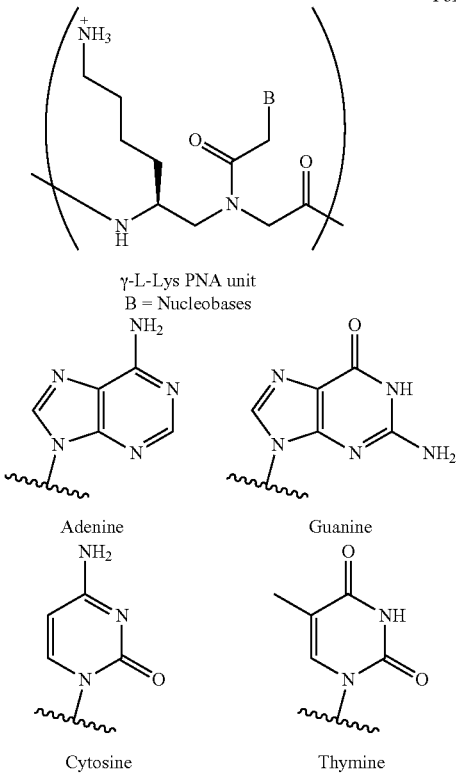

Formula VI

γ-L-Lys PNA unit
B = Nucleobases

Adenine  Guanine

Cytosine  Thymine

The chirality of the side-chain moiety can influence the structure of the PNA. For example, for gamma-lysine-PNA, the side chain with L configuration is oriented along the periphery of the duplex whereas the D configuration is directed to the interior of the duplex.

In some forms, charged PNA monomers are PNA monomers modified with alpha-Lysine. A D-Lysine isomer at the alpha position yields stable PNA:DNA hybrids, but forms a PNA-like helical structure with 16 residues per turn (i.e., alpha-D-lysine PNA; Formula VI).

Chemical structure of chiral PNA containing an alpha-D-lysine modification in the backbone.

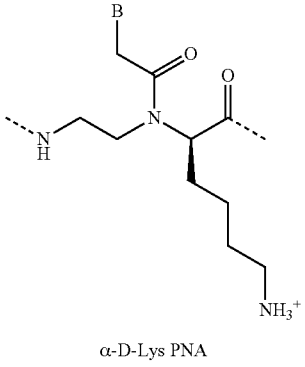

Formula VII

α-D-Lys PNA

In forms utilizing alpha-D-Lysine, the simultaneous use, in the same PNA probe molecule, of chiral PNA monomers with short chain oligo ethylene glycols preferably uses this modification in the alpha position of the PNA backbone, in order to be compatible with the chiral alpha-Lysine.

Preferred charged amino acid side chains include gamma-L-Lysine and gamma-L-thialysine (also known as S-aminoethyl-L-cysteine or thiosine or Aminoethylcysteine). L-thialysine is a toxic analog of the amino acid lysine, in which the second carbon of the amino acid R-group (side chain) is substituted with a sulfur atom.

Chemical structure of L-thialysine

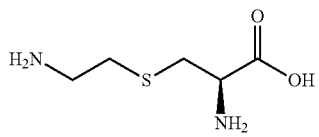

Formula VIII

A key property of L-thialysine is that the pK of the amino R-group is approximately 9.5, as opposed to approximately 10.5 for lysine. The lower pK of L-thialysine can be of utility in devising a more efficient elution method. By utilizing a buffer capable of maintaining the pH at 9.75 during the elution step, it is possible to obtain release of the captured DNA molecules at a lower temperature than that required for release of the equivalent DNA molecules captured using a buffer capable of maintaining the pH at or above 10.5. This is the case because the L-thialysine moieties in the PNA probe undergo de-protonation at pH 9.75, losing their positive charge, with consequent weakening of ionic interactions that stabilize PNA probe binding to the negatively charged DNA backbone.

(D) Gamma-MiniPEG Backbone Modifications of PNA

In some forms PNA probes include PNA with chiral modifications of the backbone introducing neural, uncharged mini-Polyethylene-glycol (PNA-Mini-PEG) (Formula IX).

Typically, the mini-PEG modification includes a short-chain oligo-ethylene glycol. Exemplary oligo-ethylene glycols include di-ethylene glycol, tri-ethylene glycol, tetra-ethylene glycol, penta-ethylene glycol, hexa-ethylene glycol, etc.

Repeating unit of a short chain oligo-ethylene glycol (n = 1-6).

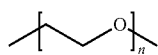

Formula IX

PNA-Mini-PEG monomers induce helical pre-organization in the polyamide backbone. Therefore, PNA probes including PNA-Mini-PEG monomers have improved double-strand DNA invasion properties. For example, Gamma-PNA probes with a length of 15-20 nucleotides were shown to invade duplex DNA without the need to attach any ancillary agents to PNAs (He et al., 2009). Short polyethylene glycol (Mini-PEG)-containing gamma-PNA was reported that possessed further improved DNA binding properties by reducing non-specific binding to mismatched sequences (Bahal, et al., 2012) (see Formula X).

Chemical structure of chiral PNA containing a neutral gamma-Mini-PEG modification in the backbone.

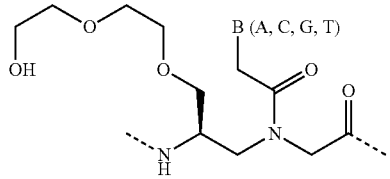

Formula X

Practical applications of chiral PNA probes with gamma-MiniPEG modifications of the backbone have been reported in the field of antisense inhibition of transcription of the CCR5 gene (Bahal et al., 2013) as well as in the field of genome editing to correct genetic defects (Bahal et. al., 2014). In spite of these advances, the most recent review on the applications of chiral PNA (Sugiyama et al., 2013) fails to mention any potential applications of these chiral PNA molecules for DNA enrichment by sequence capture.

Typically, the mini-PEG modification includes a short-chain oligo-ethylene glycol. Exemplary oligo-ethylene glycols include di-ethylene glycol, tri-ethylene glycol, tetra-ethylene glycol, penta-ethylene glycol, hexa-ethylene glycol, etc.

Useful PNA probes include PNA modified to include chiral backbone modifications, for example, chiral backbone modifications at the gamma-position. In some forms the modification introduces a positive charge. The PNA probes can also include residues having a backbone modified by a neutral oligomeric moiety, such as a short-chain oligo-ethylene glycol. A preferred short-chain oligoethylene moiety is diethylene glycol.

iii. Capture Tags

The disclosed PNA hybridization probes can include one or more capture tags. A capture tag is any compound that can be used to separate compounds or complexes having the capture tag from those that do not. Preferably, a capture tag is a compound, such as a ligand or hapten, which binds to or interacts with another compound, such as ligand-binding molecule or an antibody. It is also preferred that such interaction between the capture tag and the capturing component be a specific interaction, such as between a hapten and an antibody or a ligand and a ligand-binding molecule.

Preferred capture tags, described in the context of nucleic acid probes, are described by Syvnen et al., Nucleic acids Res., 14:5037 (1986). A preferred capture tag is biotin, which can be incorporated into nucleic acids.

In the disclosed method, capture tags incorporated into adaptor-indexers or second adaptors can allow sample fragments (to which the adaptors have been coupled) to be captured by, adhered to, or coupled to a substrate. Such capture allows simplified washing and handling of the fragments, and allows automation of all or part of the method.

Capturing sample fragments on a substrate may be accomplished in several ways. In some forms, capture docks are adhered or coupled to the substrate. Capture docks are compounds or moieties that mediate adherence of a sample fragment by binding to, or interacting with, a capture tag on the fragment. Capture docks immobilized on a substrate allow capture of the fragment on the substrate. Such capture provides a convenient means of washing away reaction components that might interfere with subsequent steps.

Substrates for use in the disclosed method can include any solid material to which components of the assay can be adhered or coupled. Examples of substrates include, but are not limited to, materials such as acrylamide, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, woven fibers, shaped polymers, particles and microparticles. Some forms of substrates are plates and beads. A useful form of beads is magnetic beads.

In some forms, the capture dock is an oligonucleotide. Methods for immobilizing and coupling oligonucleotides to substrates are well established. For example, suitable attachment methods are described by Pease et al., Proc. Natl. Acad. Sci. USA 91(11):5022-5026 (1994), and Khrapko et al., Mol Biol (Mosk) (USSR) 25:718-730 (1991). A method for immobilization of 3'-amine oligonucleotides on casein-coated slides is described by Stimpson et al., Proc. Natl. Acad. Sci. USA 92:6379-6383 (1995). A preferred method of attaching oligonucleotides to solid-state substrates is described by Guo et al., Nucleic acids Res. 22:5456-5465 (1994).

In some forms, the capture dock is the anti-hybrid antibody. Methods for immobilizing antibodies to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in Protein immobilization: fundamentals and applications, Richard F. Taylor, ed. (M. Dekker, New York, 1991), Johnstone and Thorpe, Immunochemistry In Practice (Blackwell Scientific Publications, Oxford, England, 1987) pages 209-216 and 241-242, and Immobilized Affinity Ligands, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

iv. Labels

Any of the PNA molecules and PNA hybridization probes described can routinely be labelled. PNA probes are compatible with a wide range of reporter molecules. For example, to aid in detection and quantitation of ligator-detectors coupled to detector probes, labels can be incorporated into, coupled to, or associated with, ligator-detectors, detector probes, and/or adaptor-indexers. It is preferred that the ligator-detector be labeled. A label is any molecule that can be associated with ligator-detectors, directly or indirectly, and which results in a measurable, detectable signal, either directly or indirectly. A label is associated with a component when it is coupled or bound, either covalently or non-covalently, to the component. A label is coupled to a component when it is covalently coupled to the component. Many suitable labels for incorporation into, coupling to, or association with nucleic acid are known. Examples of labels suitable for use in the disclosed method are radioactive isotopes, fluorescent molecules, phosphorescent molecules, bioluminescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are a useful form of label since they can be directly incorporated into ligator-detectors during synthesis. Examples of labels that can be incorporated into DNA or RNA include nucleotide analogs such as BrdUrd (Hoy and Schimke, Mutation Research 290:217-230 (1993)), BrUTP (Wansick et al., J. Cell Biology 122:283-293 (1993)) and nucleotides modified with biotin (Langer et al., Proc. Natl. Acad. Sci. USA 78:6633 (1981)) or with suitable haptens such as digoxygenin (Kerkhof, Anal. Biochem. 205:359-364 (1992)). Suitable fluorescence-labeled nucleotides are Fluorescein-isothiocyanate-dUTP, Cyanine-3-dUTP and Cyanine-5-dUTP (Yu et al., Nucleic acids Res., 22:3226-3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringer Mannheim). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo[3.3.1.1$^{3,7}$]decane]-4-yl)phenyl phosphate; Tropix, Inc.).

Other labels include molecular or metal barcodes, mass labels, and labels detectable by nuclear magnetic resonance, electron paramagnetic resonance, surface enhanced raman scattering, surface plasmon resonance, fluorescence, phosphorescence, chemiluminescence, resonance raman, microwave, or a combination. Mass labels are compounds or moieties that have, or which give the labeled component, a distinctive mass signature in mass spectroscopy. Mass labels are useful when mass spectroscopy is used for detection. Preferred mass labels are peptide nucleic acids and carbohydrates. Combinations of labels can also be useful. For example, color-encoded microbeads having, for example, 265 unique combinations of labels, are useful for distinguishing numerous components. For example, 256 different ligator-detectors can be uniquely labeled and detected allowing mutiplexing and automation of the disclosed method.

Useful labels are described in de Haas, R. R., et al., "Platinum porphyrins as phosphorescent label for time-resolved microscopy," *J. Histochem. Cytochem.* 45(9):1279-92 (1997); Karger and Gesteland, "Digital chemiluminescence imaging of DNA sequencing blots using a charge-coupled device camera," *Nucleic acids Res.* 20(24):6657-65 (1992); Keyes, R. S., et al., "Overall and internal dynamics of DNA as monitored by five-atom-tethered spin labels," *Biophys. J.* 72(1):282-90 (1997); Kirschstein, S., et al., "Detection of the DeltaF508 mutation in the CFTR gene by means of time-resolved fluorescence methods," *Bioelectrochem. Bioenerg.* 48(2):415-21 (1999); Kricka, L. J., "Selected strategies for improving sensitivity and reliability of immunoassays," *Clin. Chem.* 40(3):347-57 (1994); Kricka, L. J., "Chemiluminescent and bioluminescent techniques," *Clin. Chem.* 37(9):1472-81 (1991); Kumke, M. U., et al., "Temperature and quenching studies of fluorescence polarization detection of DNA hybridization," *Anal. Chem.* 69(3):500-6 (1997); McCreery, T., "Digoxigenin labeling," *Mol. Biotechnol.* 7(2):121-4 (1997); Mansfield, E. S., et al., "Nucleic acid detection using non-radioactive labeling methods," *Mol. Cell Probes* 9(3):145-56 (1995); Nurmi, J., et al., "A new label technology for the detection of specific polymerase chain reaction products in a closed tube," *Nucleic acids Res.* 28(8):28 (2000); Oetting, W. S., et al. "Multiplexed short tandem repeat polymorphisms of the Weber 8A set of markers using tailed primers and infrared fluorescence detection," *Electrophoresis* 19(18):3079-83 (1998); Roda, A., et al., "Chemiluminescent imaging of enzyme-labeled probes using an optical microscope-video-camera luminograph," *Anal. Biochem.* 257(1):53-62 (1998); Siddiqi, A., et al., "Evaluation of electrochemiluminescence- and bioluminescence-based assays for quantitating specific DNA," *J. Clin. Lab. Anal.* 10(6):423-31 (1996); Stevenson, C. L., et al., "Synchronous luminescence: a new detection technique for multiple fluorescent probes used for DNA sequencing," *Biotechniques* 16(6):1104-11 (1994); Vo-Dinh, T., et al., "Surface-enhanced Raman gene probes," *Anal. Chem.* 66(20):3379-83 (1994); Volkers, H. H., et al., "Microwave label detection technique for DNA in situ hybridization," *Eur. J. Morphol.* 29(1):59-62 (1991).

Metal barcodes, a form of molecular barcode, are 30-300 nm diameter by 400-4000 nm multilayer multi metal rods. These rods are constructed by electrodeposition into an alumina mold, then the alumina is removed leaving these small multilayer objects behind. The system can have up to 12 zones encoded, in up to 7 different metals, where the metals have different reflectivity and thus appear lighter or darker in an optical microscope depending on the metal; this leads to practically unlimited identification codes. The metal bars can be coated with glass or other material, and probes attached to the glass using methods commonly known in the art; assay readout is by fluorescence from the target, and the identity of the probe is from the light dark pattern of the barcode.

Methods for detecting and measuring signals generated by labels are known. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. Such methods can be used directly in the disclosed method of amplification and detection. As used herein, detection molecules are molecules which interact with amplified nucleic acid and to which one or more detection labels are coupled. In some forms of detection, labels can be distinguished temporally via different fluorescent, phosphorescent, or chemiluminescent emission lifetimes. Multiplexed time-dependent detection is described in Squire et al., J. Microscopy 197(2):136-149 (2000), and WO 00/08443.

Quantitative measurement of the amount or intensity of a label can be used. For example, quantitation can be used to determine if a given label, and thus the labeled component, is present at a threshold level or amount. A threshold level or amount is any desired level or amount of signal and can be chosen to suit the needs of the particular form of the method being performed.

v. Amino Acid and Peptide Adducts

In some forms, amino acids can be added to the termini of the PNA hybridization probes. Addition of one or more amino acid residues to the termini of PNA hybridization probes can impart structural and functional characteristics to the PNA probes, including thermal stability, aqueous solubility, ligand-binding affinity and combinations thereof. Naturally-occurring amino acids, non-naturally occurring amino acids, and combinations thereof can be incorporated onto one or both termini of the PNA probes using any technique known in the art. Therefore, PNA probes including naturally-occurring and non-naturally occurring amino acids are described. Preferably, the addition of amino acids at one or both termini of the PNA does not reduce or otherwise negatively impact the specificity or affinity of the probe.

In some forms hydrophilic amino acid residues incorporated to increase the hydrophilicity or solubility of the probe, or to reduce undesirable hydrophobic interactions. For example, addition of one, two or more than two lysine residues at either terminus of a PNA probe can enhance the aqueous solubility of the probe relative to an equivalent unmodified probe. Therefore, in some forms, PNA hybridization probes include terminal poly-lysine adducts.

In some forms, amino acid adducts can be included to assist affinity capture. Exemplary adducts include one or more repeats of histidine residues. Poly-histidine motifs, such as $His_6$ tags, can facilitate PNA capture using nickel-NTA with very high efficacy, while maintaining efficient single base pair discrimination.

vi. PNA Hybridization Probe Composition

Examples of alternative PNA probe compositions for DNA capture by invasion of double-stranded DNA according to this invention are provided in Table 2. This is not an exhaustive list, but rather a sampling of the range of possible designs that can be used as PNA capture probes according to this invention.

Combinations of multiple PNA modifications within a probe can enhance DNA capture by invasion of double-stranded DNA. "Probe performance", as determined by overall yield of enriched target DNA, can be related to hybridization, for example, the specificity and/or affinity of a probe for a specific nucleic acid sequence. Therefore, factors that influence inter-molecular interactions between the probe and the corresponding nucleic acid can influence probe performance, including probe conformation, probe size and relative charge.

a. Chirality

PNA probes can include both chiral and non-chiral PNA residues. Preferred PNA probes include chiral PNA monomers in an amount and configuration effective to promote DNA strand invasion. For example, PNA probes can include chiral, charged PNA monomer units that prevent formation of a PNA/PNA duplex by destabilizing PNA/PNA duplexes, stabilize PNA/DNA duplexes, or both.

The probes can include alternating units of chiral and non-chiral residues. It may be that the chirality of PNA residues within a PNA probe results in changes in the conformation of the entire probe, or localized changes within one or more regions of a probe. Therefore, in some forms, PNA probes having alternative chiral backbones can bind to target nucleic acids with different modes of interaction throughout the probe and provide higher performance than equivalent, non-chiral probes. Preferred PNA probes include at least one chiral PNA residues, more preferably two or more chiral residues.

In some forms, the performance of a PNA probe can depend upon the relative content of chiral PNA residues and non-chiral PNA residues within the probe. As used herein, a chiral PNA residue is a residue in which the alpha, beta, or gamma carbon is derivatized (thus making the derivatized carbon a chiral center). For example, the number of chiral residues relative to non-chiral residues can influence the ability of a probe to bind a target with high specificity and appropriate affinity, amenable for use with the described methods. Therefore, in some forms, the chirality of the residues in a PNA probe with respect to the alpha carbon, beta carbon, delta or gamma carbon can be the same or different for consecutive PNA residues. PNA probes can be designed having residues that have contiguous residues with alternating chirality, or groups of residues having regular differences in chirality. In some forms, PNA probes include chiral residues every residue, or every other residue, or every third residue, every fourth reside, every fifth residue, every sixth residue, every seventh residue, every eighth residue, or every ninth residue. In some forms, optimal strand invasion is achieved using PNA probes where the residues derivatized on the gamma carbon with a moiety alternate every second residue (i.e., 50% derivatized) or every third residue (i.e., 33% derivatized). In some forms, fewer modifications than every third residue result in reduced probe performance. Typically, the performance of probes where the gamma-derivatized residues alternate every second position in the backbone is as good, or better than when gamma-derivatized residues are used at every position (i.e., 100% chiral). Preferred chiral PNA residues include residues derivatized at the gamma carbon, for example, by addition of an amino acid side-chain, or by addition of a miniPEG moiety.

b. Probe Size and Relative Charge

Generally, PNA probes include linear oligomers of between 6 and 26 contiguous PNA residues, inclusive. Typically, the probes have at least two residues modified with a charged side-chain. Exemplary charged groups include the side-chains of amino acid residues such as lysine, thialysine, arginine, glutamic acid, aspartic acid, and derivatives and variants thereof. Preferred charged amino acids include lysine, thialysine and derivatives thereof. In some forms, PNA hybridization probes include at least two gamma-lysine or thialysine modifications to reduce PNA-PNA interactions. Preferred probes include less than 7 charged chiral gamma backbone modifications, introducing no more than 7 positive charges in a 20-base PNA probe. These probes can be used successfully for DNA capture, as they do not give rise to non-specific DNA binding artefacts. Therefore, in some forms, PNA probes include at least two residues modified by addition of a charged moiety at the gamma-carbon, preferably 3-5 lysines. In some forms, probes having more than 6 charged residues have lower performance than those having less than 6 charged residues, such as 2, 3, 4, or 5 charged residues.

Highly-charged probes (e.g. probes having 7 or more gamma-L-Lysine backbone modifications, introducing 7 or more positive charges in a 20-base PNA probe) can be used successfully for DNA capture, but are less preferred, as they sometimes show non-specific DNA binding artefacts. Therefore, in some forms, PNA hybridization probes contain a ratio of less than 7 positive charges for every 20 residues. In some forms, the number of non-charged residues is approximately one third of the total number of residues. Regardless of the total number of residues within a PNA probe, the relative proportion of charged derivatives is generally between 10% and 50%, such as between 10% and 40%, for example, between 11.5% and 37.5%, between 15% and 40%, 15%, 15.4%, 18.8%, 19.2%, 20%, 23.1%, 25%, 30%, 31% or 33.3%. A preferred range for the percentage of charged moieties (e.g., % charged PNA residues) within a given PNA probe is between 15% and 45%, more preferably between 15% and 35%, for example between 15% to 25%, inclusive.

The probes provided in Table 2, combine gamma Mini-PEG modifications and gamma L-Lysine modifications. These probes have good solubility, rapid hybridization kinetics, and high melting temperature after DNA hybridization, as well as good mismatch discrimination.

Generally, probe performance is also a function of the efficacy of release from the target DNA following capture. Therefore, because the melting temperature of the PNA: DNA hybrid is proportional to the overall strength of the interaction, probes that bind with less affinity and are slightly less-efficient in capture, are easier to release, and may more result in a greater yield of target DNA, and/or produce an enriched DNA sample having greater conservation of non-denatured dsDNA.

The positively-charged Lysine residues undergo charge repulsion when contacting other PNA molecules. For this reason, PNA probes with 2 or more gamma-L-Lysine modifications are less likely to undergo intermolecular hybridization associations with other probes of different sequence present in a mixture containing thousands of different PNA sequences, designed to invade different DNA targets.

The last 2 probes in Table 2, each with 19 consecutive gamma modifications in the backbone can work well for DNA capture, but the chemical synthesis yield is lower than for probes with 10 or fewer gamma modifications.

TABLE 2

Exemplary PNA probe compositions
for capture of long, double stranded DNA

| SEQ. ID NO. | PROBE |
|---|---|
| 1 | biotin-B-gkB-B-B-gkB-B-B-gkB-B-B-gkB-B-B-gkB-B-B-gkB-B-B-Lys-Lys |
| 2 | biotin-B-gkB-B-B-gkB-B-B-gkB-B-B-gPB-B-B-gkB-B-B-gkB-B-B-gkB-Lys-Lys |
| 3 | biotin-B-gkB-B-B-gPB-B-B-gkB-B-B-gkB-B-B-gkB-B-B-gPB-B-B-gkB-Lys-Lys |
| 4 | biotin-B-gkB-B-B-gPB-B-B-gkB-B-B-gPB-B-B-gkB-B-B-gPB-B-B-gkB-Lys-Lys |
| 5 | biotin-B-gkB-B-gPB-B-gPB-B-gkB-B-gPB-B-gPB-B-gkB-B-gPB-B-gPB-B-gkB-Lys-Lys |
| 6 | biotin-B-gPB-B-gkB-B-gPB-B-gPB-B-gPB-B-gkB-B-gPB-B-gPB-B-gkB-B-gPB-Lys-Lys |
| 7 | biotin-B-gPB-B-gPB-B-gkB-B-gPB-B-gPB-B-gPB-B-gPB-B-gkB-B-gPB-B-gPB-Lys-Lys |
| 8 | biotin-B-gPB-gPB-gPB-gPB-gkB-gPB-gPB-gPB-gPB-gPB-gPB-gPB-gkB-gPB-gPB-gPB-gPB-gPB-Lys-Lys |
| 9 | biotin-B-gPB-gPB-gPB-gPB-gPB-gPB-gPB-gPB-gPB-gPB-gPB-gPB-gPB-gPB-gPB-gPB-gPB-gPB-gPB-Lys-Lys |

B: any base, A, G, C, T or a base analog, such as D (2,6-diaminopurine) or others
Biotin: biotin chemical group
gkB: Base with gamma-Lysine backbone modification (in gamma-position)
gk: gamma Lysine backbone modification; introduces one positive charge; the gk monomers for synthesis of PNA (Huang et al., 2012)
gPB: Base with gamma-MiniPEG backbone modification (in gamma-position)
gP: gamma MiniPEG backbone modification; gP monomers for chemicals synthesis of PNA (Sahu et al., 2011)
PNA length: 20 bases
Lys-Lys: terminal Lysine dipeptide to increase solubility of PNA In some forms, the PNA probe is not composed solely of alpha-D-Lysine PNA residues with no other chiral PNA residues. In some forms, the PNA probe has more than 10 PNA residues. In some forms, the PNA probe is not composed solely of alpha-D-Lysine PNA residues with no other chiral PNA residues and has more than 10 PNA residues.

c. PNA Probe Optimization

Optimal composition can be customized to an application. For example, in some forms, when the goal is to obtain the maximum absolute yield of captured DNA sequences, 18 base PNA probes with 5 gamma-L-Lysine residues are preferred. In some forms, when the application demands not the highest yield but instead the highest enrichment (the highest possible ratio of target DNA relative to non-target DNA), preferred probes are those that generate a lower level of nonspecific sequence capture. Therefore, in some forms, 18-base PNA probes with only 4 gamma-L-Lysine residues are preferred.

In some forms of the probe, the PNA probe has at or between 10 to 26 peptide nucleic acid residues. In some forms of the probe, the PNA probe is designed to target a sequence in a nucleic acid fragment. In some forms of the probe, the PNA probe includes one or more peptide nucleic acid residues that are derivatized with a charged moiety on the alpha, beta, or gamma carbon or combinations thereof, and one or more peptide nucleic acid residues that are derivatized with or a neutral moiety on the alpha, beta, or gamma carbon, or combinations thereof. In some forms of the probe, the PNA probe includes one or more capture tags.

In some forms of the probe, the probe includes at or between 16 to 22 peptide nucleic acid residues. In some forms of the probe, the probe includes 18 or 19 peptide nucleic acid residues. In some forms of the probe, at or between three to five of the peptide nucleic acid residues are derivatized with the charged moieties, where the charged moieties are selected from the group consisting of gamma-L-lysine PNA, gamma-L-thialysine PNA, and combinations thereof, where at or between two to six of the peptide nucleic acid residues that are not derivatized with the charged moieties are derivatized with diethylene glycol, and where the capture tag is biotin. In some forms of the probe, four of the peptide nucleic acid residues are gamma-L-lysine PNA, where four of the peptide nucleic acid residues that are derivatized with diethylene glycol, and where the capture tag is biotin. In some forms of the probe, four of the peptide nucleic acid residues are gamma-L-thialysine PNA, where four of the peptide nucleic acid residues that are derivatized with diethylene glycol, and where the capture tag is biotin.

In some forms of the probe, independently at or between one to three peptide nucleic acid residues that are not derivatized with a charged moiety between every peptide nucleic acid residue that is derivatized with a charged moiety. In some forms of the probe, there is an average of at or between 1.0 to 5.0 peptide nucleic acid residues that are not derivatized with a charged moiety between every peptide nucleic acid residue that is derivatized with a charged moiety. In some forms of the probe, there are independently at or between zero to two peptide nucleic acid residues that are not derivatized with a moiety between every peptide nucleic acid residue that is derivatized with a moiety. In some forms of the probe, there is an average of at or between 0.5 to 1.5 peptide nucleic acid residues that are not derivatized with a moiety between every peptide nucleic acid residue that is derivatized with a moiety. In some forms of the probe, every peptide nucleic acid residue is derivatized with a moiety.

In some forms of the probe, the PNA probe includes (i) one or more peptide nucleic acid residues that are derivatized with a charged moiety on the alpha carbon, beta carbon, gamma carbon, or combinations thereof and (ii) one or more peptide nucleic acid residues that are derivatized with a neutral moiety on the alpha carbon, beta carbon, gamma carbon, or combinations thereof. In some forms of the probe, at or between 15% to 28% of the peptide nucleic acid residues of the PNA probe are derivatized with a charged moiety. In some forms of the probe, at or between 2 to 7 of the peptide nucleic acid residues of the PNA probe are derivatized with a charged moiety. In some forms of the probe, 3, 4, 5, or 6 of the peptide nucleic acid residues of the PNA probe are derivatized with a charged moiety. In some forms of the probe, 4 or 5 of the peptide nucleic acid residues of the PNA probe are derivatized with a charged moiety. In some forms of the probe, there are at least two peptide nucleic acid residues that are not derivatized with a charged moiety between every peptide nucleic acid residue that is derivatized with a charged moiety.

In some forms of the probe, one or more of the peptide nucleic acid residues that are derivatized with the charged moiety are independently derivatized with the charged moiety on the alpha, beta, or gamma carbon, or combinations thereof. In some forms of the probe, one or more of the peptide nucleic acid residues that are derivatized with the charged moiety are derivatized with the charged moiety on the gamma carbon. In some forms of the probe, all of the peptide nucleic acid residues that are derivatized with the charged moiety are derivatized with the charged moiety on the gamma carbon.

In some forms of the probe, one or more of the peptide nucleic acid residues that are derivatized with the charged moieties are L- or D-lysine peptide nucleic acid residues. In some forms of the probe, one or more of the peptide nucleic acid residues that are derivatized with the charged moieties are L-thialysine peptide nucleic acid residues. In some forms of the probe, all of the peptide nucleic acid residues that are derivatized with the charged moieties are L- or D-lysine peptide nucleic acid residues. In some forms of the probe, all of the peptide nucleic acid residues that are derivatized with the charged moieties are L-thialysine peptide nucleic acid residues. In some forms of the probe, one or more the peptide nucleic acid residues that are derivatized with the charged moieties are L-lysine peptide nucleic acid residues. In some forms of the probe, all of the peptide nucleic acid residues that are derivatized with the charged moieties are L-lysine peptide nucleic acid residues.

In some forms of the probe, at or between 4% to 85% of the peptide nucleic acid residues of the PNA probe are derivatized with a neutral moiety. In some forms of the probe, at or between 4% to 50% of the peptide nucleic acid residues of the PNA probe are derivatized with a neutral moiety. In some forms of the probe, at or between 4% to 35% of the peptide nucleic acid residues of the PNA probe are derivatized with a neutral moiety. In some forms of the probe, at or between 1 to 19 of the peptide nucleic acid residues of the PNA probe are derivatized with a neutral moiety. In some forms of the probe, at or between 1 to 15 of the peptide nucleic acid residues of the PNA probe are derivatized with a neutral moiety. In some forms of the probe, at or between 1 to 10 of the peptide nucleic acid residues of the PNA probe are derivatized with a neutral moiety. In some forms of the probe, 1, 2, 3, or 4 of the peptide nucleic acid residues of the PNA probe are derivatized with a neutral moiety. In some forms of the probe, 1 or 2 of the peptide nucleic acid residues of the PNA probe are derivatized with a neutral moiety.

In some forms of the probe, one or more of the peptide nucleic acid residues that are derivatized with a neutral moiety are derivatized on the alpha, beta, or gamma carbon. In some forms of the probe, all of the peptide nucleic acid residues that are derivatized with a neutral moiety are derivatized on the alpha, beta, or gamma carbon. In some forms of the probe, one or more of the peptide nucleic acid residues that are derivatized with a neutral moiety are derivatized on the gamma carbon. In some forms of the probe, all of the peptide nucleic acid residues that are derivatized with a neutral moiety are derivatized on the gamma carbon.

In some forms of the probe, one or more of the neutral moieties is a short-chain oligoethylene moiety. In some forms of the probe, all of the neutral moieties are short-chain oligoethylene moieties. In some forms of the probe, one or more of the short-chain oligoethylene moieties are diethylene glycol. In some forms of the probe, all of the short-chain oligoethylene moieties are diethylene glycol. In some forms of the probe, the capture tag is biotin or streptavidin.

In some forms of the probe, the PNA probe is derivatized with one or more amino acids on at least one of the terminal peptide nucleic acid residues. In some forms of the probe, the PNA probe is derivatized with two or more lysine residues on at least one of the terminal peptide nucleic acid residues. In some forms of the probe, one or more peptide nucleic acid residues have a pseudo-complementary nucleobase as the base moiety of the peptide nucleic acid residue. In some forms of the probe, the pseudo-complementary nucleobases are independently selected from the group consisting of pseudouridine (5-ribosyluracil); 7-Deaza-2'-deoxyguanosine; 2,6-Diaminopurine-2'-deoxyriboside; N4-Ethyl-2'-deoxycytidine; 2-thiothymidine; 2-aminoadenine; 2-aminopurine-riboside; 2,6-diaminopurine-riboside; 2'-deoxyisoguanosine; and 5-hydroxymethyl-2'-deoxycytidine.

The PNA probes are generally used together in sets of two or more PNA probes. In some forms of the set, the PNA probes in the same set of two or more PNA probes are designed to target a different sequence in the same nucleic acid fragment, where the PNA probes in different sets of two or more PNA probes are designed to target different nucleic acid fragments.

In some forms of the set, at least one of the PNA probes is a PNA probe as described herein. In some forms of the set, all of the PNA probes are independently PNA probes of any one of claims 11 to 49. In some forms of the set, at least one of the PNA probes includes (i) one or more peptide nucleic acid residues that are derivatized with a charged moiety on the alpha carbon, beta carbon, gamma carbon, or combinations thereof, (ii) one or more peptide nucleic acid residues that are derivatized with a neutral moiety on the alpha carbon, beta carbon, gamma carbon, or combinations thereof, or (iii) combinations thereof.

In some forms of the set, in one or more of the PNA probes there are independently at or between one to three peptide nucleic acid residues that are not derivatized with a charged moiety between every peptide nucleic acid residue that is derivatized with a charged moiety. In some forms of the set, in all of the PNA probes there are independently at or between one to three peptide nucleic acid residues that are not derivatized with a charged moiety between every peptide nucleic acid residue that is derivatized with a charged moiety. In some forms of the set, in one or more of the PNA probes there is an average of at or between 1.0 to 5.0 peptide nucleic acid residues that are not derivatized with a charged moiety between every peptide nucleic acid residue that is derivatized with a charged moiety. In some forms of the set, in all of the PNA probes there is an average of at or between 1.0 to 5.0 peptide nucleic acid residues that are not derivatized with a charged moiety between every peptide nucleic acid residue that is derivatized with a charged moiety.

In some forms of the set, in one or more of the PNA probes there are independently at or between zero to two peptide nucleic acid residues that are not derivatized with a moiety between every peptide nucleic acid residue that is derivatized with a moiety. In some forms of the set, in all of the PNA probes there are independently at or between zero to two peptide nucleic acid residues that are not derivatized with a moiety between every peptide nucleic acid residue that is derivatized with a moiety. In some forms of the set, in one or more of the PNA probes there is an average of at or between 0.5 to 1.5 peptide nucleic acid residues that are not derivatized with a moiety between every peptide nucleic acid residue that is derivatized with a moiety. In some forms of the set, in all of the PNA probes there is an average of at or between 0.5 to 1.5 peptide nucleic acid residues that are not derivatized with a moiety between every peptide nucleic acid residue that is derivatized with a moiety.

In some forms of the set, one or more of the PNA probes independently include at or between two to six peptide nucleic acid residues that independently are derivatized with the charged moiety on the alpha, beta, or gamma carbon. In some forms of the set, one or more of the PNA probes independently include at or between three to five peptide nucleic acid residues that independently are derivatized with the charged moiety on the alpha, beta, or gamma carbon. In some forms of the set, all of the PNA probes independently include at or between two to six peptide nucleic acid residues that independently are derivatized with the charged moiety on the alpha, beta, or gamma carbon. In some forms of the set, all of the PNA probes independently include at or between three to five peptide nucleic acid residues that independently are derivatized with the charged moiety on the alpha, beta, or gamma carbon.

In some forms of the set, independently in one or more of the PNA probes one or more of the peptide nucleic acid residues that are derivatized with the charged moiety are derivatized with the charged moiety on the gamma carbon. In some forms of the set, in one or more of the PNA probes all of the peptide nucleic acid residues that are derivatized with the charged moiety are derivatized with the charged moiety on the gamma carbon. In some forms of the set, in all of the PNA probes one or more of the peptide nucleic acid residues that are derivatized with the charged moiety are derivatized with the charged moiety on the gamma carbon. In some forms of the set, in all of the PNA probes all of the peptide nucleic acid residues that are derivatized with the charged moiety are derivatized with the charged moiety on the gamma carbon.

In some forms of the set, in one or more of the PNA probes one or more of the peptide nucleic acid residues that are derivatized with the charged moieties are L- or D-lysine peptide nucleic acid residues. In some forms of the set, in one or more of the PNA probes one or more of the peptide nucleic acid residues that are derivatized with the charged moieties are L-thialysine peptide nucleic acid residues. In some forms of the set, in one or more of the PNA probes all of the peptide nucleic acid residues that are derivatized with the charged moieties are L- or D-lysine peptide nucleic acid residues. In some forms of the set, in one or more of the PNA probes all of the peptide nucleic acid residues that are derivatized with the charged moieties are L-thialysine peptide nucleic acid residues. In some forms of the set, in one or more of the PNA probes one or more of the peptide nucleic acid residues that are derivatized with the charged moieties are L-lysine peptide nucleic acid residues. In some forms of the set, in one or more of the PNA probes all of the peptide nucleic acid residues that are derivatized with the charged moieties are L-lysine peptide nucleic acid residues. In some forms of the set, in all of the PNA probes one or more of the peptide nucleic acid residues that are derivatized with the charged moieties are L- or D-lysine peptide nucleic acid residues. In some forms of the set, in all of the PNA probes one or more of the peptide nucleic acid residues that are derivatized with the charged moieties are L-thialysine peptide nucleic acid residues. In some forms of the set, in all of the PNA probes all of the peptide nucleic acid residues that are derivatized with the charged moieties are L- or D-lysine peptide nucleic acid residues. In some forms of the set, in all of the PNA probes all of the peptide nucleic acid residues that are derivatized with the charged moieties are L-thialysine peptide nucleic acid residues. In some forms of the set, in all of the PNA probes one or more of the peptide nucleic acid residues that are derivatized with the charged moieties are L-lysine peptide nucleic acid residues. In some forms of the set, in all of the PNA probes all of the peptide nucleic acid residues that are derivatized with the charged moieties are L-lysine peptide nucleic acid residues.

In some forms of the set, one or more of the PNA probes independently include one or more peptide nucleic acid residues that are derivatized with a short-chain oligoethylene moiety on the alpha, beta, or gamma carbon. In some forms of the set, one or more of the PNA probes independently include at or between one to nineteen peptide nucleic acid residues that independently are derivatized with the short-chain oligoethylene moiety on the alpha, beta, or gamma carbon. In some forms of the set, all of the PNA probes independently include at or between one to nineteen peptide nucleic acid residues that independently are derivatized with the short-chain oligoethylene moiety on the alpha, beta, or gamma carbon. In some forms of the set, independently in one or more of the PNA probes one or more of the peptide nucleic acid residues that are derivatized with the short-chain oligoethylene moiety are derivatized with the short-chain oligoethylene moiety on the gamma carbon. In some forms of the set, in one or more of the PNA probes all of the peptide nucleic acid residues that are derivatized with the short-chain oligoethylene moiety are derivatized with the short-chain oligoethylene moiety on the gamma carbon. In some forms of the set, in all of the PNA probes one or more of the peptide nucleic acid residues that are derivatized with the short-chain oligoethylene moiety are derivatized with the short-chain oligoethylene moiety on the gamma carbon. In some forms of the set, in all of the PNA probes all of the peptide nucleic acid residues that are derivatized with the short-chain oligoethylene moiety are derivatized with the short-chain oligoethylene moiety on the gamma carbon.

In some forms of the set, in one or more of the PNA probes one or more of the short-chain oligoethylene moieties are diethylene glycol. In some forms of the set, in one or more of the PNA probes all of the short-chain oligoethylene moieties are diethylene glycol. In some forms of the set, in all of the PNA probes one or more of the short-chain oligoethylene moieties are diethylene glycol. In some forms of the set, in all of the PNA probes all of the short-chain oligoethylene moieties are diethylene glycol.

In some forms of the set, one or more of the PNA probes independently include one or more peptide nucleic acid residues having a pseudo-complementary nucleobase as the base moiety of the peptide nucleic acid residue. In some forms of the set, one or more of the PNA probes independently include at or between one to twenty-two peptide nucleic acid residues having a pseudo-complementary nucleobase as the base moiety of the peptide nucleic acid residue. In some forms of the set, all of the PNA probes independently include at or between one to twenty-two peptide nucleic acid residues having a pseudo-complementary nucleobase as the base moiety of the peptide nucleic acid residue. In some forms of the set, the pseudo-complementary nucleobases are independently selected from the group consisting of pseudouridine (5-ribosyluracil); 7-Deaza-2'-deoxyguanosine; 2,6-Diaminopurine-2'-deoxyriboside; N4-Ethyl-2'-deoxycytidine; 2-thiothymidine; 2-aminoadenine; 2-aminopurine-riboside; 2,6-diaminopurine-riboside; 2'-deoxyisoguanosine; and 5-hydroxymethyl-2'-deoxycytidine. In some forms of the set, the one or more of the PNA probes including one or more peptide nucleic acid residues having a pseudo-complementary nucleobase as the base moiety of the peptide nucleic acid residue is a subset of the PNA probes in the one or more sets of PNA probes.

In some forms of the set, the subset of the PNA probes in the one or more sets of PNA probes includes a subset of the PNA probes in the one or more sets of PNA probes that are predicted to be capable of interacting with one or more of the other PNA probes in the one or more sets of PNA probes. In some forms of the set, the subset of the PNA probes in the one or more sets of PNA probes consists of a subset of the PNA probes in the one or more sets of PNA probes that are predicted to be capable of interacting with one or more of the other PNA probes in the one or more sets of PNA probes.

In some forms of the set, in one or more of the PNA probes, the capture tag is biotin or streptavidin. In some forms of the set, in all of the PNA probes, the capture tag is biotin or streptavidin.

In some forms of the set, one or more of the PNA probes are derivatized with one or more amino acids on at least one of the terminal peptide nucleic acid residues. In some forms of the set, one or more of the PNA probes are derivatized with two or more lysine residues on at least one of the terminal peptide nucleic acid residues.

In some forms of the set, one or more or all of the PNA probes target sequences in human genomic DNA located in the MHC region of chromosome 6. In some forms of the set, one or more or all of the PNA probes target sequences in human genomic DNA associated with one or more diseases or conditions or having a known correlation with development of one or more disease or conditions, where the diseases or conditions are selected from the group consisting of autoimmune diseases, diabetes, and the metabolic syndrome, and cancer. In some forms of the set, one or more or all of the PNA probes target sequences in human genomic DNA at different positions that map to a multiplicity of enhancer elements associated with disease risk for autoimmune diseases. In some forms of the set, one or more or all of the PNA probes target sequences in human genomic DNA at different positions that map to a multiplicity of enhancer elements associated with disease risk for diabetes and the metabolic syndrome. In some forms of the set, one or more or all of the PNA probes target sequences in human genomic DNA at different positions that map to a multiplicity of enhancer elements associated with the differentiation of different subsets of white blood cells. In some forms of the set, one or more or all of the PNA probes target sequences in human mitochondrial DNA. In some forms of the set, one or more or all of the PNA probes target sequences in dog mitochondrial DNA. In some forms of the set, one or more or all of the PNA probes target sequences in genomic DNA of one or more parasites selected from the group consisting of bacteria, archaea, fungi, protozoa, or mixtures thereof. In some forms of the set, one or more or all of the parasite is one or more species of bacteria present in human oral cavity, human airway, human urogenital tract, human blood, or human feces.

In any set, group, mixture, or collection of PNA probes, all or some of the PNA probes in the set, group, mixture, or collection can have a specified characteristic. That is, when a feature or characteristic of PNA probes are specified, all of the probes in a set group, mixture, or collection need not have the specified feature or characteristic. Generally, when a feature or characteristic is specified for a set, group, mixture, or collection of PNA probes, all or substantially all of the PNA probes will have the specified feature of characteristic. However, some fraction of the PNA probes can lack or have a different value for the specified feature or characteristic. For example, in any set, group, mixture, or collection of PNA probes, 80%, 81%, 82%, 83%, 84%, 85%, 86%, 88%, 89%, 90%, 91%, 92%, 93%, 94%, 95%, 96%, 97%, 98%, 99%, or 100% can have the specified feature or characteristic. Such diversity can be either by accident or design. This applies to any feature or characteristic, or combination of features and characteristics, of PNA probes.

In some forms of the PNA probes, the PNA probes can be characterized by, in combination, two or more of the disclosed features or characteristics. For example, a PNA probe can be characterized as having any two or more specific values, ranges, or both of residues in the PNA probe, residues derivatized with a moiety, residues derivatized with a charged moiety, residues derivatized with a neutral moiety, residues not derivatized with a moiety, average of the residues in the probe that are derivatized with a moiety, average of the residues in the probe that are derivatized with a charged moiety, average of the residues in the probe that are derivatized with a neutral moiety, average of the residues in the probe that are not derivatized with a moiety, flanking residues not derivatized with a moiety, flanking residues not derivatized with a charged moiety, flanking residues not derivatized with a neutral moiety, residues not derivatized with a moiety between every residue derivatized with a moiety, residues not derivatized with a charged moiety between every residue derivatized with a charged moiety, residues not derivatized with a neutral moiety between every residue derivatized with a neutral moiety, average of the residues not derivatized with a moiety between every residue derivatized with a moiety, average of the residues not derivatized with a charged moiety between every residue derivatized with a charged moiety, average of the residues not derivatized with a neutral moiety between every residue derivatized with a neutral moiety, percentage of residues in the probe that are derivatized with a moiety, percentage of residues in the probe that are derivatized with a charged moiety, percentage of residues in the probe that are derivatized with a neutral moiety, percentage of residues in the probe that are not derivatized with a moiety, percentage of residues in the probe that are not derivatized with a charged moiety, percentage of residues in the probe that are not derivatized with a neutral moiety. In is understood that such combinations are limited to features and values that are not inconsistent with each other.

For example, a PNA probe or set of PNA probes can be characterized by a combination of specific a values, ranges, or both of for example, residues in the PNA probe, residues derivatized with a charged moiety, and residues derivatized with a neutral moiety; residues in the PNA probe, residues derivatized with a charged moiety, residues derivatized with a neutral moiety, and residues not derivatized with a charged moiety between every residue derivatized with a charged moiety; residues in the PNA probe, residues derivatized with a charged moiety, residues derivatized with a neutral moiety, and average of the residues not derivatized with a charged moiety between every residue derivatized with a charged moiety; residues in the PNA probe, average of the residues in the probe that are derivatized with a charged moiety, and average of the residues in the probe that are derivatized with a neutral moiety; residues in the PNA probe, average of the residues in the probe that are derivatized with a charged moiety, average of the residues in the probe that are derivatized with a neutral moiety, and residues not derivatized with a charged moiety between every residue derivatized with a charged moiety; or residues in the PNA probe, average of the residues in the probe that are derivatized with a charged moiety, average of the residues in the probe that are derivatized with a neutral moiety, and average of the residues not derivatized with a charged moiety between every residue derivatized with a charged moiety.

In some forms of the PNA probes, there can be ten, eleven, twelve, thirteen, fourteen, fifteen, sixteen, seventeen, eighteen, nineteen, twenty, twenty-one, twenty-two, twenty-three, twenty-four, twenty-five, or twenty-six residues in the PNA probe. In some forms of the PNA probes, there can be eleven, twelve, thirteen, fourteen, fifteen, sixteen, seventeen, eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, eighteen, nineteen, twenty, twenty-one, twenty-two, twenty-three, twenty-four, or twenty-five residues in the PNA probe. In some forms of the PNA probes, there can be twelve, thirteen, fourteen, fifteen, sixteen, seventeen, eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, eighteen, nineteen, twenty, twenty-one, twenty-two, twenty-three, or twenty-four residues in the PNA probe. In some forms of the PNA probes, there can be thirteen, fourteen, fifteen, sixteen, seventeen, eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, eighteen, nineteen, twenty, twenty-one, twenty-two, or twenty-three residues in the PNA probe. In some forms of the PNA probes, there can be fourteen, fifteen, sixteen, seventeen, eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, eighteen, nineteen, twenty, twenty-one, or twenty-two residues in the PNA probe. In some forms of the PNA probes, there can be fifteen, sixteen, seventeen, eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, eighteen, nineteen, twenty, or twenty-one residues in the PNA probe. In some forms of the PNA probes, there can be sixteen, seventeen, eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, eighteen, nineteen, or twenty residues in the PNA probe. In some forms of the PNA probes, there can be seventeen, eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, eighteen, or nineteen residues in the PNA probe. In some forms of the PNA probes, there can be eighteen, nineteen, twenty, twenty-one, twenty-two, twenty-three, twenty-four, twenty-five, or twenty-six residues in the PNA probe. In some forms of the PNA probes, there can be ten, eleven, twelve, thirteen, fourteen, fifteen, sixteen, seventeen, or eighteen residues in the PNA probe. In some forms of the PNA probes, there can be eleven, twelve, thirteen, fourteen, fifteen, sixteen, seventeen, eighteen, nineteen, twenty, twenty-one, twenty-two, twenty-three, twenty-four, or twenty-five residues in the PNA probe. In some forms of the PNA probes, there can be twelve, thirteen, fourteen, fifteen, sixteen, seventeen, eighteen, nineteen, twenty, twenty-one, twenty-two, twenty-three, or twenty-four residues in the PNA probe. In some forms of the PNA probes, there can be thirteen, fourteen, fifteen, sixteen, seventeen, eighteen, nineteen, twenty, twenty-one, twenty-two, or twenty-three residues in the PNA probe. In some forms of the PNA probes, there can be fourteen, fifteen, sixteen, seventeen, eighteen, nineteen, twenty, twenty-one, or twenty-two residues in the PNA probe. In some forms of the PNA probes, there can be fifteen, sixteen, seventeen, eighteen, nineteen, twenty, or twenty-one residues in the PNA probe. In some forms of the PNA probes, there can be sixteen, seventeen, eighteen, nineteen, or twenty residues in the PNA probe. In some forms of the PNA probes, there can be seventeen, eighteen, or nineteen residues in the PNA probe. In some forms of the PNA probes, there can be eighteen or nineteen residues in the PNA probe. In some forms of the PNA probes, there can be eighteen residues in the PNA probe. In some forms of the PNA probes, there can be nineteen residues in the PNA probe.

In some forms of the PNA probes, there can be four, five, six, seven, eight, nine, ten, eleven, twelve, thirteen, fourteen, fifteen, sixteen, seventeen, eighteen, or nineteen residues derivatized with a moiety. In some forms of the PNA probes, there can be five, six, seven, eight, nine, ten, eleven, twelve, thirteen, fourteen, fifteen, sixteen, seventeen, eighteen, or nineteen residues derivatized with a moiety. In some forms of the PNA probes, there can be four, five, six, seven, eight, nine, ten, eleven, twelve, thirteen, fourteen, fifteen, sixteen, seventeen, or eighteen residues derivatized with a moiety. In some forms of the PNA probes, there can be six, seven, eight, nine, ten, eleven, twelve, thirteen, fourteen, fifteen, sixteen, seventeen, eighteen, or nineteen residues derivatized with a moiety. In some forms of the PNA probes, there can be four, five, six, seven, eight, nine, ten, eleven, twelve, thirteen, fourteen, fifteen, sixteen, or seventeen residues derivatized with a moiety. In some forms of the PNA probes, there can be seven, eight, nine, ten, eleven, twelve, thirteen, fourteen, fifteen, sixteen, seventeen, eighteen, or nineteen residues derivatized with a moiety. In some forms of the PNA probes, there can be four, five, six, seven, eight, nine, ten, eleven, twelve, thirteen, fourteen, fifteen, or sixteen residues derivatized with a moiety. In some forms of the PNA probes, there can be eight, nine, ten, eleven, twelve, thirteen, fourteen, fifteen, sixteen, seventeen, eighteen, or nineteen residues derivatized with a moiety. In some forms of the PNA probes, there can be four, five, six, seven, eight, nine, ten, eleven, twelve, thirteen, fourteen, or fifteen residues derivatized with a moiety. In some forms of the PNA probes, there can be nine, ten, eleven, twelve, thirteen, fourteen, fifteen, sixteen, seventeen, eighteen, or nineteen residues derivatized with a moiety. In some forms of the PNA probes, there can be four, five, six, seven, eight, nine, ten, eleven, twelve, thirteen, or fourteen residues derivatized with a moiety. In some forms of the PNA probes, there can be ten, eleven, twelve, thirteen, fourteen, fifteen, sixteen, seventeen, eighteen, or nineteen residues derivatized with a moiety. In some forms of the PNA probes, there can be four, five, six, seven, eight, nine, ten, eleven, twelve, or thirteen residues derivatized with a moiety. In some forms of the PNA probes, there can be eleven, twelve, thirteen, fourteen, fifteen, sixteen, seventeen, eighteen, or nineteen residues derivatized with a moiety. In some forms of the PNA probes, there can be four, five, six, seven, eight, nine, ten, eleven, or twelve residues derivatized with a moiety. In some forms of the PNA probes, there can be twelve, thirteen, fourteen, fifteen, sixteen, seventeen, eighteen, or nineteen residues derivatized with a moiety. In some forms of the PNA probes, there can be four, five, six, seven, eight, nine, ten, or eleven residues derivatized with a moiety. In some forms of the PNA probes, there can be thirteen, fourteen, fifteen, sixteen, seventeen, eighteen, or nineteen residues derivatized with a moiety. In some forms of the PNA probes, there can be four, five, six, seven, eight, nine, or ten residues derivatized with a moiety. In some forms of the PNA probes, there can be fourteen, fifteen, sixteen, seventeen, eighteen, or nineteen residues derivatized with a moiety. In some forms of the PNA probes, there can be four, five, six, seven, eight, or nine residues derivatized with a moiety. In some forms of the PNA probes, there can be fifteen, sixteen, seventeen, eighteen, or nineteen residues derivatized with a moiety. In some forms of the PNA probes, there can be four, five, six, seven, or eight residues derivatized with a moiety. In some forms of the PNA probes, there can be sixteen, seventeen, eighteen, or nineteen residues derivatized with a moiety. In some forms of the PNA probes, there can be four, five, six, or seven residues derivatized with a moiety. In some forms of the PNA probes, there can be seventeen, eighteen, or nineteen residues derivatized with a moiety. In some forms of the PNA probes, there can be four, five, or six residues derivatized with a moiety. In some forms of the PNA probes, there can be eighteen or nineteen residues derivatized with a moiety. In some forms of the PNA probes, there can be four or five residues derivatized with a moiety. In some forms of the PNA probes, there can be nineteen residues derivatized with a moiety. In some forms of the PNA probes, there can be four residues derivatized with a moiety. In some forms of the PNA probes, there can be five, six, seven, eight, nine, ten, eleven, twelve, thirteen, fourteen, fifteen, sixteen, seventeen, or eighteen residues derivatized with a moiety. In some forms of the PNA probes, there can be six, seven, eight, nine, ten, eleven, twelve, thirteen, fourteen, fifteen, sixteen, or seventeen residues derivatized with a moiety. In some forms of the PNA probes, there can be seven, eight, nine, ten, eleven, twelve, thirteen, fourteen, fifteen, or sixteen residues derivatized with a moiety. In some forms of the PNA probes, there can be eight, nine, ten, eleven, twelve, thirteen, fourteen, or fifteen residues derivatized with a moiety. In some forms of the PNA probes, there can be nine, ten, eleven, twelve, thirteen, or fourteen residues derivatized with a moiety. In some forms of the PNA probes, there can be ten, eleven, twelve, or thirteen residues derivatized with a moiety. In some forms of the PNA probes, there can be eleven or twelve residues derivatized with a moiety. In some forms of the PNA probes, there can be twelve residues derivatized with a moiety. In some forms of the PNA probes, there can be eleven residues derivatized with a moiety. In some forms of the PNA probes, there can be ten residues derivatized with a moiety. In some forms of the PNA probes, there can be nine residues derivatized with a moiety. In some forms of the PNA probes, there can be eight residues derivatized with a moiety. In some forms of the PNA probes, there can be seven residues derivatized with a moiety. In some forms of the PNA probes, there can be five, six, seven, eight, nine, ten, eleven, twelve, thirteen, fourteen, fifteen, sixteen, or seventeen residues derivatized with a moiety. In some forms of the PNA probes, there can be five, six, seven, eight, nine, ten, eleven, twelve, thirteen, fourteen, fifteen, or sixteen residues derivatized with a moiety. In some forms of the PNA probes, there can be six, seven, eight, nine, ten, eleven, twelve, thirteen, fourteen, fifteen, or sixteen residues derivatized with a moiety. In some forms of the PNA probes, there can be six, seven, eight, nine, ten, eleven, twelve, thirteen, fourteen, or fifteen residues derivatized with a moiety. In some forms of the PNA probes, there can be seven, eight, nine, ten, eleven, twelve, thirteen, fourteen, or fifteen residues derivatized with a moiety. In some forms of the PNA probes, there can be seven, eight, nine, ten, eleven, twelve, thirteen, or fourteen residues derivatized with a moiety. In some forms of the PNA probes, there can be seven, eight,
nine, ten, eleven, twelve, or thirteen residues derivatized with a moiety. In some forms of the PNA probes, there can be eight, nine, ten, eleven, twelve, or thirteen residues derivatized with a moiety. In some forms of the PNA probes, there can be eight, nine, ten, eleven, or twelve residues derivatized with a moiety. In some forms of the PNA probes, there can be nine, ten, eleven, or twelve residues derivatized with a moiety. In some forms of the PNA probes, there can be nine, ten, or eleven residues derivatized with a moiety. In some forms of the PNA probes, there can be ten or eleven residues derivatized with a moiety. In some forms of the PNA probes, there can be nine or ten residues derivatized with a moiety.

In some forms of the PNA probes, there can be two, three, four, five, six, seven, eight, or nine residues derivatized with a charged moiety. In some forms of the PNA probes, there can be three, four, five, six, seven, eight, or nine residues derivatized with a charged moiety. In some forms of the PNA probes, there can be two, three, four, five, six, seven, or eight residues derivatized with a charged moiety. In some forms of the PNA probes, there can be four, five, six, seven, eight, or nine residues derivatized with a charged moiety. In some forms of the PNA probes, there can be two, three, four, five, six, or seven residues derivatized with a charged moiety. In some forms of the PNA probes, there can be five, six, seven, eight, or nine residues derivatized with a charged moiety. In some forms of the PNA probes, there can be two, three, four, five, or six residues derivatized with a charged moiety. In some forms of the PNA probes, there can be six, seven, eight, or nine residues derivatized with a charged moiety. In some forms of the PNA probes, there can be two, three, four, or five residues derivatized with a charged moiety. In some forms of the PNA probes, there can be seven, eight, or nine residues derivatized with a charged moiety. In some forms of the PNA probes, there can be two, three, or four residues derivatized with a charged moiety. In some forms of the PNA probes, there can be eight or nine residues derivatized with a charged moiety. In some forms of the PNA probes, there can be two or three residues derivatized with a charged moiety. In some forms of the PNA probes, there can be nine residues derivatized with a charged moiety. In some forms of the PNA probes, there can be eight residues derivatized with a charged moiety. In some forms of the PNA probes, there can be seven residues derivatized with a charged moiety. In some forms of the PNA probes, there can be six residues derivatized with a charged moiety. In some forms of the PNA probes, there can be five residues derivatized with a charged moiety. In some forms of the PNA probes, there can be four residues derivatized with a charged moiety. In some forms of the PNA probes, there can be three residues derivatized with a charged moiety. In some forms of the PNA probes, there can be two residues derivatized with a charged moiety. In some forms of the PNA probes, there can be three, four, five, six, seven, or eight residues derivatized with a charged moiety. In some forms of the PNA probes, there can be three, four, five, six, or seven residues derivatized with a charged moiety. In some forms of the PNA probes, there can be four, five, six, or seven residues derivatized with a charged moiety. In some forms of the PNA probes, there can be four, five, or six residues derivatized with a charged moiety. In some forms of the PNA probes, there can be three, four, or five residues derivatized with a charged moiety. In some forms of the PNA probes, there can be four or five residues derivatized with a charged moiety. In some forms of the PNA probes, there can be three or four residues derivatized with a charged moiety. In some forms of the PNA probes, there can be five or residues derivatized with a charged moiety. In some forms of the PNA probes, there can be two, three, four, five, or six residues derivatized with a charged moiety.

In some forms of the PNA probes, there can be one, two, three, four, five, six, seven, eight, nine, ten, eleven, twelve, thirteen, fourteen, fifteen, sixteen, or seventeen residues derivatized with a neutral moiety. In some forms of the PNA probes, there can be two, three, four, five, six, seven, eight, nine, ten, eleven, twelve, thirteen, fourteen, fifteen, sixteen, or seventeen residues derivatized with a neutral moiety. In some forms of the PNA probes, there can be one, two, three, four, five, six, seven, eight, nine, ten, eleven, twelve, thirteen, fourteen, fifteen, or sixteen residues derivatized with a neutral moiety. In some forms of the PNA probes, there can be three, four, five, six, seven, eight, nine, ten, eleven, twelve, thirteen, fourteen, fifteen, sixteen, or seventeen residues derivatized with a neutral moiety. In some forms of the PNA probes, there can be one, two, three, four, five, six, seven, eight, nine, ten, eleven, twelve, thirteen, fourteen, or fifteen residues derivatized with a neutral moiety. In some forms of the PNA probes, there can be four, five, six, seven, eight, nine, ten, eleven, twelve, thirteen, fourteen, fifteen, sixteen, or seventeen residues derivatized with a neutral moiety. In some forms of the PNA probes, there can be one, two, three, four, five, six, seven, eight, nine, ten, eleven, twelve, thirteen, or fourteen residues derivatized with a neutral moiety. In some forms of the PNA probes, there can be five, six, seven, eight, nine, ten, eleven, twelve, thirteen, fourteen, fifteen, sixteen, or seventeen residues derivatized with a neutral moiety. In some forms of the PNA probes, there can be one, two, three, four, five, six, seven, eight, nine, ten, eleven, twelve, or thirteen residues derivatized with a neutral moiety. In some forms of the PNA probes, there can be six, seven, eight, nine, ten, eleven, twelve, thirteen, fourteen, fifteen, sixteen, or seventeen residues derivatized with a neutral moiety. In some forms of the PNA probes, there can be one, two, three, four, five, six, seven, eight, nine, ten, eleven, or twelve residues derivatized with a neutral moiety. In some forms of the PNA probes, there can be seven, eight, nine, ten, eleven, twelve, thirteen, fourteen, fifteen, sixteen, or seventeen residues derivatized with a neutral moiety. In some forms of the PNA probes, there can be one, two, three, four, five, six, seven, eight, nine, ten, or eleven residues derivatized with a neutral moiety. In some forms of the PNA probes, there can be eight, nine, ten, eleven, twelve, thirteen, fourteen, fifteen, sixteen, or seventeen residues derivatized with a neutral moiety. In some forms of the PNA probes, there can be one, two, three, four, five, six, seven, eight, nine, or ten residues derivatized with a neutral moiety. In some forms of the PNA probes, there can be nine, ten, eleven, twelve, thirteen, fourteen, fifteen, sixteen, or seventeen residues derivatized with a neutral moiety. In some forms of the PNA probes, there can be one, two, three, four, five, six, seven, eight, or nine residues derivatized with a neutral moiety. In some forms of the PNA probes, there can be ten, eleven, twelve, thirteen, fourteen, fifteen, sixteen, or seventeen residues derivatized with a neutral moiety. In some forms of the PNA probes, there can be one, two, three, four, five, six, seven, or eight residues derivatized with a neutral moiety. In some forms of the PNA probes, there can be eleven, twelve, thirteen, fourteen, fifteen, sixteen, or seventeen residues derivatized with a neutral moiety. In some forms of the PNA probes, there can be one, two, three, four, five, six, or seven residues derivatized with a neutral moiety. In some forms of the PNA probes, there can be twelve, thirteen, fourteen, fifteen, sixteen, or seventeen residues derivatized with a neutral moiety. In some forms of the PNA probes, there can be one, two, three, four, five, or six residues derivatized with a neutral moiety. In some forms of the PNA probes, there can be thirteen, fourteen, fifteen, sixteen, or seventeen residues derivatized with a neutral moiety. In some forms of the PNA probes, there can be one, two, three, four, or five residues derivatized with a neutral moiety. In some forms of the PNA probes, there can be fourteen, fifteen, sixteen, or seventeen residues derivatized with a neutral moiety. In some forms of the PNA probes, there can be one, two, three, or four residues derivatized with a neutral moiety. In some forms of the PNA probes, there can be fifteen, sixteen, or seventeen residues derivatized with a neutral moiety. In some forms of the PNA probes, there can be one, two, or three residues derivatized with a neutral moiety. In some forms of the PNA probes, there can be sixteen or seventeen residues derivatized with a neutral moiety. In some forms of the PNA probes, there can be one or two residues derivatized with a neutral moiety. In some forms of the PNA probes, there can be seventeen residues derivatized with a neutral moiety. In some forms of the PNA probes, there can be sixteen residues derivatized with a neutral moiety. In some forms of the PNA probes, there can be fifteen residues derivatized with a neutral moiety. In some forms of the PNA probes, there can be fourteen residues derivatized with a neutral moiety. In some forms of the PNA probes, there can be thirteen residues derivatized with a neutral moiety. In some forms of the PNA probes, there can be twelve residues derivatized with a neutral moiety. In some forms of the PNA probes, there can be eleven residues derivatized with a neutral moiety. In some forms of the PNA probes, there can be ten residues derivatized with a neutral moiety. In some forms of the PNA probes, there can be nine residues derivatized with a neutral moiety. In some forms of the PNA probes, there can be eight residues derivatized with a neutral moiety. In some forms of the PNA probes, there can be seven residues derivatized with a neutral moiety. In some forms of the PNA probes, there can be six residues derivatized with a neutral moiety. In some forms of the PNA probes, there can be five residues derivatized with a neutral moiety. In some forms of the PNA probes, there can be four residues derivatized with a neutral moiety. In some forms of the PNA probes, there can be three residues derivatized with a neutral moiety. In some forms of the PNA probes, there can be two residues derivatized with a neutral moiety. In some forms of the PNA probes, there can be one residue derivatized with a neutral moiety. In some forms of the PNA probes, there can be two, three, four, five, six, seven, eight, nine, ten, eleven, twelve, thirteen, fourteen, fifteen, or sixteen residues derivatized with a neutral moiety. In some forms of the PNA probes, there can be two, three, four, five, six, seven, eight, nine, ten, eleven, twelve, thirteen, fourteen, or fifteen residues derivatized with a neutral moiety. In some forms of the PNA probes, there can be two, three, four, five, six, seven, eight, nine, ten, eleven, twelve, thirteen, or fourteen residues derivatized with a neutral moiety. In some forms of the PNA probes, there can be three, four, five, six, seven, eight, nine, ten, eleven, twelve, thirteen, or fourteen residues derivatized with a neutral moiety. In some forms of the PNA probes, there can be three, four, five, six, seven, eight, nine, ten, eleven, twelve, or thirteen residues derivatized with a neutral moiety. In some forms of the PNA probes, there can be three, four, five, six, seven, eight, nine, ten, eleven, or twelve residues derivatized with a neutral moiety. In some forms of the PNA probes, there can be four, five, six, seven, eight, nine, ten, eleven, or twelve residues derivatized with a neutral moiety. In some forms of the PNA probes, there can be four, five, six, seven, eight, nine, ten, or eleven residues derivatized with a neutral moiety. In some forms of the PNA probes, there can be four, five, six, seven, eight, nine, or ten residues derivatized with a neutral moiety. In some forms of the PNA probes, there can be five, six, seven, eight, nine, or ten residues derivatized with a neutral moiety. In some forms of the PNA probes, there can be five, six, seven, eight, or nine residues derivatized with a neutral moiety. In some forms of the PNA probes, there can be five, six, seven, or eight residues derivatized with a neutral moiety. In some forms of the PNA probes, there can be five, six, or seven residues derivatized with a neutral moiety. In some forms of the PNA probes, there can be five or six residues derivatized with a neutral moiety. In some forms of the PNA probes, there can be three, four, or five residues derivatized with a neutral moiety. In some forms of the PNA probes, there can be two, three, four, or five residues derivatized with a neutral moiety. In some forms of the PNA probes, there can be two, three, four, five, or six residues derivatized with a neutral moiety.

In some forms of the PNA probes, there can be one, two, three, four, five, six, seven, eight, nine, ten, eleven, twelve, thirteen, fourteen, fifteen, sixteen, or seventeen residues not derivatized with a moiety. In some forms of the PNA probes, there can be two, three, four, five, six, seven, eight, nine, ten, eleven, twelve, thirteen, fourteen, fifteen, sixteen, or seventeen residues not derivatized with a moiety. In some forms of the PNA probes, there can be one, two, three, four, five, six, seven, eight, nine, ten, eleven, twelve, thirteen, fourteen, fifteen, or sixteen residues not derivatized with a moiety. In some forms of the PNA probes, there can be three, four, five, six, seven, eight, nine, ten, eleven, twelve, thirteen, fourteen, fifteen, sixteen, or seventeen residues not derivatized with a moiety. In some forms of the PNA probes, there can be one, two, three, four, five, six, seven, eight, nine, ten, eleven, twelve, thirteen, fourteen, or fifteen residues not derivatized with a moiety. In some forms of the PNA probes, there can be four, five, six, seven, eight, nine, ten, eleven, twelve, thirteen, fourteen, fifteen, sixteen, or seventeen residues not derivatized with a moiety. In some forms of the PNA probes, there can be one, two, three, four, five, six, seven, eight, nine, ten, eleven, twelve, thirteen, or fourteen residues not derivatized with a moiety. In some forms of the PNA probes, there can be five, six, seven, eight, nine, ten, eleven, twelve, thirteen, fourteen, fifteen, sixteen, or seventeen residues not derivatized with a moiety. In some forms of the PNA probes, there can be one, two, three, four, five, six, seven, eight, nine, ten, eleven, twelve, or thirteen residues not derivatized with a moiety. In some forms of the PNA probes, there can be six, seven, eight, nine, ten, eleven, twelve, thirteen, fourteen, fifteen, sixteen, or seventeen residues not derivatized with a moiety. In some forms of the PNA probes, there can be one, two, three, four, five, six, seven, eight, nine, ten, eleven, or twelve residues not derivatized with a moiety. In some forms of the PNA probes, there can be seven, eight, nine, ten, eleven, twelve, thirteen, fourteen, fifteen, sixteen, or seventeen residues not derivatized with a moiety. In some forms of the PNA probes, there can be one, two, three, four, five, six, seven, eight, nine, ten, or eleven residues not derivatized with a moiety. In some forms of the PNA probes, there can be eight, nine, ten, eleven, twelve, thirteen, fourteen, fifteen, sixteen, or seventeen residues not derivatized with a moiety. In some forms of the PNA probes, there can be one, two, three, four, five, six, seven, eight, nine, or ten residues not derivatized with a moiety. In some forms of the PNA probes, there can be nine, ten, eleven, twelve, thirteen, fourteen, fifteen, sixteen, or seventeen residues not derivatized with a moiety. In some forms of the PNA probes, there can be one, two, three, four, five, six, seven, eight, or nine residues not derivatized with a moiety. In some forms of the PNA probes, there can be ten, eleven, twelve, thirteen, fourteen, fifteen, sixteen, or seventeen residues not derivatized with a moiety. In some forms of the PNA probes, there can be one, two, three, four, five, six, seven, or eight residues not derivatized with a moiety. In some forms of the PNA probes, there can be eleven, twelve, thirteen, fourteen, fifteen, sixteen, or seventeen residues not derivatized with a moiety. In some forms of the PNA probes, there can be one, two, three, four, five, six, or seven residues not derivatized with a moiety. In some forms of the PNA probes, there can be twelve, thirteen, fourteen, fifteen, sixteen, or seventeen residues not derivatized with a moiety. In some forms of the PNA probes, there can be one, two, three, four, five, or six residues not derivatized with a moiety. In some forms of the PNA probes, there can be thirteen, fourteen, fifteen, sixteen, or seventeen residues not derivatized with a moiety. In some forms of the PNA probes, there can be one, two, three, four, or five residues not derivatized with a moiety. In some forms of the PNA probes, there can be fourteen, fifteen, sixteen, or seventeen residues not derivatized with a moiety. In some forms of the PNA probes, there can be one, two, three, or four residues not derivatized with a moiety. In some forms of the PNA probes, there can be fifteen, sixteen, or seventeen residues not derivatized with a moiety. In some forms of the PNA probes, there can be one, two, or three residues not derivatized with a moiety. In some forms of the PNA probes, there can be sixteen or seventeen residues not derivatized with a moiety. In some forms of the PNA probes, there can be one or two residues not derivatized with a moiety. In some forms of the PNA probes, there can be seventeen residues not derivatized with a moiety. In some forms of the PNA probes, there can be sixteen residues not derivatized with a moiety. In some forms of the PNA probes, there can be fifteen residues not derivatized with a moiety. In some forms of the PNA probes, there can be fourteen residues not derivatized with a moiety. In some forms of the PNA probes, there can be thirteen residues not derivatized with a moiety. In some forms of the PNA probes, there can be twelve residues not derivatized with a moiety. In some forms of the PNA probes, there can be eleven residues not derivatized with a moiety. In some forms of the PNA probes, there can be ten residues not derivatized with a moiety. In some forms of the PNA probes, there can be nine residues not derivatized with a moiety. In some forms of the PNA probes, there can be eight residues not derivatized with a moiety. In some forms of the PNA probes, there can be seven residues not derivatized with a moiety. In some forms of the PNA probes, there can be six residues not derivatized with a moiety. In some forms of the PNA probes, there can be five residues not derivatized with a moiety. In some forms of the PNA probes, there can be four residues not derivatized with a moiety. In some forms of the PNA probes, there can be three residues not derivatized with a moiety. In some forms of the PNA probes, there can be two residues not derivatized with a moiety. In some forms of the PNA probes, there can be one residue not derivatized with a moiety. In some forms of the PNA probes, there can be two, three, four, five, six, seven, eight, nine, ten, eleven, twelve, thirteen, fourteen, fifteen, or sixteen residues not derivatized with a moiety. In some forms of the PNA probes, there can be two, three, four, five, six, seven, eight, nine, ten, eleven, twelve, thirteen, fourteen, or fifteen residues not derivatized with a moiety. In some forms of the PNA probes, there can be two, three, four, five, six, seven, eight, nine, ten, eleven, twelve, thirteen, or fourteen residues not derivatized with a moiety. In some forms of the PNA probes, there can be three, four, five, six, seven, eight, nine, ten, eleven, twelve, thirteen, or fourteen residues not derivatized with a moiety. In some forms of the PNA probes, there can be three, four, five, six, seven, eight, nine, ten, eleven, twelve, or thirteen residues not derivatized with a moiety. In some forms of the PNA probes, there can be three, four, five, six, seven, eight, nine, ten, eleven, or twelve residues not derivatized with a moiety. In some forms of the PNA probes, there can be four, five, six, seven, eight, nine, ten, eleven, or twelve residues not derivatized with a moiety. In some forms of the PNA probes, there can be four, five, six, seven, eight, nine, ten, or eleven residues not derivatized with a moiety. In some forms of the PNA probes, there can be four, five, six, seven, eight, nine, or ten residues not derivatized with a moiety. In some forms of the PNA probes, there can be five, six, seven, eight, nine, or ten residues not derivatized with a moiety. In some forms of the PNA probes, there can be five, six, seven, eight, or nine residues not derivatized with a moiety. In some forms of the PNA probes, there can be five, six, seven, or eight residues not derivatized with a moiety. In some forms of the PNA probes, there can be five, six, or seven residues not derivatized with a moiety. In some forms of the PNA probes, there can be five or six residues not derivatized with a moiety. In some forms of the PNA probes, there can be three, four, or five residues not derivatized with a moiety. In some forms of the PNA probes, there can be two, three, four, or five residues not derivatized with a moiety. In some forms of the PNA probes, there can be two, three, four, five, or six residues not derivatized with a moiety.

In some forms of the PNA probes, an average of at or between about 15% to 100% of the residues in the probe are derivatized with a moiety. In some forms of the PNA probes, an average of at or between about 20% to 80% of the residues in the probe are derivatized with a moiety. In some forms of the PNA probes, an average of at or between about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, or 66% to, independently and in any combination, 30%, 31%, 2%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 88%, 89%, 90%, 91%, 92%, 93%, 94%, 95%, 96%, 97%, 98%, 99%, or 100% of the residues in the probe are derivatized with a moiety. In some forms of the PNA probes, an average of about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 88%, 89%, 90%, 91%, 92%, 93%, 94%, 95%, 96%, 97%, 98%, 99%, or 100% of the residues in the probe are derivatized with a moiety. In some forms of the PNA probes, an average of at or between about 16% to 100% of the residues in the probe are derivatized with a moiety. In some forms of the PNA probes, an average of at or between about 15% to 90% of the residues in the probe are derivatized with a moiety. In some forms of the PNA probes, an average of at or between about 17% to 100% of the residues in the probe are derivatized with a moiety. In some forms of the PNA probes, an average of at or between about 15% to 85% of the residues in the probe are derivatized with a moiety. In some forms of the PNA probes, an average of at or between about 18% to 100% of the residues in the probe are derivatized with a moiety. In some forms of the PNA probes, an average of at or between about 15% to 80% of the residues in the probe are derivatized with a moiety. In some forms of the PNA probes, an average of at or between about 19% to 100% of the residues in the probe are derivatized with a moiety. In some forms of the PNA probes, an average of at or between about 15% to 75% of the residues in the probe are derivatized with a moiety. In some forms of the PNA probes, an average of at or between about 20% to 100% of the residues in the probe are derivatized with a moiety. In some forms of the PNA probes, an average of at or between about 15% to 70% of the residues in the probe are derivatized with a moiety. In some forms of the PNA probes, an average of at or between about 21% to 100% of the residues in the probe are derivatized with a moiety. In some forms of the PNA probes, an average of at or between about 15% to 68% of the residues in the probe are derivatized with a moiety. In some forms of the PNA probes, an average of at or between about 22% to 100% of the residues in the probe are derivatized with a moiety. In some forms of the PNA probes, an average of at or between about 15% to 66% of the residues in the probe are derivatized with a moiety. In some forms of the PNA probes, an average of at or between about 23% to 100% of the residues in the probe are derivatized with a moiety. In some forms of the PNA probes, an average of at or between about 15% to 64% of the residues in the probe are derivatized with a moiety. In some forms of the PNA probes, an average of at or between about 24% to 100% of the residues in the probe are derivatized with a moiety. In some forms of the PNA probes, an average of at or between about 15% to 62% of the residues in the probe are derivatized with a moiety. In some forms of the PNA probes, an average of at or between about 25% to 100% of the residues in the probe are derivatized with a moiety. In some forms of the PNA probes, an average of at or between about 15% to 60% of the residues in the probe are derivatized with a moiety. In some forms of the PNA probes, an average of at or between about 26% to 100% of the residues in the probe are derivatized with a moiety. In some forms of the PNA probes, an average of at or between about 15% to 58% of the residues in the probe are derivatized with a moiety. In some forms of the PNA probes, an average of at or between about 27% to 100% of the residues in the probe are derivatized with a moiety. In some forms of the PNA probes, an average of at or between about 15% to 56% of the residues in the probe are derivatized with a moiety. In some forms of the PNA probes, an average of at or between about 28% to 100% of the residues in the probe are derivatized with a moiety. In some forms of the PNA probes, an average of at or between about 15% to 54% of the residues in the probe are derivatized with a moiety. In some forms of the PNA probes, an average of at or between about 29% to 100% of the residues in the probe are derivatized with a moiety. In some forms of the PNA probes, an average of at or between about 15% to 52% of the residues in the probe are derivatized with a moiety. In some forms of the PNA probes, an average of at or between about 30% to 100% of the residues in the probe are derivatized with a moiety. In some forms of the PNA probes, an average of at or between about 15% to 50% of the residues in the probe are derivatized with a moiety. In some forms of the PNA probes, an average of at or between about 31% to 100% of the residues in the probe are derivatized with a moiety. In some forms of the PNA probes, an average of at or between about 15% to 48% of the residues in the probe are derivatized with a moiety. In some forms of the PNA probes, an average of at or between about 32% to 100% of the residues in the probe are derivatized with a moiety. In some forms of the PNA probes, an average of at or between about 15% to 46% of the residues in the probe are derivatized with a moiety. In some forms of the PNA probes, an average of at or between about 33% to 100% of the residues in the probe are derivatized with a moiety. In some forms of the PNA probes, an average of at or between about 15% to 44% of the residues in the probe are derivatized with a moiety. In some forms of the PNA probes, an average of at or between about 34% to 100% of the residues in the probe are derivatized with a moiety. In some forms of the PNA probes, an average of at or between about 15% to 42% of the residues in the probe are derivatized with a moiety. In some forms of the PNA probes, an average of at or between about 35% to 100% of the residues in the probe are derivatized with a moiety. In some forms of the PNA probes, an average of at or between about 15% to 40% of the residues in the probe are derivatized with a moiety. In some forms of the PNA probes, an average of at or between about 36% to 100% of the residues in the probe are derivatized with a moiety. In some forms of the PNA probes, an average of at or between about 15% to 38% of the residues in the probe are derivatized with a moiety. In some forms of the PNA probes, an average of at or between about 37% to 100% of the residues in the probe are derivatized with a moiety. In some forms of the PNA probes, an average of at or between about 15% to 36% of the residues in the probe are derivatized with a moiety. In some forms of the PNA probes, an average of at or between about 38% to 100% of the residues in the probe are derivatized with a moiety. In some forms of the PNA probes, an average of at or between about 15% to 34% of the residues in the probe are derivatized with a moiety. In some forms of the PNA probes, an average of at or between about 40% to 100% of the residues in the probe are derivatized with a moiety. In some forms of the PNA probes, an average of at or between about 15% to 32% of the residues in the probe are derivatized with a moiety. In some forms of the PNA probes, an average of at or between about 41% to 100% of the residues in the probe are derivatized with a moiety. In some forms of the PNA probes, an average of at or between about 15% to 30% of the residues in the probe are derivatized with a moiety. In some forms of the PNA probes, an average of at or between about 42% to 100% of the residues in the probe are derivatized with a moiety. In some forms of the PNA probes, an average of at or between about 15% to 28% of the residues in the probe are derivatized with a moiety. In some forms of the PNA probes, an average of at or between about 43% to 100% of the residues in the probe are derivatized with a moiety. In some forms of the PNA probes, an average of at or between about 15% to 26% of the residues in the probe are derivatized with a moiety. In some forms of the PNA probes, an average of at or between about 44% to 100% of the residues in the probe are derivatized with a moiety. In some forms of the PNA probes, an average of at or between about 15% to 24% of the residues in the probe are derivatized with a moiety. In some forms of the PNA probes, an average of at or between about 45% to 100% of the residues in the probe are derivatized with a moiety. In some forms of the PNA probes, an average of at or between about 15% to 22% of the residues in the probe are derivatized with a moiety. In some forms of the PNA probes, an average of at or between about 46% to 100% of the residues in the probe are derivatized with a moiety. In some forms of the PNA probes, an average of at or between about 15% to 20% of the residues in the probe are derivatized with a moiety.

For example, 52.6% of the residues of the probe T*gTgC*cTccC*gTtTT*gTcC* (SEQ ID NO:6) are derivatized with a moiety, 47.4% of the residues of the probe cT*tCaT*CtCgT*cTaC*aaT*a (SEQ ID NO:10) are derivatized with a moiety, and 52.6% of the residues of the probe agT*CgTtC*tTcT*aTCaT*cT (SEQ ID NO:20) are derivatized with a moiety.

In some forms of the PNA probes, an average of at or between about 15% to 40% of the residues in the probe are derivatized with a charged moiety. In some forms of the PNA probes, an average of at or between about 15% to 35% of the residues in the probe are derivatized with a charged moiety. In some forms of the PNA probes, an average of at or between about 20% to 33% of the residues in the probe are derivatized with a charged moiety. In some forms of the PNA probes, an average of at or between about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% to, independently and in any combination, 20%, 21%, 22%, 23%, 24%, 25%, 26%, 27%, 28%, 29%, 30%, 31%, 2%, 33%, 34%, 35%, 36%, 37%, 38%, 39%, or 40% of the residues in the probe are derivatized with a charged moiety. In some forms of the PNA probes, an average of about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% of the residues in the probe are derivatized with a charged moiety. In some forms of the PNA probes, an average of at or between about 16% to 35% of the residues in the probe are derivatized with a charged moiety. In some forms of the PNA probes, an average of at or between about 15% to 34% of the residues in the probe are derivatized with a charged moiety. In some forms of the PNA probes, an average of at or between about 17% to 35% of the residues in the probe are derivatized with a charged moiety. In some forms of the PNA probes, an average of at or between about 15% to 33% of the residues in the probe are derivatized with a charged moiety. In some forms of the PNA probes, an average of at or between about 18% to 35% of the residues in the probe are derivatized with a charged moiety. In some forms of the PNA probes, an average of at or between about 15% to 32% of the residues in the probe are derivatized with a charged moiety. In some forms of the PNA probes, an average of at or between about 19% to 35% of the residues in the probe are derivatized with a charged moiety. In some forms of the PNA probes, an average of at or between about 15% to 31% of the residues in the probe are derivatized with a charged moiety. In some forms of the PNA probes, an average of at or between about 20% to 35% of the residues in the probe are derivatized with a charged moiety. In some forms of the PNA probes, an average of at or between about 15% to 30% of the residues in the probe are derivatized with a charged moiety. In some forms of the PNA probes, an average of at or between about 21% to 35% of the residues in the probe are derivatized with a charged moiety. In some forms of the PNA probes, an average of at or between about 15% to 29% of the residues in the probe are derivatized with a charged moiety. In some forms of the PNA probes, an average of at or between about 22% to 35% of the residues in the probe are derivatized with a charged moiety. In some forms of the PNA probes, an average of at or between about 15% to 28% of the residues in the probe are derivatized with a charged moiety. In some forms of the PNA probes, an average of at or between about 23% to 35% of the residues in the probe are derivatized with a charged moiety. In some forms of the PNA probes, an average of at or between about 15% to 27% of the residues in the probe are derivatized with a charged moiety. In some forms of the PNA probes, an average of at or between about 24% to 35% of the residues in the probe are derivatized with a charged moiety. In some forms of the PNA probes, an average of at or between about 15% to 26% of the residues in the probe are derivatized with a charged moiety. In some forms of the PNA probes, an average of at or between about 25% to 35% of the residues in the probe are derivatized with a charged moiety. In some forms of the PNA probes, an average of at or between about 15% to 25% of the residues in the probe are derivatized with a charged moiety. In some forms of the PNA probes, an average of at or between about 26% to 35% of the residues in the probe are derivatized with a charged moiety. In some forms of the PNA probes, an average of at or between about 15% to 24% of the residues in the probe are derivatized with a charged moiety. In some forms of the PNA probes, an average of at or between about 27% to 35% of the residues in the probe are derivatized with a charged moiety. In some forms of the PNA probes, an average of at or between about 15% to 23% of the residues in the probe are derivatized with a charged moiety. In some forms of the PNA probes, an average of at or between about 28% to 35% of the residues in the probe are derivatized with a charged moiety. In some forms of the PNA probes, an average of at or between about 15% to 22% of the residues in the probe are derivatized with a charged moiety. In some forms of the PNA probes, an average of at or between about 29% to 35% of the residues in the probe are derivatized with a charged moiety. In some forms of the PNA probes, an average of at or between about 15% to 21% of the residues in the probe are derivatized with a charged moiety. In some forms of the PNA probes, an average of at or between about 30% to 35% of the residues in the probe are derivatized with a charged moiety. In some forms of the PNA probes, an average of at or between about 15% to 20% of the residues in the probe are derivatized with a charged moiety. In some forms of the PNA probes, an average of at or between about 31% to 35% of the residues in the probe are derivatized with a charged moiety. In some forms of the PNA probes, an average of at or between about 15% to 19% of the residues in the probe are derivatized with a charged moiety. In some forms of the PNA probes, an average of at or between about 32% to 35% of the residues in the probe are derivatized with a charged moiety. In some forms of the PNA probes, an average of at or between about 15% to 18% of the residues in the probe are derivatized with a charged moiety. In some forms of the PNA probes, an average of at or between about 33% to 35% of the residues in the probe are derivatized with a charged moiety. In some forms of the PNA probes, an average of at or between about 15% to 17% of the residues in the probe are derivatized with a charged moiety. In some forms of the PNA probes, an average of at or between about 34% to 35% of the residues in the probe are derivatized with a charged moiety. In some forms of the PNA probes, an average of at or between about 15% to 16% of the residues in the probe are derivatized with a charged moiety. In some forms of the PNA probes, an average of at or between about 20% to 34% of the residues in the probe are derivatized with a charged moiety. In some forms of the PNA probes, an average of at or between about 21% to 34% of the residues in the probe are derivatized with a charged moiety. In some forms of the PNA probes, an average of at or between about 21% to 33% of the residues in the probe are derivatized with a charged moiety. In some forms of the PNA probes, an average of at or between about 22% to 33% of the residues in the probe are derivatized with a charged moiety. In some forms of the PNA probes, an average of at or between about 23% to 33% of the residues in the probe are derivatized with a charged moiety. In some forms of the PNA probes, an average of at or between about 23% to 32% of the residues in the probe are derivatized with a charged moiety. In some forms of the PNA probes, an average of at or between about 24% to 32% of the residues in the probe are derivatized with a charged moiety. In some forms of the PNA probes, an average of at or between about 25% to 32% of the residues in the probe are derivatized with a charged moiety. In some forms of the PNA probes, an average of at or between about 25% to 31% of the residues in the probe are derivatized with a charged moiety. In some forms of the PNA probes, an average of at or between about 26% to 31% of the residues in the probe are derivatized with a charged moiety. In some forms of the PNA probes, an average of at or between about 26% to 30% of the residues in the probe are derivatized with a charged moiety. In some forms of the PNA probes, an average of at or between about 27% to 30% of the residues in the probe are derivatized with a charged moiety. In some forms of the PNA probes, an average of at or between about 27% to 29% of the residues in the probe are derivatized with a charged moiety. In some forms of the PNA probes, an average of at or between about 28% to 29% of the residues in the probe are derivatized with a charged moiety.

For example, 26.3% of the residues of the probe T*gTgC*cTccC*gTtTT*gTcC* (SEQ ID NO:6) are derivatized with a charged moiety, 26.3% of the residues of the probe cT*tCaT*CtCgT*cTaC*aaT*a (SEQ ID NO:10) are derivatized with a charged moiety, and 21.1% of the residues of the probe agT*CgTtC*tTcT*aTCaT*cT (SEQ ID NO:20) are derivatized with a charged moiety.

In some forms of the PNA probes, there can be independently a total of zero, one, two, three, four, five, or six flanking residues not derivatized with a moiety (that is, not derivatized with a moiety between both of the end-proximal residues derivatized with a moiety and their respective ends of the probe). In some forms of the PNA probes, there can be independently a total of zero, one, two, three, four, or five flanking residues not derivatized with a moiety (that is, not derivatized with a moiety between both of the end-proximal derivatized residues and their respective ends of the probe). In some forms of the PNA probes, there can be independently a total of zero, one, two, three, or four flanking residues not derivatized with a moiety (that is, not derivatized with a moiety between both of the end-proximal derivatized residues and their respective ends of the probe). In some forms of the PNA probes, there can be independently a total of zero, one, two, or three flanking residues not derivatized with a moiety (that is, not derivatized with a moiety between both of the end-proximal derivatized residues and their respective ends of the probe). In some forms of the PNA probes, there can be independently a total of zero, one, or two flanking residues not derivatized with a moiety (that is, not derivatized with a moiety between both of the end-proximal derivatized residues and their respective ends of the probe). In some forms of the PNA probes, there can be independently a total of zero or one flanking residues not derivatized with a moiety (that is, not derivatized with a moiety between both of the end-proximal derivatized residues and their respective ends of the probe). In some forms of the PNA probes, there can be a total of zero flanking residues not derivatized with a moiety (that is, not derivatized with a moiety between both of the end-proximal derivatized residues and their respective ends of the probe). For example, the probe T*gTgC*cTccC*gTtTT*gTcC* (SEQ ID NO:6) has a total of zero flanking residues not derivatized with a moiety (that is, not derivatized with a moiety between both of the end-proximal derivatized residues and their respective ends of the probe), the probe cT*tCaT*CtCgT*cTaC*aaT*a (SEQ ID NO:10) has a total of two flanking residues not derivatized with a moiety (that is, not derivatized with a moiety between both of the end-proximal derivatized residues and their respective ends of the probe), and the probe agT*CgTtC*tTcT*aTCaT*cT (SEQ ID NO:20) has a total of two flanking residues not derivatized with a moiety (that is, not derivatized with a moiety between both of the end-proximal derivatized residues and their respective ends of the probe).

In some forms of the PNA probes, there can be independently zero, one, two, three, or four residues not derivatized with a moiety between each of the end-proximal residues derivatized with a moiety and their respective ends of the probe. In some forms of the PNA probes, there can be independently one, two, three, or four residues not derivatized with a moiety between each of the end-proximal residues derivatized with a moiety and their respective ends of the probe. In some forms of the PNA probes, there can be independently zero, one, two, or three residues not derivatized with a moiety between each of the end-proximal residues derivatized with a moiety and their respective ends of the probe. In some forms of the PNA probes, there can be independently two, three, or four residues not derivatized with a moiety between each of the end-proximal residues derivatized with a moiety and their respective ends of the probe. In some forms of the PNA probes, there can be independently zero, one, or two residues not derivatized with a moiety between each of the end-proximal residues derivatized with a moiety and their respective ends of the probe. In some forms of the PNA probes, there can be independently three or four residues not derivatized with a moiety between each of the end-proximal residues derivatized with a moiety and their respective ends of the probe. In some forms of the PNA probes, there can be independently two or three residues not derivatized with a moiety between each of the end-proximal residues derivatized with a moiety and their respective ends of the probe. In some forms of the PNA probes, there can be independently one or two residues not derivatized with a moiety between each of the end-proximal residues derivatized with a moiety and their respective ends of the probe. In some forms of the PNA probes, there can be independently zero or one residues not derivatized with a moiety between each of the end-proximal residues derivatized with a moiety and their respective ends of the probe. In some forms of the PNA probes, there can be independently four residues not derivatized with a moiety between each of the end-proximal residues derivatized with a moiety and their respective ends of the probe. In some forms of the PNA probes, there can be independently three residues not derivatized with a moiety between each of the end-proximal residues derivatized with a moiety and their respective ends of the probe. In some forms of the PNA probes, there can be independently two residues not derivatized with a moiety between each of the end-proximal residues derivatized with a moiety and their respective ends of the probe. In some forms of the PNA probes, there can be independently one residue not derivatized with a moiety between each of the end-proximal residues derivatized with a moiety and their respective ends of the probe. In some forms of the PNA probes, there can be independently zero residues not derivatized with a moiety between each of the end-proximal residues derivatized with a moiety and their respective ends of the probe.

For example, the probe T*gTgC*cTccC*gTtTT*gTcC* (SEQ ID NO:6) has zero residues not derivatized with a moiety between the N-terminal end and its end-proximal derivatized residue and zero residues not derivatized with a moiety between the C-terminal end and its end-proximal derivatized residue, the probe cT*tCaT*CtCgT*cTaC*aaT*a (SEQ ID NO:10) has one residue not derivatized with a moiety between the N-terminal end and its end-proximal derivatized residue and one residue not derivatized with a moiety between the C-terminal end and its end-proximal derivatized residue, and the probe agT*CgTtC*tTcT*aTCaT*cT (SEQ ID NO:20) has two residues not derivatized with a moiety between the N-terminal end and its end-proximal derivatized residue and zero residues not derivatized with a moiety between the C-terminal end and its end-proximal derivatized residue.

In some forms of the PNA probes, there can be independently a total of zero, one, two, three, four, five, six, seven, eight, or nine flanking residues not derivatized with a charged moiety (that is, not derivatized with a charged moiety between both of the end-proximal residues derivatized with a charged moiety and their respective ends of the probe). In some forms of the PNA probes, there can be independently a total of zero, one, two, three, four, five, six, seven, or eight flanking residues not derivatized with a charged moiety (that is, not derivatized with a charged moiety between both of the end-proximal residues derivatized with a charged moiety and their respective ends of the probe). In some forms of the PNA probes, there can be independently a total of zero, one, two, three, four, five, six, or seven flanking residues not derivatized with a charged moiety (that is, not derivatized with a charged moiety between both of the end-proximal residues derivatized with a charged moiety and their respective ends of the probe). In some forms of the PNA probes, there can be independently a total of zero, one, two, three, four, five, or six flanking residues not derivatized with a charged moiety (that is, not derivatized with a charged moiety between both of the end-proximal residues derivatized with a charged moiety and their respective ends of the probe). In some forms of the PNA probes, there can be independently a total of zero, one, two, three, four, or five flanking residues not derivatized with a charged moiety (that is, not derivatized with a charged moiety between both of the end-proximal derivatized residues and their respective ends of the probe). In some forms of the PNA probes, there can be independently a total of zero, one, two, three, or four flanking residues not derivatized with a charged moiety (that is, not derivatized with a charged moiety between both of the end-proximal derivatized residues and their respective ends of the probe). In some forms of the PNA probes, there can be independently a total of zero, one, two, or three flanking residues not derivatized with a charged moiety (that is, not derivatized with a charged moiety between both of the end-proximal derivatized residues and their respective ends of the probe). In some forms of the PNA probes, there can be independently a total of zero, one, or two flanking residues not derivatized with a charged moiety (that is, not derivatized with a charged moiety between both of the end-proximal derivatized residues and their respective ends of the probe). In some forms of the PNA probes, there can be independently a total of zero or one flanking residues not derivatized with a charged moiety (that is, not derivatized with a charged moiety between both of the end-proximal derivatized residues and their respective ends of the probe). In some forms of the PNA probes, there can be a total of zero flanking residues not derivatized with a charged moiety (that is, not derivatized with a charged moiety between both of the end-proximal derivatized residues and their respective ends of the probe). In some forms of the PNA probes, there can be independently a total of one flanking residues not derivatized with a charged moiety (that is, not derivatized with a charged moiety between both of the end-proximal residues derivatized with a charged moiety and their respective ends of the probe). In some forms of the PNA probes, there can be independently a total of two flanking residues not derivatized with a charged moiety (that is, not derivatized with a charged moiety between both of the end-proximal residues derivatized with a charged moiety and their respective ends of the probe). In some forms of the PNA probes, there can be independently a total of three flanking residues not derivatized with a charged moiety (that is, not derivatized with a charged moiety between both of the end-proximal residues derivatized with a charged moiety and their respective ends of the probe). In some forms of the PNA probes, there can be independently a total of four flanking residues not derivatized with a charged moiety (that is, not derivatized with a charged moiety between both of the end-proximal residues derivatized with a charged moiety and their respective ends of the probe). In some forms of the PNA probes, there can be independently a total of five flanking residues not derivatized with a charged moiety (that is, not derivatized with a charged moiety between both of the end-proximal residues derivatized with a charged moiety and their respective ends of the probe). In some forms of the PNA probes, there can be independently a total of six flanking residues not derivatized with a charged moiety (that is, not derivatized with a charged moiety between both of the end-proximal residues derivatized with a charged moiety and their respective ends of the probe). In some forms of the PNA probes, there can be independently a total of seven flanking residues not derivatized with a charged moiety (that is, not derivatized with a charged moiety between both of the end-proximal residues derivatized with a charged moiety and their respective ends of the probe). In some forms of the PNA probes, there can be independently a total of eight flanking residues not derivatized with a charged moiety (that is, not derivatized with a charged moiety between both of the end-proximal residues derivatized with a charged moiety and their respective ends of the probe). In some forms of the PNA probes, there can be independently a total of nine flanking residues not derivatized with a charged moiety (that is, not derivatized with a charged moiety between both of the end-proximal residues derivatized with a charged moiety and their respective ends of the probe). For example, the probe T*gTgC*cTccC*gTtTT*gTcC* (SEQ ID NO:6) has a total of zero flanking residues not derivatized with a charged moiety (that is, not derivatized with a charged moiety between both of the end-proximal derivatized residues and their respective ends of the probe), the probe cT*tCaT*CtCgT*cTaC*aaT*a (SEQ ID NO:10) has a total of two flanking residues not derivatized with a charged moiety (that is, not derivatized with a charged moiety between both of the end-proximal derivatized residues and their respective ends of the probe), and the probe agT*CgTtC*tTcT*aTCaT*cT (SEQ ID NO:20) has a total of two flanking residues not derivatized with a charged moiety (that is, not derivatized with a charged moiety between both of the end-proximal derivatized residues and their respective ends of the probe).

In some forms of the PNA probes, there can be independently zero, one, two, three, four, five, six, or seven residues not derivatized with a charged moiety between each of the end-proximal residues derivatized with a charged moiety and their respective ends of the probe. In some forms of the PNA probes, there can be independently one, two, three, four, five, six, or seven residues not derivatized with a charged moiety between each of the end-proximal residues derivatized with a charged moiety and their respective ends of the probe. In some forms of the PNA probes, there can be independently zero, one, two, three, four, five, or six residues not derivatized with a charged moiety between each of the end-proximal residues derivatized with a charged moiety and their respective ends of the probe. In some forms of the PNA probes, there can be independently two, three, four, five, six, or seven residues not derivatized with a charged moiety between each of the end-proximal residues derivatized with a charged moiety and their respective ends of the probe. In some forms of the PNA probes, there can be independently zero, one, two, three, four, or five residues not derivatized with a charged moiety between each of the end-proximal residues derivatized with a charged moiety and their respective ends of the probe. In some forms of the PNA probes, there can be independently three, four, five, six, or seven residues not derivatized with a charged moiety between each of the end-proximal residues derivatized with a charged moiety and their respective ends of the probe. In some forms of the PNA probes, there can be independently zero, one, two, three, or four residues not derivatized with a charged moiety between each of the end-proximal residues derivatized with a charged moiety and their respective ends of the probe. In some forms of the PNA probes, there can be independently four, five, six, or seven residues not derivatized with a charged moiety between each of the end-proximal residues derivatized with a charged moiety and their respective ends of the probe. In some forms of the PNA probes, there can be independently zero, one, two, or three residues not derivatized with a charged moiety between each of the end-proximal residues derivatized with a charged moiety and their respective ends of the probe. In some forms of the PNA probes, there can be independently five, six, or seven residues not derivatized with a charged moiety between each of the end-proximal residues derivatized with a charged moiety and their respective ends of the probe. In some forms of the PNA probes, there can be independently zero, one, or two residues not derivatized with a charged moiety between each of the end-proximal residues derivatized with a charged moiety and their respective ends of the probe. In some forms of the PNA probes, there can be independently five, six, or seven residues not derivatized with a charged moiety between each of the end-proximal residues derivatized with a charged moiety and their respective ends of the probe. In some forms of the PNA probes, there can be independently four, five, or six residues not derivatized with a charged moiety between each of the end-proximal residues derivatized with a charged moiety and their respective ends of the probe. In some forms of the PNA probes, there can be independently three, four, or five residues not derivatized with a charged moiety between each of the end-proximal residues derivatized with a charged moiety and their respective ends of the probe. In some forms of the PNA probes, there can be independently two, three, or four residues not derivatized with a charged moiety between each of the end-proximal residues derivatized with a charged moiety and their respective ends of the probe. In some forms of the PNA probes, there can be independently one, two, or three residues not derivatized with a charged moiety between each of the end-proximal residues derivatized with a charged moiety and their respective ends of the probe. In some forms of the PNA probes, there can be independently zero, one, or two residues not derivatized with a charged moiety between each of the end-proximal residues derivatized with a charged moiety and their respective ends of the probe. In some forms of the PNA probes, there can be independently six or seven residues not derivatized with a charged moiety between each of the end-proximal residues derivatized with a charged moiety and their respective ends of the probe. In some forms of the PNA probes, there can be independently five or six residues not derivatized with a charged moiety between each of the end-proximal residues derivatized with a charged moiety and their respective ends of the probe. In some forms of the PNA probes, there can be independently four or five residues not derivatized with a charged moiety between each of the end-proximal residues derivatized with a charged moiety and their respective ends of the probe. In some forms of the PNA probes, there can be independently three or four residues not derivatized with a charged moiety between each of the end-proximal residues derivatized with a charged moiety and their respective ends of the probe. In some forms of the PNA probes, there can be independently two or three residues not derivatized with a charged moiety between each of the end-proximal residues derivatized with a charged moiety and their respective ends of the probe. In some forms of the PNA probes, there can be independently one or two residues not derivatized with a charged moiety between each of the end-proximal residues derivatized with a charged moiety and their respective ends of the probe. In some forms of the PNA probes, there can be independently zero or one residues not derivatized with a charged moiety between each of the end-proximal residues derivatized with a charged moiety and their respective ends of the probe. In some forms of the PNA probes, there can be independently seven residues not derivatized with a charged moiety between each of the end-proximal residues derivatized with a charged moiety and their respective ends of the probe. In some forms of the PNA probes, there can be independently six residues not derivatized with a charged moiety between each of the end-proximal residues derivatized with a charged moiety and their respective ends of the probe. In some forms of the PNA probes, there can be independently five residues not derivatized with a charged moiety between each of the end-proximal residues derivatized with a charged moiety and their respective ends of the probe. In some forms of the PNA probes, there can be independently four residues not derivatized with a charged moiety between each of the end-proximal residues derivatized with a charged moiety and their respective ends of the probe. In some forms of the PNA probes, there can be independently three residues not derivatized with a charged moiety between each of the end-proximal residues derivatized with a charged moiety and their respective ends of the probe. In some forms of the PNA probes, there can be independently two residues not derivatized with a charged moiety between each of the end-proximal residues derivatized with a charged moiety and their respective ends of the probe. In some forms of the PNA probes, there can be independently one residue not derivatized with a charged moiety between each of the end-proximal residues derivatized with a charged moiety and their respective ends of the probe. In some forms of the PNA probes, there can be independently zero residues not derivatized with a charged moiety between each of the end-proximal residues derivatized with a charged moiety and their respective ends of the probe.

For example, the probe T*gTgC*cTccC*gTtTT*gTcC* (SEQ ID NO:6) has zero residues not derivatized with a charged moiety between the N-terminal end and its end-proximal derivatized residue and zero residues not derivatized with a charged moiety between the C-terminal end and its end-proximal derivatized residue, the probe cT*tCaT*CtCgT*cTaC*aaT*a (SEQ ID NO:10) has one residue not derivatized with a charged moiety between the N-terminal end and its end-proximal derivatized residue and one residue not derivatized with a charged moiety between the C-terminal end and its end-proximal derivatized residue, and the probe agT*CgTtC*tTcT*aTCaT*cT (SEQ ID NO:20) has two residues not derivatized with a charged moiety between the N-terminal end and its end-proximal derivatized residue and two residues not derivatized with a charged moiety between the C-terminal end and its end-proximal derivatized residue.

In some forms of the PNA probes, there are independently zero, one, two, three, or four residues not derivatized with a moiety between every residue derivatized with a moiety. In some forms of the PNA probes, there are independently one, two, three, or four residues not derivatized with a moiety between every residue derivatized with a moiety. In some forms of the PNA probes, there are independently zero, one, two, or three residues not derivatized with a moiety between every residue derivatized with a moiety. In some forms of the PNA probes, there are independently two, three, or four residues not derivatized with a moiety between every residue derivatized with a moiety. In some forms of the PNA probes, there are independently zero, one, or two residues not derivatized with a moiety between every residue derivatized with a moiety. In some forms of the PNA probes, there are independently three or four residues not derivatized with a moiety between every residue derivatized with a moiety. In some forms of the PNA probes, there are independently two or three residues not derivatized with a moiety between every residue derivatized with a moiety. In some forms of the PNA probes, there are independently one or two residues not derivatized with a moiety between every residue derivatized with a moiety. In some forms of the PNA probes, there are independently zero or one residues not derivatized with a moiety between every residue derivatized with a moiety. In some forms of the PNA probes, there are four residues not derivatized with a moiety between every residue derivatized with a moiety. In some forms of the PNA probes, there are three residues not derivatized with a moiety between every residue derivatized with a moiety. In some forms of the PNA probes, there are two residues not derivatized with a moiety between every residue derivatized with a moiety. In some forms of the PNA probes, there is one residue not derivatized with a moiety between every residue derivatized with a moiety. In some forms of the PNA probes, there are zero residues not derivatized with a moiety between every residue derivatized with a moiety.

In some forms of the PNA probes, there are independently at least one, two, three, or four residues not derivatized with a moiety between every residue derivatized with a moiety. In some forms of the PNA probes, there are independently at least one, two, or three residues not derivatized with a moiety between every residue derivatized with a moiety. In some forms of the PNA probes, there are independently at least one or two residues not derivatized with a moiety between every residue derivatized with a moiety. In some forms of the PNA probes, there is independently at least one residue not derivatized with a moiety between every residue derivatized with a moiety. In some forms of the PNA probes, there are independently at least two residues not derivatized with a moiety between every residue derivatized with a moiety. In some forms of the PNA probes, there are independently at least three residues not derivatized with a moiety between every residue derivatized with a moiety. In some forms of the PNA probes, there are independently no more than one, two, three, or four residues not derivatized with a moiety between every residue derivatized with a moiety. In some forms of the PNA probes, there are independently no more than one, two, or three residues not derivatized with a moiety between every residue derivatized with a moiety. In some forms of the PNA probes, there are independently no more than one or two residues not derivatized with a moiety between every residue derivatized with a moiety. In some forms of the PNA probes, there is independently no more than one residue not derivatized with a moiety between every residue derivatized with a moiety. In some forms of the PNA probes, there are independently no more than two residues not derivatized with a moiety between every residue derivatized with a moiety. In some forms of the PNA probes, there are independently no more than three residues not derivatized with a moiety between every residue derivatized with a moiety.

For example, the probe T*gTgC*cTccC*gTtTT*gTcC* (SEQ ID NO:6) has, at different locations, zero, one, or two residues not derivatized with a moiety between the residues derivatized with a moiety, the probe cT*tCaT*CtCgT*cTaC*aaT*a (SEQ ID NO:10) has, at different locations, zero, one, or two residues not derivatized with a moiety between the residues derivatized with a moiety, and the probe agT*CgTtC*tTcT*aTCaT*cT (SEQ ID NO:20) has, at different locations, zero or one residue not derivatized with a moiety between the residues derivatized with a moiety.

In some forms of the PNA probes, there are independently one, two, three, four, five, or six residues not derivatized with a charged moiety between every residue derivatized with a charged moiety. In some forms of the PNA probes, there are independently two, three, four, five, or six residues not derivatized with a charged moiety between every residue derivatized with a charged moiety. In some forms of the PNA probes, there are independently one, two, three, four, or five residues not derivatized with a charged moiety between every residue derivatized with a charged moiety. In some forms of the PNA probes, there are independently three, four, five, or six residues not derivatized with a charged moiety between every residue derivatized with a charged moiety. In some forms of the PNA probes, there are independently one, two, three, or four residues not derivatized with a charged moiety between every residue derivatized with a charged moiety. In some forms of the PNA probes, there are independently four, five, or six residues not derivatized with a charged moiety between every residue derivatized with a charged moiety. In some forms of the PNA probes, there are independently one, two, or, three residues not derivatized with a charged moiety between every residue derivatized with a charged moiety. In some forms of the PNA probes, there are independently four, five, or six residues not derivatized with a charged moiety between every residue derivatized with a charged moiety. In some forms of the PNA probes, there are independently three, four, or five residues not derivatized with a charged moiety between every residue derivatized with a charged moiety. In some forms of the PNA probes, there are independently two, three, or four residues not derivatized with a charged moiety between every residue derivatized with a charged moiety. In some forms of the PNA probes, there are independently one, two, or three residues not derivatized with a charged moiety between every residue derivatized with a charged moiety. In some forms of the PNA probes, there are independently five or six residues not derivatized with a charged moiety between every residue derivatized with a charged moiety. In some forms of the PNA probes, there are independently four or five residues not derivatized with a charged moiety between every residue derivatized with a charged moiety. In some forms of the PNA probes, there are independently three or four residues not derivatized with a charged moiety between every residue derivatized with a charged moiety. In some forms of the PNA probes, there are independently two or three residues not derivatized with a charged moiety between every residue derivatized with a charged moiety. In some forms of the PNA probes, there are independently one or two residues not derivatized with a charged moiety between every residue derivatized with a charged moiety. In some forms of the PNA probes, there are six residues not derivatized with a charged moiety between every residue derivatized with a charged moiety. In some forms of the PNA probes, there are five residues not derivatized with a charged moiety between every residue derivatized with a charged moiety. In some forms of the PNA probes, there are four residues not derivatized with a charged moiety between every residue derivatized with a charged moiety. In some forms of the PNA probes, there are three residues not derivatized with a charged moiety between every residue derivatized with a charged moiety. In some forms of the PNA probes, there are two residues not derivatized with a charged moiety between every residue derivatized with a charged moiety. In some forms of the PNA probes, there is one residue not derivatized with a charged moiety between every residue derivatized with a charged moiety.

In some forms of the PNA probes, there are independently at least one, two, three, four, or five residues not derivatized with a charged moiety between every residue derivatized with a charged moiety. In some forms of the PNA probes, there are independently at least one, two, three, or four residues not derivatized with a charged moiety between every residue derivatized with a charged moiety. In some forms of the PNA probes, there are independently at least one, two, or three residues not derivatized with a charged moiety between every residue derivatized with a charged moiety. In some forms of the PNA probes, there are independently at least one or two residues not derivatized with a charged moiety between every residue derivatized with a charged moiety. In some forms of the PNA probes, there is independently at least one residue not derivatized with a charged moiety between every residue derivatized with a charged moiety. In some forms of the PNA probes, there are independently at least two residues not derivatized with a charged moiety between every residue derivatized with a charged moiety. In some forms of the PNA probes, there are independently at least three residues not derivatized with a charged moiety between every residue derivatized with a charged moiety. In some forms of the PNA probes, there are independently at least four residues not derivatized with a charged moiety between every residue derivatized with a charged moiety. In some forms of the PNA probes, there are independently no more than one, two, three, four, five, or six residues not derivatized with a charged moiety between every residue derivatized with a charged moiety. In some forms of the PNA probes, there are independently no more than one, two, three, four, or five residues not derivatized with a charged moiety between every residue derivatized with a charged moiety. In some forms of the PNA probes, there are independently no more than one, two, three, or four residues not derivatized with a charged moiety between every residue derivatized with a charged moiety. In some forms of the PNA probes, there are independently no more than one, two, or three residues not derivatized with a charged moiety between every residue derivatized with a charged moiety. In some forms of the PNA probes, there are independently no more than one or two residues not derivatized with a charged moiety between every residue derivatized with a charged moiety. In some forms of the PNA probes, there is independently no more than one residue not derivatized with a charged moiety between every residue derivatized with a charged moiety. In some forms of the PNA probes, there are independently no more than two residues not derivatized with a charged moiety between every residue derivatized with a charged moiety. In some forms of the PNA probes, there are independently no more than three residues not derivatized with a charged moiety between every residue derivatized with a charged moiety. In some forms of the PNA probes, there are independently no more than four residues not derivatized with a charged moiety between every residue derivatized with a charged moiety. In some forms of the PNA probes, there are independently no more than five residues not derivatized with a charged moiety between every residue derivatized with a charged moiety. In some forms of the PNA probes, there are independently no more than six residues not derivatized with a charged moiety between every residue derivatized with a charged moiety.

For example, the probe T*gTgC*cTccC*gTtTT*gTcC* (SEQ ID NO:6) has, at different locations, three or four residues not derivatized with a charged moiety between the residues derivatized with a charged moiety, the probe cT*tCaT*CtCgT*cTaC*aaT*a (SEQ ID NO:10) has, at different locations, two, three, or four residues not derivatized with a charged moiety between the residues derivatized with a charged moiety, and the probe agT*CgTtC*tTcT*aTCaT*cT (SEQ ID NO:20) has, at different locations, three or four residues not derivatized with a charged moiety between the residues derivatized with a charged moiety.

In some forms of the PNA probes, there are independently an average of at or between about 0.4 to 1.6 residues not derivatized with a moiety between every residue derivatized with a moiety. In some forms of the PNA probes, there are independently an average of at or between about 0.5 to 1.5 residues not derivatized with a moiety between every residue derivatized with a moiety. In some forms of the PNA probes, there are independently an average of at or between about 0.4, 0.5, 0.6, 0.7, 0.8, 0.9, 1.0, 1.1, 1.2, 1.3, 1.4, or 1.5 to 0.5, 0.6, 0.7, 0.8, 0.9, 1.0, 1.1, 1.2, 1.3, 1.4, 1.5, or 1.6 residues not derivatized with a moiety between every residue derivatized with a moiety. In some forms of the PNA probes, there are independently an average of at or between about 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 01.42, 1.43, 1.44, 1.45, 1.46, 1.47, 1.48, 1.49, 1.50, 1.51, 1.52, 1.53, 1.54, 1.55, 1.56, 1.57, 1.58, 1.59, or 1.60 residues not derivatized with a moiety between every residue derivatized with a moiety.

The average of residues not derivatized with a moiety between every derivatized residue (that is, a residue derivatized with a moiety) can be calculated by adding together the number of residues in each gap between derivatized residues (including zero as the gap between immediately adjacent derivatized residues) and dividing by the number of gaps (including zero length gaps between immediately adjacent derivatized residues). Thus, for example, the probe T*gTgC*cTccC*gTtTT*gTcC* (SEQ ID NO:6) has nine gaps between ten derivatized residues (including the gap of zero length between the adjacent derivatized Ts), with the gaps between derivatized residues being of length 1, 1, 1, 2, 1, 1, 0, 1, and 1. This produces an average of residues not derivatized with a moiety between every derivatized residue of 9/9=1. As another example, the probe cT*tCaT*CtCgT*cTaC*aaT*a (SEQ ID NO:10) has eight gaps between nine derivatized residues (including the gap of zero length between the adjacent derivatized T and C), with the gaps between derivatized residues being of length 1, 1, 0, 1, 1, 1, 1, and 2. This produces an average of residues not derivatized with a moiety between every derivatized residue of 8/8=1. As another example, the probe agT*CgTtC*tTcT*aTCaT*cT (SEQ ID NO:20) has nine gaps between ten derivatized residues (including the gaps of zero length between the adjacent derivatized Ts and Cs), with the gaps between derivatized residues being of length 0, 1, 1, 1, 1, 1, 0, 1, and 1. This produces an average of residues not derivatized with a moiety between every derivatized residue of 7/9=0.78.

Alternatively, the average of residues not derivatized with a moiety between every derivatized residue can be calculated by subtracting the number of underivatized flanking residues (that is, flanking residues not derivatized with a moiety) and the number of derivatized residues from the total number of residues in the probe and dividing the result by one less than the number of derivatized residues in the probe. Thus, for example, the probe T*gTgC*cTccC*gTtTT*gTcC* (SEQ ID NO:6) has 19 total residues, 0 underivatized flanking residues, and 10 derivatized residues. This produces an average of residues not derivatized with a moiety between every derivatized residue of (19−0−10)/(10−1)=1. As another example, the probe cT*tCaT*CtCgT*cTaC*aaT*a (SEQ ID NO:10) has 19 total residues, 2 underivatized flanking residues, and 9 derivatized residues. This produces an average of residues not derivatized with a moiety between every derivatized residue of (19−2−9)/(9−1)=1. As another example, the probe agT*CgTtC*tTcT*aTCaT*cT (SEQ ID NO:20) has 19 total residues, 2 underivatized flanking residues, and 10 derivatized residues. This produces an average of residues not derivatized with a moiety between every derivatized residue of (19−2−10)/(10−1)=0.78.

In some forms of the PNA probes, there are independently an average of at or between about 0.9 to 6.0 residues not derivatized with a charged moiety between every residue derivatized with a charged moiety. In some forms of the PNA probes, there are independently an average of at or between about 1.0 to 5.0 residues not derivatized with a charged moiety between every residue derivatized with a charged moiety. In some forms of the PNA probes, there are independently an average of at or between about 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50, 2.51, 2.52, 2.53, 2.54, 2.55, 2.56, 2.57, 2.58, 2.59, 2.60, 2.61, 2.62, 2.63, 2.64, 2.65, 2.66, 2.67, 2.68, 2.69, 2.70, 2.71, 2.72, 2.73, 2.74, 2.75, 2.76, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.99, 3.00, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, or 5.9 to 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50, 2.51, 2.52, 2.53, 2.54, 2.55, 2.56, 2.57, 2.58, 2.59, 2.60, 2.61, 2.62, 2.63, 2.64, 2.65, 2.66, 2.67, 2.68, 2.69, 2.70, 2.71, 2.72, 2.73, 2.74, 2.75, 2.76, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.99, 3.00, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 residues not derivatized with a charged moiety between every residue derivatized with a charged moiety.

The average of residues not derivatized with a charged moiety between every residue derivatized with a charged moiety can be calculated by adding together the number of residues not derivatized with a charged moiety in each gap between residues derivatized with a charged moiety (including zero as the gap between immediately adjacent residues derivatized with a charged moiety) and dividing by the number of gaps (including zero length gaps between immediately adjacent residues derivatized with a charged moiety). Thus, for example, the probe T*gTgC*cTccC*gTtTT*gTcC* (SEQ ID NO:6) has four gaps between five residues derivatized with a charged moiety, with the gaps between derivatized residues being of length 3, 4, 4, and 3. This produces an average of residues not derivatized with a moiety between every derivatized residue of 14/4=3.5. As another example, the probe cT*tCaT*CtCgT*cTaC*aaT*a (SEQ ID NO:10) has four gaps between five residues derivatized with a charged moiety, with the gaps between derivatized residues being of length 3, 4, 3, and 2. This produces an average of residues not derivatized with a moiety between every derivatized residue of 12/4=3.0. As another example, the probe agT*CgTtC*tTcT*aTCaT*cT (SEQ ID NO:20) has three gaps between four residues derivatized with a charged moiety, with the gaps between derivatized residues being of length 4, 3, and 4. This produces an average of residues not derivatized with a moiety between every derivatized residue of 11/3=3.7.

Alternatively, the average of residues not derivatized with a charged moiety between every residue derivatized with a charged moiety can be calculated by subtracting the number of flanking residues not derivatized with a charged moiety and the number of residues derivatized with a charged moiety from the total number of residues in the probe and dividing the result by one less than the number of residues derivatized with a charged moiety in the probe. Thus, for example, the probe T*gTgC*cTccC*gTtTT*gTcC* (SEQ ID NO:6) has 19 total residues, 0 flanking residues not derivatized with a charged moiety, and 5 residues derivatized with a charged moiety. This produces an average of residues not derivatized with a charged moiety between every residue derivatized with a charged moiety of (19−0−5)/(5−1)=3.5. As another example, the probe cT*tCaT*CtCgT*cTaC*aaT*a (SEQ ID NO:10) has 19 total residues, 2 flanking residues not derivatized with a charged moiety, and 5 derivatized residues. This produces an average of residues not derivatized with a charged moiety between every residue derivatized with a charged moiety of (19−2−5)/(5−1)=3.0. As another example, the probe agT*CgTtC*tTcT*aTCaT*cT (SEQ ID NO:20) has 19 total residues, 4 flanking residues not derivatized with a charged moiety, and 4 residues derivatized with a charged moiety. This produces an average of residues not derivatized with a charged moiety between every residue derivatized with a charged moiety of (19−4−4)/(4−1)=3.7.

In some forms of the PNA probes, independently zero, one, or two purine residues are derivatized. In some forms of the PNA probes, independently zero or one purine residues are derivatized. In some forms of the PNA probes, independently zero purine residues are derivatized. In some forms of the PNA probes, no purine residues are derivatized.

In addition to PNA probe charge and length, the content of miniPEG modified chiral residues can also be optimized for any given application. In some forms an optimal 18-mer PNA probe can have 3, 4, or 5 gamma-mini-PEG modifications. In a particular form the use of 4 gamma-mini-PEG residues is the optimal compromise between yield and selectivity.

In an exemplary form, PNA probes include 18 or 19 bases. Preferably, the probes contain 3 or 4 or 5 residues having charged amino acid side chains, most preferably 4 or 5 residues having charged amino acid side chains. Preferably, the probes contain 1 or 2 or 3 or 4 or 5 or 6 or 7 or 8 or 9 or 10 or 11 or 12 or 13 or 14 residues having mini-PEGs. Probe performance can be related to hybridization, for example, the specificity and/or affinity of a probe for a specific nucleic acid sequence. In some forms, the probe performance is directly associated with the content of charged amino acids residues, directly associated the content of residues having mini-PEG modifications, or directly associated with the content of residues having charged amino acids and the content of residues having mini-PEG modifications. For example, the presence of an increased number of residues having charged amino acid side chains can increase specific hybridization of the probe relative to an equivalent PNA probe having a reduced number of residues having charged amino acid side chains. In some forms, the presence of residues having charged amino acid side chains has a greater impact upon probe performance than the presence of residues having mini-PEG modifications.

Non-limiting examples of preferred compositions for 18-base PNA probes containing several L-lysine or several L-thialysine residues are shown in Table 3, below.

TABLE 3

Exemplary PNA probe compositions of amino acid side chain/mini PEGs.

| SEQ. ID NO. | Sequence | Amino Acid Side Chain/PEG Content |
|---|---|---|
| 1 | nKnMnKnMnKnnMnKnMn | 4 monomers L-lysine and 4 mini-PEG monomers |
| 2 | nKnMnKnMnKnMnKnMnn | 4 monomers L-lysine and 4 mini-PEG monomers |
| 3 | nKnMnKnMnKnMnKnMnK | 5 monomers L-lysine and 4 mini-PEG monomers |
| 4 | nSnMnSnMnSnnMnSnMn | 4 monomers L-thialysine and 4 mini-PEG monomers |
| 5 | nSnMnSnMnSnMnSnMnn | 4 monomers L-thialysine and 4 mini-PEG monomers |
| 6 | nSnMnSnMnSnMnSnMnS | 5 monomers L-thialysine and 4 mini-PEG monomers |

TABLE 3-continued

Exemplary PNA probe compositions of amino acid side chain/mini PEGs.

| SEQ. ID NO. | Sequence | Amino Acid Side Chain/PEG Content |
|---|---|---|
| 7 | nKnMnKnMnKnnMnKnMn | 4 monomers L-lysine and 4 mini-PEG monomers |
| 8 | nKnMnKnMnKnMnKnMnn | 4 monomers L-lysine and 4 mini-PEG monomers |
| 9 | nKnMnKnMnKnMnKnMnK | 5 monomers L-lysine and 4 mini-PEG monomers |

"K" represents gamma-L-lysine chiral PNA monomer base;
"S" represents gamma-L-thialysine chiral PNA monomer base;
"n" represents standard (achiral) PNA monomer base; and
"M" represents gamma mini-PEG chiral PNA monomer base.

d. Exemplary PNA Probes

The probing sequence of nucleic acids within each PNA probe defines the nucleic acid sequence to which each probe will hybridize. Therefore, the probing nucleobase sequence of each probe defines the complementary nucleic acid sequence(s) targeted by the probe region (e.g., genomic DNA fragments) that will be enriched when hybridized to the probes as defined by the described methods.

Exemplary nucleobase probing sequences of PNA probes are provided in Table 4.

TABLE 4

Exemplary Nucleobase probing sequences and compositions of PNA probes

| Seq. ID No. | Probe Name | Probing Nucleobase Sequence | Probe Composition |
|---|---|---|---|
| 1 | C4902 | TCCCATGCACTTTTCGATT | Biotin-O-O-tC*ccAtgC*acT*ttT*cgA*tt |
| 2 | C5391 | CTTTTTACAGCCCGTCTCAC | Biotin-O-O-cT*ttT*taCagC*ccGtcT*caC* |
| 3 | C8925-6/1 | TTTATTTGGCGTTTGTAATT-KK | Biotin-O-O-T*ttA*ttT*ggCgtT*tgT*aaT*t-KK |
| 3 | C8926-4/3 | TTTATTTGGCGTTTGTAATT-KK | Biotin-O-O-T*ttAttT*ggCgtT*tgTaaT*t-KK |
| 4 | A2486 | TATCCGTATTACTTCTCTGG | Biotin-O-O-T*atCcgT*atT*acT*tcT*ctGg |
| 5 | A9827 | CAGGTATTCCTATCGTCCTT-KK | Biotin-O-O-C*agG*taT*tcCtaT*cgT*ccT*t-KK |

Probes Targeting the human major histocompatibility complex (MHC); All have 5 gamma-L-lysines

| 6 | 32526695 | TGTGCCTCCCGTTTTGTCC | Biotin-O-O-T*gTgC*cTccC*gTtTT*gTcC* |
| 7 | 32531919 | TGTCCGATTGTTCTTATAC | Biotin-O-O-T*gTcC*gaTT*gTtCtT*aTaC* |
| 8 | 32538455 | CTCGGCATGTATTTTGCTC | Biotin-O-O-C*tCggC*aTgT*aTTtT*gCtC* |
| 9 | 32542414 | CACTTGACCCTGCTCGCCT | Biotin-O-O-C*aCtT*gaCCcT*gCtC*gCcT* |
| 10 | 32546193 | CTTCATCTCGTCTACAATA | Biotin-O-O-cT*tCaT*CtCgT*cTaC*aaT*a |
| 11 | 32550859 | CTGCGTTCTTTGTACTATA | Biotin-O-O-cT*gCgT*TcT*tTgT*aCTaT*a |
| 12 | 32553907 | TCTCCGTATTTCCTCGCTA | Biotin-O-O-T*cTcC*gTaT*tTcC*tCgCT*a |
| 13 | 32560105 | ATAGTGTCTCGTTTACTTT | Biotin-O-O-aT*agTgT*cTC*gTtT*aCtT*t |

TABLE 4-continued

Exemplary Nucleobase probing sequences and compositions of PNA probes

| Seq. ID No. | Probe Name | Probing Nucleobase Sequence | Probe Composition |
|---|---|---|---|
| 14 | 32564701 | CTGTACCAACTTCTCAATC | Biotin-O-O-cT*gTaC*CaaC*TtC*tCaaT*c |
| 15 | 32570978 | CGCTGACTGTTACCACCCT | Biotin-O-O-C*gCTgaC*TgTT*acC*aCcC*t |
| 16 | 32576190 | CTGATTCACGCTCTACATT | Biotin-O-O-cT*gaTtC*aCgC*tCT*aCaT*t |
| 17 | 32580488 | TCTCGTATATTTTTCATGT | Biotin-O-O-tC*tCgT*aTaTT*tTtC*aTgT* |
| 18 | 32584472 | GTTAACTGTCCGTTTTTCT | Biotin-O-O-gT*TaaC*TgTcC*gTtT*tTcT* |
| 19 | 32592335 | GTTAACCGCACCTCTCTTC | Biotin-O-O-gT*TaaCC*gCaC*cTcT*cTtC* |
| 20 | 32592780 | AGTCGTTCTTCTATCATCT | Biotin-O-O-agT*CgTtC*tTcT*aTC*aTcT* |
| 21 | 32598489 | ATTACTTTTGCCGATGCCT | Biotin-O-O-aT*TaCtT*tTgC*CgaT*gCcT* |
| 22 | 32604915 | ACCCATCCCTCTTGCGACT | Biotin-O-O-aC*cCaT*cCcT*cTT*gCgaC*t |
| 23 | 32609311 | CTACAACTCTACCGCTGCT | Biotin-O-O-cT*aCaaC*TcT*acC*gCTgC*t |

Probes Targeting the human major histocompatibility complex (MHC); All have 4 gamma-L-lysines

| 6 | 32526695 | TGTGCCTCCCGTTTTGTCC | Biotin-O-O-T*gTgC*cTccC*gTtTT*gTcC |
| 7 | 32531919 | TGTCCGATTGTTCTTATAC | Biotin-O-O-T*gTcC*gaTT*gTtCtT*aTaC |
| 8 | 32538455 | CTCGGCATGTATTTTGCTC | Biotin-O-O-C*tCggC*aTgT*aTTtT*gCtC |
| 9 | 32542414 | CACTTGACCCTGCTCGCCT | Biotin-O-O-C*aCtT*gaCCcT*gCtC*gCcT |
| 10 | 32546193 | CTTCATCTCGTCTACAATA | Biotin-O-O-cT*tCaT*CtCgT*cTaC*aaTa |
| 11 | 32550859 | CTGCGTTCTTTGTACTATA | Biotin-O-O-cT*gCgT*TcTtT*gTaC*TaTa |
| 12 | 32553907 | TCTCCGTATTTCCTCGCTA | Biotin-O-O-T*cTcC*gTaT*tTcC*tCgCTa |
| 13 | 32560105 | ATAGTGTCTCGTTTACTTT | Biotin-O-O-aT*agTgT*cTCgT*tTaC*tTt |
| 14 | 32564701 | CTGTACCAACTTCTCAATC | Biotin-O-O-cT*gTaC*CaaC*TtCtC*aaTc |
| 15 | 32570978 | GCTGACTGTTACCACCCT | Biotin-O-O-C*gCTgaC*TgTT*acCaC*cCt |
| 16 | 32576190 | CTGATTCACGCTCTACATT | Biotin-O-O-cT*gaTtC*aCgC*tCTaC*aTt |
| 17 | 32580488 | TCTCGTATATTTTTCATGT | Biotin-O-O-tC*tCgT*aTaTT*tTtC*aTgT |
| 18 | 32584472 | GTTAACTGTCCGTTTTTCT | Biotin-O-O-gT*TaaC*TgTcC*gTtT*tTcT |
| 19 | 32592335 | GTTAACCGCACCTCTCTTC | Biotin-O-O-gT*TaaCC*gCaC*cTcT*cTtC |
| 20 | 32592780 | AGTCGTTCTTCTATCATCT | Biotin-O-O-agT*CgTtC*tTcT*aTCaT*cT |
| 21 | 32598489 | ATTACTTTTGCCGATGCCT | Biotin-O-O-aT*TaCtT*tTgC*CgaT*gCcT |
| 22 | 32604915 | ACCCATCCCTCTTGCGACT | Biotin-O-O-aC*cCaT*cCcT*cTTgC*gaCt |
| 23 | 32609311 | CTACAACTCTACCGCTGCT | Biotin-O-O-cT*aCaaC*TcT*acCgC*TgCt |

Probes Targeting the human MHC FOXP3 (Forkhead Box P3, expressed in regulatory T-cells)

| 24 | 49109870 | TTACTCCGCTTCTTTTCAA | Biotin-O-O-tT*aCtC*cgC*tTcT*tTtC*aa |
| 25 | 49114104 | CCATTCACCGTCCATACCT | Biotin-O-O-cC*aTtC*acCgT*cCaT*aCcT* |
| 26 | 49119924 | ATTCCGGTTGTTTCTCGTT | Biotin-O-O-aT*tcC*ggTT*gTttC*tCgT*t |
| 27 | 49123871 | TCCTGACCCGTTTAATCTT | Biotin-O-O-tC*cTgaC*cCgT*tTaaT*cT*t |
| 28 | 49128917 | CTTTACTCTTATCCCGTAA | Biotin-O-O-cT*tTaC*tCtT*atC*cCgT*aa |

TABLE 4-continued

Exemplary Nucleobase probing sequences
and compositions of PNA probes

| Seq. ID No. | Probe Name | Probing Nucleobase Sequence | Probe Composition |
|---|---|---|---|
| 29 | 49132435 | ACTTGTCCCGTTCAACTCC | Biotin-O-O-aC*tTgT*ccC*gTtC*aaCtC*c |
| 30 | 49136588 | GTCCCTATGCTAACCCTCT | Biotin-O-O-gT*cCcT*aTgC*TaaC*cCtC*t |
| Probes Targeting the human Mitochondrial genome | | | |
| 31 | 3491 | ACCCGCCACATCTACCATC | Biotin-O-O-aC*cCgC*CaCaT*cTaC*CaT*c |
| 32 | 5467 | CACGCTACTCCTACCTATC | Biotin-O-O-C*aCgC*TaCtC*cTaC*cTaT*c |
| 33 | 11848 | CTCGCTAACCTCGCCTTAC | Biotin-O-O-C*tCgC*TaaC*cTcgC*ctTaC* |
| 34 | 15188 | ACTTACTATCCGCCATCCC | Biotin-O-O-aC*tTaC*TaT*cCgC*CaTcC*c |

For probe composition, standard nucleobase PNA residues are provided in lowercase font (a, c, t, g); PNA residues modified with gamma-miniPEg base are provided in uppercase font (A, C, T, G); PNA residues modified with gamma-L-Lysine or gamma-L-thiolysine are provided in uppercase font followed by asterisks (A*, C*, T*, G*).

2. Single-Strand DNA Binding Protein

Single-stranded DNA-binding proteins (SSB) are also described. Single strand-binding protein (SSB) can facilitate double-stranded DNA invasion by a PNA hybridization probe.

Single-stranded DNA-binding proteins (SSB) can increase stability of a double-stranded DNA-PNA complex. For example, SSB can facilitate hybridization by a conventional (achiral) PNA probe (Ishizuka et al., 2009; Ishizuka & Tedeschi, 2009). The PNA and SSB form a double-stranded DNA-PNA-SSB complex that stabilizes the single-stranded DNA not bound to PNA. Therefore, the use of a reaction buffer containing the bacterial single-strand binding protein (SSB) improves the efficiency and specificity of PNA strand invasion by PNA probes that hybridize only to one strand of the target DNA. Exemplary SSB proteins are derived from organisms including Escherichia coli (E. coli), and Thermus aquaticus (Taq). Single-stranded DNA Binding Protein (SSB) to final concentration of 2 M. The concentration of SSB in solution can be optimized according to the needs of the experiment. SSB is commercially available from a number of sources, such as from SIGMA (catalogue number: S3917). Typically, SSB is present at a concentration from about 0.01 μM to 100 μM, inclusive. A preferred concentration of SSB is 2-3 μM.

3. Nucleic Acid Samples

For the disclosed methods, samples generally can be collected and/or obtained in any of the manners and modes in which nucleic samples are collected and obtained.

By "sample" is intended any sampling of nucleic acids. Any nucleic acid sample can be used with the disclosed methods. Examples of suitable nucleic acid samples include genomic samples, mRNA samples, cDNA samples, nucleic acid libraries (including cDNA and genomic libraries), whole cell samples, environmental samples, culture samples, tissue samples, bodily fluids, and biopsy samples. Numerous other sources of nucleic acid samples are known or can be developed and any can be used with the disclosed method. Preferred nucleic acid samples for use with the disclosed method are nucleic acid samples of significant complexity such as genomic samples and dsDNA libraries created by enzymatic or mechanical cleavage of genomic DNA.

Methods for collecting various bodily or cellular samples and for extracting nucleic acids are well known in the art. For example, nucleic acids can be obtained from cells, tissues, or bodily fluids containing nucleic acid. Examples of bodily samples include, but are not limited to, blood, lymph, urine, gynecological fluids, and biopsies. Bodily fluids can include blood, urine, saliva, or any other bodily secretion or derivative thereof. Blood can include whole blood, plasma, serum, or any derivative of blood. The sample can include cells, particularly eukaryotic cells from swabs and washings or tissue from a biopsy. Samples can be obtained from a subject by a variety of techniques including, for example, by scraping, washing, or swabbing an area, by using a needle to aspirate bodily fluids, or by removing a tissue sample (i.e., biopsy).

In some forms, the nucleic acid sample is genomic DNA, such as human genomic DNA. Human genomic DNA is available from multiple commercial sources (e.g., Coriell #NA23248). Typically, genomic DNA nucleic acid samples include native dsDNA. Therefore, samples can include non-denatured DNA, including dsDNA that has never been completely denatured (i.e., never-denatured DNA) or never been substantially or partially denatured (i.e., never substantially denatured DNA), or mixtures of denatured and non-denatured DNAs. In some forms, nucleic acid samples include non-natural DNA, (i.e., synthetic DNA), that may include mixture of double and single-stranded DNA. Nucleic acid fragments are segments of larger nucleic molecules. Nucleic acid fragments, as used in the disclosed method, generally refer to nucleic acid molecules that have been cleaved. A nucleic acid sample that has been incubated with a nucleic acid cleaving reagent is referred to as a digested sample. A nucleic acid sample that has been digested using a restriction enzyme is referred to as a digested sample. Therefore, nucleic acid samples can be genomic DNA, such as human genomic DNA (including a mixture including human nuclear and mitochondrial DNA), or any digested or cleaved sample thereof. In some forms, the nucleic acid sample contains one or more genomic DNA fragments of interest. Exemplary nucleic acid fragments have a length of approximately 2 kb, approximately 10 kb, approximately 15 kb, approximately 20 kb, approximately 25 kb, approximately 30 kb, approximately 35 kb, or approximately 40 kb.

B. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits for the sequence-specific capture and enrichment of long double stranded DNA strands according to the disclosed methods. Typically, kits include one or more sets of PNA probes specific to a DNA sequence. For example, kits for the simultaneous capture of one or more specific DNA sequences for a genome include a multiplicity of different sets of matched PNA hybridization probes, each probe being complementary to a corresponding target sequence in the genome. In some forms, kits for genomic DNA capture can be customized to include one or more sets of PNA hybridization probes custom-designed to capture the desired genomic DNA fragments.

Kits can contain any means for fragmenting DNA. Apparatus for DNA fragmentation is known in the art and includes ultra-sonicators, such as the Covaris Focused-ultrasonicator.

The kits also can contain apparatus suitable for capture and affinity-purification of the PNA-DNA complexes. Suitable apparatus can include an affinity-binding column. The affinity binding column can contain a suitable substrate matrix coupled to a capture dock specific for a capture tag on one or more PNA hybridization probes. Preferably, the affinity-binding column facilitates simplified washing and handling of the fragments, and allows automation of all or part of the method. Kits also can contain any other apparatus that provides a convenient means of washing away or otherwise separating undesirable reaction components from the target DNA/PNA complexes. An exemplary material for separation of PNA/DNA complexes and unbound PNA probes is polyacrylamide, for example in the form of beads. Polyacrylamide beads suitable for separation of unbound PNA probes are available from multiple commercial sources (e.g., Biogel P100, available from BioRad catalogue number 150-4170). Therefore, kits can include a column containing Biogel P100.

Kits can contain substrates in any useful form, including thin films or membranes, beads, bottles, dishes, fibers, woven fibers, shaped polymers, particles and microparticles. In some forms, kits contain substrates in the form of magnetic beads, for example, streptavidin coated paramagnetic beads (e.g., DYNABEADS® M280 streptavidin, available from Thermo-Fisher Life Technologies catalogue number 112.05D; 112.06D or 602.10). Kits can also contain the buffers and reagents required to couple nucleic acids, wash the bound complexes and elute nucleic acids from the substrates. An exemplary buffer for coupling and washing includes 10 mM Tris-HCl (pH 7.5), 1 mM EDTA, 2 M NaCl. Kits can also include other buffers and reagents that are commercially available from multiple sources (e.g., DYNABEADS® Kilobase BINDER™ kit, available from Thermo-Fisher Life Technologies catalogue number 60101). When magnetic beads are used, kits can also include suitable means for isolating the magnetic beads, such as a magnet.

Kits also can contain chemical reagents necessary for immobilizing and coupling capture docks to substrates according to any method established in the art.

Exemplary attachment agents include cyanogen bromide, succinimide, aldehydes, tosyl chloride, avidin-biotin, photo-crosslinkable agents, epoxides and maleimides.

The disclosed kits can also include single stranded binding protein (SSB). The SSB can be provided as an aliquot in a vessel and can be in an amount sufficient to stabilize the complex formed by interaction between a target DNA and the sequence-specific PNA.

In some forms, kits are designed to contain one or more sets of reagents suitable for the target-specific enrichment of one or more components of a specific genome, for example, the human genome. Exemplary human genomic DNA that can be targeted and enriched using the described kits includes DNA located in the MHC region. For example, in particular forms, kits include PNA probe sets designed to capture up to 7 mega-bases of human genomic DNA located in the Major Histocompatibility Complex (MHC) region of chromosome 6.

In some forms, kits include PNA probe sets designed to capture genomic components of the MHC known to be associated with one or more specific immunological features or phenotypes. Exemplary immunological features or phenotypes include having predisposition to autoimmune diseases, or showing symptoms of autoimmune diseases. Therefore, in some forms, kits include PNA probes that selectively enrich genomic DNA including regions where sequence variation is associated with immunological features such as autoimmune diseases. Exemplary genes associated with sequence variation relating to autoimmune diseases include, among others, the DRB1 and DQA1 genes. Therefore, in some forms, kits include PNA probes that enrich genomic DNA fragments including the DRB1 gene, or fragments of the DRB1 gene. In some forms, kits include PNA probes that enrich genomic DNA fragments including the DQA1 gene, or fragments of the DQA1 gene. In some forms, kits include PNA probes that enrich genomic DNA fragments including the DQA1 gene, or fragments of the DQA1 gene and the DRB1 gene, or fragments of the DRB1 gene. An exemplary genomic target region is 90,000 bases in length and spans the genomic coordinates chr6:32522981-32612981 (coordinates based on human genome build hg19). In some forms, kits that enrich human genomic DNA located in the Major Histocompatibility Complex (MHC) region of chromosome 6, for example, kits targeting the DRB1 and DQA1 genes, include one or more probes having nucleobase probing sequences of SEQ ID Nos. 6-23.

In some forms, kits target the, a 40,000 base window that spans a region starting at −22,000 bases upstream of the human FOXP3 (Forkhead Box P3, expressed in regulatory T-cells) promoter, and ending 18,000 bases downstream of the FOXP3 promoter. Therefore, in some forms the kits target human genomic DNA including the FOXP3 gene, or fragments of the FOXP3 gene. An exemplary genomic target region is the sequence spanning the genomic coordinates chrX:49103288-49143288 (coordinates based on human genome build hg19). An exemplary kit for enriching genomic DNA from this region uses a total of seven probes, separated from each other by an average of 5,714 base pairs in the genome. In some forms, kits that enrich human genomic DNA located in the region of the human FOXP3 promoter, include one or more probes having nucleobase probing sequences of SEQ ID Nos. 24-30. In some forms, kits that target the FOX3 gene and components of the FOX3 gene include seven PNA probes having nucleobase probing sequences of SEQ ID Nos. 24-30.

In some forms, kits include PNA probe sets designed to capture genetic elements associated with one or more diseases or conditions, or having a known correlation with development of one or more disease or conditions (i.e., associated with disease risk). Exemplary diseases are autoimmune diseases, diabetes, and the metabolic syndrome, and cancer. For example, in a particular form, kits include PNA probe sets designed to capture up to 40 mega-bases of human genomic DNA located at different positions, and mapping to a multiplicity of enhancer elements associated with disease risk for autoimmune diseases. In some forms, kits include PNA probe sets designed to capture up to 40 mega-bases of human genomic DNA located at different positions, and mapping to a multiplicity of enhancer elements associated with disease risk for diabetes and the metabolic syndrome. In some forms, kits include PNA probe sets designed to capture up to 50 mega-bases of human genomic DNA located at different positions, and mapping to a multiplicity of enhancer elements associated with the differentiation of different subsets of white blood cells. For example, in some forms, kits include PNA probe sets designed to capture enhancer clusters associated with important diseases, such as Type II diabetes. 3,677 enhancer clusters have been identified which mapped near genes with strong pancreatic islet-enriched expression (Pasquali et al., *Nat Genet.* 2014 February; 46(2):136-43 (2014)). Therefore, in some forms, kits include PNA probes that capture genomic DNA windows of 30,000 to 150,000 base pairs to encompass all of the enhancers within a cluster. For example, kits can include PNA probes of unique sequence at an average distance of 5,000 to 7,000 bases from each other within each cluster.

In some forms, kits include PNA probe sets designed to capture entire subsets of genomic DNA from a single genome, or mixtures of two or more genomes from the same or different species, such as mitochondrial DNA. For example, in a particular form, kits include PNA probe sets designed to capture the entire human mitochondrial genome.

In some forms, kits that enrich human genomic DNA corresponding to some or all of the human mitochondrial genome include one or more probes having nucleobase probing sequences of SEQ ID Nos. 31-34. In some forms, kits that that enrich human genomic DNA corresponding to some or all of the human mitochondrial genome include four PNA probes having nucleobase probing sequences of SEQ ID Nos. 31-34.

In some forms, kits include PNA probe sets designed to capture the entire dog mitochondrial genome. In some forms, kits include PNA probe sets designed to capture the entire cat mitochondrial genome. In further forms, kits include PNA probe sets designed to capture genomic DNA of one or more species of bacteria, archaea, fungi, protozoa, or mixtures of two or more of these. Therefore, kits can include PNA probes and/or other reagents to capture genomic DNA of one or more species of bacteria present in the human oral cavity, one or more species of bacteria present in the human airway, or present in the human urogenital tract, or known to exist in human blood or feces. For example, in a particular form, kits include PNA probe sets designed to capture genomic DNA of 20 or more species of bacteria present in the human oral cavity. In a further form, kits include PNA probe sets designed to capture genomic DNA of 20 or more species of bacteria present in human feces.

C. Mixtures

It has been established that the use of a high multiplicity of short hybridization probe molecules enables capture of many different genomic DNA domains simultaneously. Disclosed are mixtures formed by performing or preparing to perform the disclosed methods.

1. Mixtures of Two or More Hybridization Probes

For example, disclosed are mixtures including one or more sets of hybridization probes designed to target a specific DNA sequence. Typically, a set of hybridization probes include at least two probes targeting non-identical nucleotide sequences. Preferably, each of the hybridization probes is a PNA probe including at least one PNA modified with a positive charge, such as a gamma-lysine PNA and at least one PNA modified with a neutral short-chain oligomer, such as a gamma-mini-PEG PNA.

Mixtures including at least two different PNA hybridization probes are provided. For example, the mixtures can include three or more hybridization probes complementary to non-overlapping sequences within a single genomic DNA fragment of interest. Exemplary dsDNA fragments have a length of approximately 2 kb, approximately 10 kb, approximately 15 kb, approximately 20 kb, approximately 25 kb, approximately 30 kb, approximately 35 kb, or approximately 40 kb.

In a particular form, mixtures include a multiplicity of hybridization probes designed to selectively capture genomic regions of interest from a DNA sample prior according to the disclosed methods. For example, mixtures including two or more gene-specific probes can target one or more specific genes from the human genome. In some forms, mixtures include sets of hybridization probes designed to target any one of the 20,000 genes of the human genome. In some forms, mixtures include sets of hybridization probes designed to target more than one of the 20,000 genes of the human genome. In some forms, the mixture includes approximately 40,000 hybridization probes, designed to selectively capture all of the 20,000 genes of the human genome. In some forms, a set of approximately 18,000 PNA hybridization probes are designed to target 6,000 different regions of the human genome that contain enhancers relevant to a specific disease. In some forms, a set of approximately 16 different PNA hybridization probes is designed to target the human mitochondrial DNA. In this case a high multiplicity of probes is utilized to ensure the capture of the 16 kb mitochondrial DNA, even in the event that multiple mitochondrial DNA mutations are present in the biological sample.

In order to use a multiplicity of PNA probes in a single mixture it is preferred that all the probe sequences in the set are unable to hybridize with each other. Therefore, mixtures preferably include combinations of PNA probe pairs having at least 3 mismatched bases, or more preferably at least 4 mismatches, or more preferably at least 5 mismatches, or even more preferably at least 6 mismatches.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

D. Systems

Disclosed are systems useful for performing, or aiding in the performance of, the disclosed method. Systems generally include combinations of articles of manufacture such as structures, machines, devices, and the like, and compositions, compounds, materials, and the like. Such combinations that are disclosed or that are apparent from the disclosure are contemplated. For example, disclosed and contemplated are systems including a device for processing nucleic acid samples and enriching for sequence-specific dsDNA fragments and a device for determining the nucleic acid sequence of the fragment, optionally including and assessing secondary structural characteristics, such as detecting the methylation state of the nucleic acids. As another example, disclosed and contemplated are systems including an automated device for fragmenting genomic nucleic acid samples and detecting the sequence and optionally the methylation state of specific nucleic acid fragments.

1. Data Structures and Computer Control

Disclosed are data structures used in, generated by, or generated from, the disclosed method. Data structures generally are any form of data, information, and/or objects collected, organized, stored, and/or embodied in a composition or medium. For example, the nucleotide sequence of a large dsDNA fragment associated with a specific target sequence or hybridization probe(s), and the methylation profile, or set of sequences and associated methylation states stored in electronic form, such as in RAM or on a storage disk, is a type of data structure. The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Uses

The disclosed methods and compositions are applicable to numerous areas including, but not limited to, the enrichment of a multiplicity of genomic DNA regions by capturing very long double-stranded DNA molecules. Other uses include sequence analysis of the very long DNA molecules and production of phased haplotypes. Other uses include analysis of the native methylation status of the very long DNA molecules and production of phased hepitypes. Other uses are disclosed, apparent from the disclosure, and/or will be understood by those in the art.

Methods for capturing long DNA molecules for harnessing the special utility of long DNA reads are provided. The sequence-specific capture of long DNA strands enables construction of phased haplotypes, which consist of sequence assemblies that correspond to a single DNA strand, either a pure paternal strand, or alternatively a pure maternal strand.

Therefore, the methods can include production of phased haplotypes. Phased haplotypes can include an ordered set of single nucleotide polymorphisms (SNPs) that contain valuable genetic information about the genetic linkage structure of genetically determined variability, over long distances in the human genome.

One of the most efficient methods yet reported for the construction of Whole-genome phased haplotypes is Statistically Aided Long Read Haplotyping (SLRH, Kuleshov et al., 2014). SLRH is a form of dilution haplotyping that involves placing a small number of large ~7- to 10-kbp DNA fragments into separate pools. Each pool is fitted with a unique barcode that identifies its fragments, which are then recovered from short-read sequences and assembled into long haplotype blocks using a phasing algorithm. Libraries of pooled, bar coded DNA fragments are sequenced. The sequenced reads are then aligned to the reference genome and mapped back to their original wells as specified by the barcode adapters. Mapped reads within each well are clustered into groups that are believed to come from the same fragment. A haplotyping algorithm, Prism, was developed to which augment the efficacy and accuracy of dilution haplotyping with statistical techniques. Using SLRH, Kuleshov et al. (2014) demonstrated the phasing of 99% of single-nucleotide variants in three human genomes into long haplotype blocks 0.2-1 Mbp in length.

Just as SNPs can be ordered by phasing of long DNA sequencing reads, it is possible, in theory, to assemble phased "Hepitypes." The term "Hepitype", by analogy to haplotype, is an ordered set of positions of variable Cytosine methylation status (methylated or unmethylated) that contains valuable epigenetic information about the epigenetic linkage structure of epigenetically determined variability, over relatively long distances in the human genome. Almost all prior technique for DNA methylation sequencing yield sequencing reads no longer than 250 base pairs.

Utilizing the Roche FLX system, Herrmann et al. (2011) performed a series of DNA methylation sequencing experiments where the average read length was 204 base pairs, allowing them to obtain phased methylation information sufficient to construct relatively short "Hepitypes". These hepitypes provided data of utility in the study phylogenetic traces of somatic evolution in colon cancer and in follicular lymphomas. The phased DNA methylation information was used to construct phylogentic trees of cancer developmental changes that resulted in alterations in DNA methylation patterns in the cancer cells. Phylogenetic trees were fitted using maximum-parsimony methods as implemented in Phylip 3.69 (internet site evolution.gs.washington.edu/phylip.html) with de-fault parameters.

A more recent study utilized large scale short-read methylation data from two cell lines (human embryonic stem cells and differentiated lung fibroblasts) to generate phased hepitypes associated with thousands of different SNP loci across the human genome (Chung et al., 2013). This study was based on data obtained by bisulfite sequencing, and therefore the phased hepitypes encompassed distances shorter than 100 bp. The longest hepitype found in this study was 89 bp in chr12, which included 10 cytosine positions that may be methylated or unmethylated differentially as cells replicate. Another observed hepitype included 95 base pairs in chr2 and included 6 cytosine positions which may be methylated or unmethylated. The reported hepitypes are shorter than traditionally defined haplotypes due to the short sequencing reads.

A fundamental property of long, double stranded DNA capture according to the described methods is the ability to easily substitute a capture target sequence (and a corresponding probe) for another, present within the same long DNA genomic domain, which typically ranges from 2,000 to 40,000 base pairs in length.

The disclosed methods include the determination, identification, correlation, etc. (which can be referred to collectively as "identifications") of nucleic acid samples, states, etc., based on measurements, detections, comparisons, analyses, assays, screenings, etc.

For example, the disclosed methods can be used to generate nucleic acid sequence information databases for the identification of phased haplotypes and phased hepitypes (also called epi-haplotypes) from genomic DNA. Such identifications are useful for many reasons. For example, and in particular, such identifications allow specific actions to be taken based on, and relevant to, the particular identification made. For example, diagnosis of a particular epi-haplotype in a tissue sample. In certain instances a particular epihaplotype may be indicative of a disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods including taking particular actions following and based on the disclosed identifications. For example, disclosed are methods including creating a record of an identification, such as an identification based upon nucleic acid sequence information that includes, for example, base modification information over long distances in a maternal or a paternal chromosome (in physical—such as paper, electronic, or other—form, for example), or creating a database, such as an electronic database. Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could compile, process, catalogue or treat, monitor, follow-up, advise, etc. based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods including making one or more further identifications based on one or more other identifications. For example, particular diagnosis, treatments, monitorings, follow-ups, advice, etc. can be identified based on the other identification. For example, identification of a particular base modification pattern, including a DNA methylation pattern that can be indicative of a sample or subject having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods including treating, monitoring, following-up with, advising, etc., a subject identified from analysis of nucleic acids by the disclosed methods. Accordingly, subjects can be identified as needing treating, monitoring, following-up with, advising, etc. by analysis according to any of the disclosed methods of nucleic acid samples taken from the subject. For example, particular treatments, monitorings, follow-ups, advice, etc., can be used based on identification and/or based on a record of identification. For example, a subject identified as having a disease or condition with a high level of a particular component or characteristic (and/or a subject for which a record has been made of such identification) can be treated with a therapy based on or directed to the high level component or characteristic. An example of a high level component is a high frequency of heteroplasmy (the presence of different mutated DNA sequences within a single biological sample) in mitochondrial DNA captured and then sequenced according to the disclosed methods. Another example of a high level component is a high level of hypomethylation (loss of methylation, often associated with transcriptional activation) in captured DNA fragments. Such hypomethylation can be detected, for example, in captured DNA fragments corresponding to particular Human Endogenous Retrovirus (HERV) sequences captured and sequenced to reveal base modifications according to the disclosed methods. Such treatments, monitoring, follow-ups, advice, etc. can be based, for example, directly on identifications, a record of such identifications, or a combination. Such treatments, monitoring, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc., can be combined with any one or more other methods disclosed herein, and in particular, with any one or more steps of the disclosed methods of identification.

Methods

A. Methods for Isolating Large Sequence-Specific Fragments of dsDNA

1. Genomic DNA Capture

Methods to capture, isolate and characterize a multiplicity of long double stranded DNA regions from genomic DNA, or equally well from a DNA sequencing library constructed with long DNA fragments have been developed. The methods enable purification of specific DNA sequences, or isolation of selected classes of DNA sequences from a mixture of DNA fragments, such as a genomic DNA library. The methods overcome roadblocks for mapping and sequencing genomic DNA such as the presence of repeated DNA sequences.

As used herein, the term "monitoring" as used herein refers to any method in the art by which an activity can be measured.

As used herein, the term "providing" as used herein refers to any means of adding a compound or molecule to something known in the art. Examples of providing can include the use of pipettes, syringes, needles, tubing, guns, etc. This can be manual or automated. It can include transfection by any means or any other means of providing nucleic acids to dishes, cells, tissue, cell-free systems and can be in vitro or in vivo.

As used herein, the term "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

A cell can be in vitro. Alternatively, a cell can be in vivo and can be found in a subject. A "cell" can be a cell from any organism including, but not limited to, a bacterium.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to their target sequence in a nucleic acid fragment, thereby forming nucleic acid fragments bound by PNA probes; (c) capturing the nucleic acid fragments bound by PNA probes via the capture tag and removing the uncaptured components of the reaction mix from the captured nucleic acid fragments bound by PNA probes; and (d) eluting the captured nucleic acid fragments from the PNA probes to form an enriched nucleic acid sample. This form of the method can thus result in nucleic acid fragments targeted by the PNA probes being enriched in the enriched nucleic acid sample as compared to the first nucleic acid sample. In this form of the method, the PNA probes in the same set of two or more PNA probes are designed to target a different sequence in the same nucleic acid fragment, the PNA probes in different sets of two or more PNA probes are designed to target different nucleic acid fragments, and the PNA probes each include one or more capture tags. In some forms, the step of capturing the nucleic acid fragments bound by PNA probes via the capture tag also captures the unbound PNA probes. In some forms, the method can also include, following step (b) and prior to step (c), removing unbound PNA probes from the reaction mix. In some forms, the method can also include, simultaneous with capturing the nucleic acid fragments bound by PNA probes, capturing unbound PNA probes via the capture tag.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to their target sequence in a nucleic acid fragment, thereby forming nucleic acid fragments bound by PNA probes; (c) removing unbound PNA probes from the reaction mix; (d) capturing the nucleic acid fragments bound by PNA probes via the capture tag and removing the uncaptured components of the reaction mix from the captured nucleic acid fragments bound by PNA probes; and (e) eluting the captured nucleic acid fragments from the PNA probes to form an enriched nucleic acid sample. This form of the method can thus result in nucleic acid fragments targeted by the PNA probes being enriched in the enriched nucleic acid sample as compared to the first nucleic acid sample. In this form of the method, the PNA probes in the same set of two or more PNA probes are designed to target a different sequence in the same nucleic acid fragment, the PNA probes in different sets of two or more PNA probes are designed to target different nucleic acid fragments, and the PNA probes each include one or more capture tags.

In some forms, the method involves (a) bringing into contact one or more sets of two or more peptide nucleic acid (PNA) hybridization probes with a first nucleic acid sample to form a reaction mix; (b) incubating the reaction mix under conditions that allow target-specific strand invasion binding by the PNA probes to their target sequence in a nucleic acid fragment, thereby forming nucleic acid fragments bound by PNA probes; (c) capturing both the nucleic acid fragments bound by PNA probes via the capture tag and the unbound PNA probes via the capture tag and removing the uncaptured components of the reaction mix from the captured nucleic acid fragments bound by PNA probes; and (d) eluting the captured nucleic acid fragments from the PNA probes to form an enriched nucleic acid sample. In these forms, the unbound PNA probes are separated from the nucleic acid fragments bound by PNA probes by elution of the captured nucleic acid fragments but not the captured unbound PNA probes. The unbound PNA probes remain captured when the captured nucleic acid fragments are eluted. In some forms, the step of eluting the captured nucleic acid fragments from the PNA probes is enhanced by the addition of one or more agents or conditions that enhance the release of captured dsDNA from the PNA probes.

In some forms, the method can include (a) bringing into contact one or more sets of two or more PNA probes of any one of claims 68 to 128 with a first nucleic acid sample to form a reaction mix; (b) incubating the reaction mix under conditions that allow target-specific strand invasion binding by the PNA probes to their target sequence in a nucleic acid fragment, thereby forming nucleic acid fragments bound by invading PNA probes; (c) capturing the nucleic acid fragments bound by PNA probes via the capture tag and removing the uncaptured components of the reaction mix from the captured nucleic acid fragments bound by PNA probes; (d) eluting the captured nucleic acid fragments from the PNA probes to form an enriched nucleic acid sample, where nucleic acid fragments targeted by the PNA probes are enriched in the enriched nucleic acid sample as compared to the first nucleic acid sample.

In some forms of the method, the PNA probes each include one or more capture tags, where at least one of the PNA probes includes one or more peptide nucleic acid residues that are derivatized with a charged moiety on the alpha carbon, beta carbon, gamma carbon, or combinations thereof and one or more peptide nucleic acid residues that are derivatized with a neutral moiety on the alpha carbon, beta carbon, gamma carbon, or combinations thereof.

In some forms of the method, the PNA probes in at least one of the sets of two or more PNA probes has 18 or 19 peptide nucleic acid residues, where at or between three to five of the peptide nucleic acid residues of the PNA probes in the at least one of the sets of two or more PNA probes are derivatized with the charged moieties, where the charged moieties are selected from the group consisting of gamma-L-lysine PNA, gamma-L-thialysine PNA, and combinations thereof, where at or between two to six of the peptide nucleic acid residues of the PNA probes in the at least one of the sets of two or more PNA probes that are not derivatized with the charged moieties are derivatized with diethylene glycol, and where the capture tag of the PNA probes in at least one of the sets of two or more PNA probes is biotin.

In some forms of the method, in one or more of the PNA probes there are independently at or between one to three peptide nucleic acid residues that are not derivatized with a charged moiety between every peptide nucleic acid residue that is derivatized with a charged moiety. In some forms of the method, in all of the PNA probes there are independently at or between one to three peptide nucleic acid residues that are not derivatized with a charged moiety between every peptide nucleic acid residue that is derivatized with a charged moiety. In some forms of the method, in one or more of the PNA probes there is an average of at or between 1.0 to 5.0 peptide nucleic acid residues that are not derivatized with a charged moiety between every peptide nucleic acid residue that is derivatized with a charged moiety. In some forms of the method, in all of the PNA probes there is an average of at or between 1.0 to 5.0 peptide nucleic acid residues that are not derivatized with a charged moiety between every peptide nucleic acid residue that is derivatized with a charged moiety.

In some forms of the method, in one or more of the PNA probes there are independently at or between zero to two peptide nucleic acid residues that are not derivatized with a moiety between every peptide nucleic acid residue that is derivatized with a moiety. In some forms of the method, in all of the PNA probes there are independently at or between zero to two peptide nucleic acid residues that are not derivatized with a moiety between every peptide nucleic acid residue that is derivatized with a moiety. In some forms of the method, in one or more of the PNA probes there is an average of at or between 0.5 to 1.5 peptide nucleic acid residues that are not derivatized with a moiety between every peptide nucleic acid residue that is derivatized with a moiety. In some forms of the method, in all of the PNA probes there is an average of at or between 0.5 to 1.5 peptide nucleic acid residues that are not derivatized with a moiety between every peptide nucleic acid residue that is derivatized with a moiety.

In some forms of the method, the reaction mix further includes a single-strand binding protein. In some forms of the method, the first nucleic acid sample has high sequence complexity. In some forms of the method, the first nucleic acid sample includes double stranded DNA. In some forms of the method, the double stranded DNA has never been completely denatured or never been substantially denatured. In some forms of the method, the first nucleic acid sample includes genomic DNA. In some forms of the method, the enriched nucleic acid fragments have an average length of at least 2,000 base pairs. In some forms of the method, the enriched nucleic acid fragments have an average length of at least 10,000 base pairs. In some forms of the method, the enriched nucleic acid fragments have an average length of at least 15,000 base pairs. In some forms of the method, each of the enriched nucleic acid fragments has a length of at least 2,000 base pairs. In some forms of the method, each of the enriched nucleic acid fragments has a length of at least 10,000 base pairs. In some forms of the method, each of the enriched nucleic acid fragments has a length of at least 15,000 base pairs.

In some forms of the method, the nucleic acid fragments targeted by the PNA probes represent at least 90% of the nucleic acid fragments within the enriched nucleic acid sample. In some forms of the method, the enriched nucleic acid sample includes a molar ratio of targeted to non-targeted nucleic acid fragments that is between 50:1 and 150:1. In some forms, the method further includes, following step (b) and prior to step (c), removing unbound PNA probes from the reaction mix. In some forms, the method further includes, simultaneous with capturing the nucleic acid fragments bound by PNA probes, capturing unbound PNA probes via the capture tag.

In some forms of the method, eluting the bound nucleic acid fragments in step (d) is carried out using Herculase II DNA polymerase. In some forms of the method, eluting the bound nucleic acid fragments in step (d) is carried out by deprotonation of the charged moiety by raising the pH.

In some forms, the method further includes amplifying one or more of the nucleic acid fragments in the enriched nucleic acid sample. In some forms of the method, substantially all of the nucleic acid fragments in the enriched nucleic acid sample are amplified. In some forms of the method, the nucleic acid fragments are amplified by whole genome amplification.

In some forms of the method, the nucleic acid sample includes ILLUMINA-MOLECULO® adapter-ligated nucleic acid fragments. In some forms of the method, the nucleic acid sample includes nucleic acid fragments that have been end-repaired and purified according to one or more protocols for PACIFIC BIOSCIENCES® Library Preparation. In some forms of the method, the nucleic acid sample includes PACBIO® hairpin adapter-ligated nucleic acid fragments. In some forms, the method further includes, following step (c) and prior to step (d), ligating PACBIO® hairpin adapters to the captured nucleic acid.

Also disclosed are kits. In some forms, the kit can include a set of PNA robes as described here; and instructions for performing a form of the method as described herein. In some forms, the kit can further include one of more enzymes or proteins for performing one or more steps in the method.

The methods can be carried out without the need for conditions that denature the targeted nucleic acids. Therefore, in some forms, the methods enrich targeted DNA that is non-denatured dsDNA, including DNA that has never been completely denatured or never been substantially or partially denatured. When the targeted DNA includes long fragments of intact double-stranded DNA (dsDNA), the methods enrich dsDNA that preserves the native state of the DNA, including native methylation state and native conformation of the enriched ds DNA.

Methods for sequence enrichment can be carried out as stand-alone procedures, or they can be implemented and adapted to be carried out consecutively or within other procedures, such as procedures for sequencing of DNA libraries and/or preparation of DNA libraries. For example, in some forms, the described methods for sequence enrichment can be implemented within the work flow of existing technologies for library preparation and/or selective sequencing. In some forms, target sequence enrichment methods are incorporated into the workflow of DNA library preparation for sequencing in standard DNA sequencing instruments.

Typically, the methods enable specific enrichment of at least 75% of the target sequence from the nucleic acid sample, such as 80%-100%, preferably 90%-100%, most preferably 97%, 98%, 99% or 100% of the target sequence. Typically the methods provide an enriched sample having a ratio of target to non-target sequences in excess of 1:50, such as 1:75, 1:100 or greater than 1:100.

Each of the method steps is discussed in greater detail, below.

i. Preparation of Nucleic Acid Samples

Any of the methods described herein can include the step of preparing a nucleic acid sample. Methods for preparation of nucleic acid samples are known in the art.

If the nucleic acid sample is within cells, tissue or bodily fluids, preparation and purification of the nucleic acid from the sample can include lysis of cells, such as cells within blood. For example, a lysis reaction mixture can contain up to 100 µl of whole blood and 100 µl of lysis buffer containing 100 mM Tris-HCl (pH 8.5), 50 mM KCl, 6 mM $MgCl_2$, 0.02% Triton X-100 and 1 mg/ml Proteinase K (Boehringer Mannheim; added immediately before use). The lysis reaction mixture can be incubated (e.g., at 55° C. for 15 min., then at 100° C. for 10 min) to simultaneously denature the genomic DNA and inactivate the proteinase K.

To remove cellular debris the reaction mixture can be centrifuged at a suitable speed and time (e.g., 12,000×g for a time between one minute and one hour) to pellet cellular debris. The nucleic acid sample can be removed from the pellet of debris by decanting. In some forms, it is not necessary to centrifuge mixture to remove cellular debris (e.g., when less than 25 µl of blood is used this step can be omitted).

ii. Capture of Specific Fragments of Long Genomic DNA or from a DNA Sequencing Library Methods of capturing and sequencing specific fragments of long genomic DNA using multiple PNA probes are provided. Typically the methods include the steps of shearing target DNA into long fragments; targeting the fragments with hybridization probes; strand invasion of the DNA fragments; removal of non-specifically bound DNA; removal of unbound probes; and isolation, quantitation and characterization of the enriched targeted DNA fragments. Methods to capture and sequence a multiplicity of long double stranded DNA regions from genomic DNA, or equally well from a DNA sequencing library constructed with long DNA fragments have been developed.

a. Shearing Genomic DNA to Generate Long Fragments Followed by Construction of DNA Library Sheared DNA fragments can have an average size of 10,000 base pairs, or 15,000 base pairs, or 20,000 base pairs, or 25,000 base pairs, or 30,000 base pairs, or 35,000 base pairs, or 40,000 base pairs. Where a sequencing library containing long fragments of genomic DNA is desired, such as library can be constructed using standard techniques.

When genomic DNA is used, the genomic DNA can be sheared into fragments of a desired size using any techniques known in the art. For example, genomic DNA can be sheared into fragments having an average size of 10 kb using the Covaris g-TUBE™ centrifugal device (Covaris Prod #: 520079). Preferably, the desired fragment size can be selected (e.g., by adjusting the shearing forces applied to the genomic DNA).

A useful protocol for DNA library construction is described by Wang et al., 2015. Exemplary procedures include DNA end-repair, followed by 3'-end adenylation, and ligation of ILLUMINA® index paired-end adaptors. Exemplary protocols for each of these steps include the following:

| (A) DNA end-repair | |
| --- | --- |
| Component | Volume (µL) |
| A) Combine and mix the following components into the sample tubes: | |
| Size selected DNA | 76.0 |
| End-repair 10× buffer* | 9.0 |
| End-repair enzyme mix* | 5.0 |
| Total | 90.0 |

B) Incubate the mixture at 25° C. for 30 minutes at a bench top thermomixer.
C) Purify with 0.8 × SPRI AMPure XP beads and elute the DNA sample in 52 µl nuclease-free $H_2O$.

*From NEBNext End-Repair Module (Cat. No. E6050L).

| (B) 3'-end adenylation | |
| --- | --- |
| Component | Volume (µL) |
| A) Combine and mix the following components in the sample tubes: | |
| End-repaired DNA | 51.0 |
| NEBNext ™ dA-Tailing Reaction Buffer (10×)* | 6.0 |
| Klenow Fragment (3'-5' exo⁻)* | 3.0 |
| Total | 60.0 |

B) Incubate the mixture at 37° C. thermomixer for 20 min.
C) Purify with 0.8 × SPRI AMPure XP beads and elute the DNA sample in 64 µl nuclease-free $H_2O$.

*From NEBNext dA-Tailing Module (Cat. No. E6053L).

| (C) Ligation of Illumina index paired-end adaptors | |
| --- | --- |
| Component | Volume (µL) |
| A) Combine and mix the following components in the sample tubes: | |
| Illumina Index Paired-end Adaptor (15 µM) | 5.0 |
| Quick Ligase 5 × buffer* | 18.0 |
| A-Tailed DNA | 62.0 |
| Quick Ligase Enzyme* | 5.0 |
| Total | 90.0 |

B) Incubate at room temperature for 30 minutes.
C) Purify with 0.8 × SPRI AMPure XP beads and elute DNA in 72 µl nuclease-free $H_2O$.

*From NEB (Cat. No. E-6056L).

b. Targeting Genomic DNA Fragments

Targeting of genomic DNA fragments or a library can be initiated by contacting the long genomic DNA with a multiplicity of PNA probes, each probe containing a bindable hapten, such as biotin. Typically, the probes can have a length of 18 bases, 19 bases, 20 bases, 21 bases, or 22 bases. Preferred hybridization probes are 20 bases in length.

Each targeted genomic DNA molecule is targeted and invaded by 2 or more different PNA probes. Therefore, contacting the DNA fragments with PNA probes can include adding a mixture of DNA fragments to a mixture containing one or more sets of PNA probes.

Figure 2:
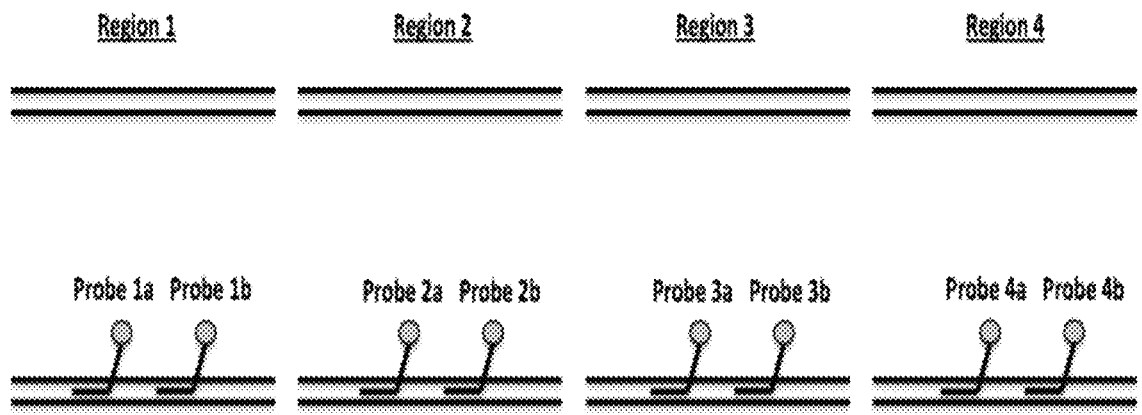
FIG. 2 is a schematic representation of PNA probes targeting four different regions of genomic DNA. Each fragment is targeted by two probes. Each PNA probe is covalently attached to a hapten, preferably biotin.

The number of different hybridization probes designed to target a nucleic acid fragment by the described methods can vary depending upon the size of the nucleic acid fragment being targeted. For example, a fragment of 3,581 base pairs in length required at least two specific PNA hybridization probes for complete (~99%) recovery from a mixture of fragments (as demonstrated in Example 1), and a fragment of 11,970 base pairs in length required at least two or three specific PNA hybridization probes for compete (~99%) recovery from a mixture of fragments (as described in Example 2). Thus, each genomic domain (3,600 base pairs) is typically targeted by two or more different PNA probes that hybridize at two distinct sites according to the schematic in FIG. 2. For example, two or more probes may be used to target fragments up to 20,000 base pairs in length, three or more probes may be used to target fragments up 30,000 base pairs in length, and four or more probes may be used to target fragments up to 40,000 base pairs in length. For example, in a reaction for genomic DNA capture of a total of 2,500 different genomic domains, each of approximately 3,600 base pairs in length, two different biotinylated PNA probes are used for each domain and the total number of different PNA probes in solution is 5,000.

The total concentration of all probes in the reaction can influence the efficacy of affinity purification of the PNA-DNA complex, because unbound PNA probes can compete for binding to an affinity matrix. Each probe can be present at a concentration ranging from 0.2 nM to 2.0 µM. An exemplary concentration for each probe is 0.08 µM. For example, if a double-stranded capture reaction is carried out in a volume of 100 µl, the number of probes is 5,000, and the concentration of each probe is 0.08 µM, the total concentration of all probes is 400 µM.

In some forms the contacting long genomic DNA with a multiplicity of PNA probes occurs in the presence of single-stranded binding protein (SSB).

c. Strand Invasion of Genomic DNA Fragments

Strand invasion of the double-stranded genomic DNA molecules can be achieved by incubating the mixture of genomic DNA and a multiplicity of PNA probes together in suitable conditions for strand invasion to occur. Conditions that can be varied and optimized according to the needs of the experiment include the concentration of the target DNA; concentration of the hybridization probes; composition of the reaction buffer; the reaction volume, the size and shape of the reaction vessel, temperature, and incubation time.

A preferred reaction volume is 100 µl. A preferred amount of target DNA is 100 ng. Preferably, the number of PNA probes used to target each DNA fragment is sufficient to isolate more than 50% of the targeted fragment present in the reaction. When each DNA fragment is targeted by 2 biotinylated probes, the total concentration of unbound probes should be less than 0.5 µM. A preferred amount of target DNA is 100 ng. A preferred concentration of each hybridization probe is 0.08 µM. Preferably, the number of hybridization probes that target each DNA fragment is sufficient to isolate more than 90% of the targeted DNA fragments in the mixture. An exemplary reaction buffer contains 20 mM Tris-HCl (pH 8.0), 30 mM (or 20 mM) NaCl, 0.1 mM EDTA. An exemplary reaction temperature is in the range of 37° C. to 47° C., for a period of time sufficient to achieve strand invasion of the double-stranded genomic DNA molecules. In some forms, the reaction is carried out at 46° C., for a period of four hours. Extended incubation times can be used. For example, incubation times of 16 hours or more, up to and including 36 hours, can be used.

In some forms, single-stranded DNA binding protein (SSB) enables or enhances strand invasion. SSB can be included in the reaction buffer at a final concentration in the range of 0.5 µM to 4 µM, for example, SSB is included at a final concentration of 2 µM.

d. Release of Non-Specifically Bound PNA Probes

The reaction mixture can optionally be incubated for an additional period of time at an increased temperature to facilitate release of non-specifically bound PNA probes. The increased temperature for incubation can be determined based on the $T_m$ of the target DNA and probes. Preferably, the temperature for this step can be in the interval of Tm−10° C. One base pair mismatch between positively charged PNA and DNA target has been shown to decrease the Tm of the interaction approximately 10° C. (Tilani et al., 2014). For example, the reaction can be incubated at 55° C. for an additional 5 minutes.

e. Separation of Unbound PNA Probes

Unbound PNA probes can optionally be separated from the reaction mixture by any suitable means known in the art.

A preferred mode of separation is size-exclusion chromatography. Unbound PNA probes can be separated from DNA and DNA/PNA complexes on the basis of size, by passage through a gel filtration column containing porous beads which have the property of including the free biotinylated PNA probes in their pores, while excluding all long DNA molecules. Long DNA molecules and DNA/PNA complexes are collected in the eluate. An exemplary gel-filtration column is a P100 size exclusion centrifugation column (Bio-Rad). The eluate can optionally be passed through a P100 column one or more additional times. Following size exclusion, the DNA and PNA-DNA fragments are present in the eluate from the column and can be diluted into a suitable volume.

Alternatively, unbound PNA probes can be captured along with PNA probes bound to DNA. Subsequent selective elution of the DNA from the PNA probes to which the DNA was bound can also serve to separate the DNA from the unbound PNA probes.

f. Capturing Specifically Bound PNA Probes

Isolation of specifically bound PNA probes can be achieved by contacting the material excluded from the size-exclusion separation matrix with a surface containing a capture dock specific for the capture tag present on the PNA probes.

In some forms, the capture docks are adhered or coupled to a substrate, such as paramagnetic beads with a biotin-binding entity, preferably streptavidin. For example, biotinylated PNA probes can be captured at the surface of DYNABEADS® M280 streptavidin.

The specifically bound PNA-DNA probes are contacted with the capture docks in a suitable buffer for a suitable time to allow for saturation of the beads with the PNA tagged PNA-DNA complexes. An exemplary incubation is carried out for 2 hours at room temperature.

In some forms, the step of capturing the nucleic acid fragments bound by PNA probes via the capture tag also captures the unbound PNA probes. For such forms the capture medium preferably includes enough capturing components (such as capture docks) to capture all of the PNA probes, both bound and unbound. This is useful when a separate step of separating the unbound PNA probes is not performed.

g. Removal of Non-Bound PNA Probes and Non-Bound DNA

Probes bound to capture docks that are adhered or coupled to a substrate can be isolated from the solution and washed once or more than once to remove the non-bound DNA and non-specifically (weakly) associated probe-DNA complexes.

For example, when magnetic beads are used as a substrate, the beads and bound DNA can be separated from the mixture using a magnet. The isolated beads and bound DNA can be washed once, twice, or more than twice.

Any suitable washing buffer can be used to remove non-bound PNA probes and the DNA without any bound PNA probes from the surface. Washing of the DNA-PNA-substrate complexes is facilitated by use of a column. For example, if the substrate includes beads, the beads can be placed into a column and wash buffer passed through the column continuously to flush away the reaction mixture. The only remaining material bound to the substrate is genomic DNA or DNA library fragments that contain preferably two or more bound PNA probes.

h. Eluting the Targeted Long DNA Fragments

Targeted long DNA fragments free of bound PNA are released from the capture surface (e.g., magnetic beads) using a suitable denaturing buffer. Suitable buffers include 20 mM Tris pH 8.0, 400 mM (or 200 mM) NaCl, 0.1 mM EDTA, 20% formamide, and 0.01% Trion X-100 at 65° C. for 5 minutes, with agitation. In some forms, the step of eluting the bound DNA includes addition of one or more agents or solutions to enhance elution from the PNA probes and thereby increase the yield of the enriched DNA.

Exemplary methods for enhancing elution include methods that displace the PNA from the bound target DNA. In some forms, the PNA probes are displaced by primer extension of the 3' hairpin using enzymes and dNTPs. An exemplary enzyme for use in displacement of PNA probes by primer extension of the 3' hairpin is Herculase DNA polymerase II. Herculase II DNA polymerase is a fusion protein of Pfu Ultra and a DNA-binding domain that is designed to facilitate DNA polymerization on GC-rich templates. Herculase II DNA polymerase is available from multiple commercial sources, including from Agilent Technologies (Catalog #600675). Enzymes such as Herculase II DNA polymerase successfully displace the PNA and create a DNA-DNA duplex containing a digestion site for the restriction enzyme BccI, whereas the starting DNA-PNA duplex cannot be digested by BccI. Therefore, in some forms, when the step of PNA probe elution includes use of Herculase II DNA polymerase, the completeness of PNA probe displacement can be determined by correlation with the efficiency of the restriction digestion of Herculase II products (Budno, et al, 2010).

Methods of increasing the yield of enriched DNA can also include deprotonation-facilitated release of PNA from bound target DNA when using a PNA probe having a charged amino acid composition, at slightly alkaline pH. For example, when using one or more PNA probes including residues modified by derivatization with a thialysine moiety, the slightly alkaline pH can be used to assist dissociation of probe/captured nucleic acids.

The eluted DNA, free of the bound PNA probes, consists of the originally targeted double-stranded DNA fragments, each fragment including the two or more targeted nucleotide sequences. Enriched DNA (as well as any unbound DNA remaining in the supernatant) can be characterized and quantified using methods known in the art.

In some forms, the enriched DNA is present in extremely small amounts. For example, the enriched DNA may be undetectable even after staining with fluorescent intercalating dyes. In such forms, the enriched DNA is preferably analyzed by methods involving DNA amplification. In some forms, semi-quantitative PCR can be carried out to amplify the captured DNA fragments and optionally to amplify any unbound DNA remaining in the reaction mixture to determine the % capture.

iii. Sequence Determination and Analysis of Long Genomic DNA

The described methods for sequence-specific DNA capture provide enriched double-stranded DNA fragments without the need for PCR amplification. Therefore, the methods provide large dsDNA fragments in the same proportions and having the same methylation status as was present in the organism from which they were derived. Captured genome fragments can be quantified and sequenced to provide information regarding variant type, copy number variation, frequency spectra, population distributions and population diversity.

For example, following methods for the capture of specific fragments of long genomic DNA or from a DNA sequencing library according to steps ii.a.-ii.h. (above), the released DNA can be packaged into a sequencing library containing all of the captured long DNA fragments.

The complete DNA sequence of the captured long dsDNA can be determined using any suitable DNA sequencing techniques and instrumentation known in the art. For example, DNA sequencing can be carried out by the Agencourt Bioscience Corporation (Beverly, Mass.). DNA sequencing data can be analyzed using the multiple sequence alignment program Clustal W (e.g., see web site ebi.ac.uk/Tools/clustalw/).

If a library has been constructed prior to sequence-specific DNA capture, the complete DNA sequence of captured long DNA library fragments can be determined directly by using a DNA sequencing instrument compatible with the library.

Those skilled in the art will be able to decide when it is preferable to construct a DNA library prior to sequence-specific DNA capture, as opposed to performing sequence-specific DNA capture prior to the construction of a library. In general, when the objective is to capture a relatively small number of DNA fragments, it is preferable to construct a library prior to sequence-specific DNA capture. On the other hand, when the number of genomic DNA fragments targeted for capture is large (more than 1000 different DNA fragments being targeted for enrichment) it may be preferable to construct the DNA sequencing library after sequence-specific DNA capture has been performed.

In some forms, the objective of performing target enrichment using the disclosed methods for capture of long DNA fragments is not to obtain DNA methylation information, but only to obtain DNA sequence information without base modification information. For these DNA sequencing forms, the captured DNA fragments can be amplified after release from the capture surface, and prior to DNA sequencing library construction. A preferred amplification method for these DNA sequencing forms is whole genome amplification (Hasmats et al., 2014). Whole genome amplification can be performed using any suitable technique. For example, the GE Healthcare Illustra GenomiPhi V2 DNA Amplification kit (GE Healthcare, Waukesha, Wis.) can be used. Alternatively, amplification can be performed using the QIAGEN REPLI-g Mini Kit, Catalog No. 150023 (QIAGEN, 27220 Turnberry Lane, Valencia, Calif. 91355). DNA amplified using the REPLI-g Mini Kit has been tested with, and is highly suited for, numerous downstream analyses, including next-generation sequencing. Since there is no requirement for a separate PCR-based amplification step, REPLI-g whole genome amplification and a subsequent library preparation step will require less hands-on time and result in longer read-lengths than PCR-based methods. High-quality, comparable next-generation sequencing (NGS) results showing a high percentage of sequence coverage and very low error rates can be achieved with either the GE Healthcare Illustra GenomiPhi or the QIAGEN Repli-g amplification methods.

a. Haplotype Analysis

Methods for haplotype analysis of long genomic dsDNA fragments are provided. For example, the described methods for sequence-specific DNA capture can optionally include the additional step of determining the phase of one or more SNPs on a single chromosome.

Single nucleotide polymorphisms (SNPs) are markers that have emerged for whole-genome linkage scans and association studies. SNPs are a common type of sequence variation and are useful markers due to their stability, abundance, and relative ease of scoring. It is estimated that there are over 10 million SNPs, with a minor allele frequency of approximately 5% or more. An international consortium to identify and characterize human haplotypes (HapMap Project) across four geographically distinct human populations identified a standard set of common-allele SNPs.

Therefore, common allele SNPs can be used for the identification and characterization of underlying genetic bases for complex human diseases, pathogen susceptibility, and differential drug responses.

Genotyping of the large genomic DNA fragments enriched by the described methods can be carried out using any system known in the art. The preferred method for genotyping capture DNA fragments is DNA sequencing capable of generating long reads. Other capture technologies can be used, such as the Affymetrix® Genome-Wide Human SNP Nsp/Sty 6.0 and Illumina 1.0 Million SNP mass arrays, but these are not preferred.

iv. Capture and DNA Methylation Sequencing of Specific Fragments of Long DNA from a Genomic Library Using Multiple PNA Probes Disclosed are methods including determining the methylation state of one or more long dsDNA sequences in a sample. Methods to capture and achieve DNA methylation sequencing of a multiplicity of long double stranded DNA regions from a DNA sequencing library constructed with long DNA fragments are provided. Capture of targeted sequence-specific fragments of DNA from any suitable DNA sample using multiple PNA probes can be achieved using method steps ii.a-ii.h., described above. Genomic target enrichment can be utilized to generate DNA sequences containing long reads of DNA methylation information, such long reads being enabling for the phasing of DNA methylation across large sequence domains, potentially in the range of 40,000 to 1,000,000 base pairs.

Determining the methylation status of a DNA fragment can be carried out by any means known in the art, for example, by bisulfite sequencing. Sequencing of genomic DNA subjected to sodium bisulfite conversion (MethylC-Seq) can enable single-base resolution, strand specific identification of methylated cytosines throughout the majority of the genome. Therefore, the described methods can be used to generate high-coverage whole-genome mammalian DNA methylomes. Read coverage and bisulfite conversion rates on distinct alleles can be used to quantify allele-specific DNA methylation (ASM) by any methods known in the art, for example, using Fisher's exact test.

Determining the complete DNA methylation sequence of the captured long DNA library fragments can be achieved using an automated DNA sequencing instrument capable of reporting DNA sequences, as well as DNA modification information. An exemplary instrument is the PACIFIC BIOSCIENCES® RSII instrument, used with Tet1 oxidation chemistry (Clark, et al., 2013).

v. Iterative Methods for Culling PNA Probes Suspected of not Being Optimally Specific for Enrichment of Genomic DNA Domains by Means of Double-Stranded DNA Capture Methods for the identification and removal of PNA probes suspected of being sub-optimally-specific have also been developed. The methods can include specific capture of double-stranded DNA.

In some forms, a set of PNA probes is designed for capture of different regions throughout a genome. For example, a set of 5,000 PNA probes can be designed for capture of 2,500 different regions in the human genome. Each region is 20,000 base pairs in length, and is targeted by 2 specific PNA probes, directed to hybridize with specific target sequences within a 3,000 base interval located in the center of each 20,000 base region. The targeted DNA domains, in total, can correspond to up to 50 million base pairs (50 Mb of DNA). The set of 5,000 probes, each probe synthesized with a biotin residue at one terminus of the molecule, is used for performing capture and sequencing of fragments of long DNA from a genomic library, using method steps ii.a.-ii.h., described above.

For example, sequencing can be performed using a preferred platform capable of generating long reads, such as the PACIFIC BIOSCIENCES® RSII system, and the theoretical sequence oversampling is calculated to be 100×, based on a 50 Megabase genome.

The Iterative methods for culling PNA probes suspected of not being optimally specific for enrichment of genomic DNA domains are subsequently carried out as follows:

a. Mapping of Sequenced DNA

The sequencing reads are mapped to the human genome, and scaffolds are constructed using appropriate software. More than 86% of the post-filter reads are aligned to the human reference genome. Approximately 80% of the aligned sub-read scaffolds map to the 50 Mb aggregate of genomic regions originally targeted for capture, while approximately 20% of the reads map to other, non-targeted regions of the genome. Among the 20% of the reads that do not map to targeted DNA, the bioinformatics analysis identifies 350 genomic regions, each approximately 20,000 base pairs long, where the sub-read scaffolds show an average oversampling of 25 per region. This result implies that among the 5,000 PNA probes, there is a subset of underperforming probes that effectively capture 350 non-targeted genomic domains.

b. Identification of Non-Specific Hybridization Interactions

Using a suitable sequence alignment and search tool, such as "ublast" (part of the USEARCH sequence analysis package, Edgar, 2010) the complete set of 5,000 PNA probe sequences is sequentially aligned (5,000 independent alignment runs) to the sequences of the 350 genomic regions that were captured due to nonspecific hybridization interactions. Following alignment, 350 PNA probes are identified that yield the most significant alignment scores with specific 20-base sequences located within the 350 genomic regions that were captured due to non-specific hybridization interactions with two or more mismatches.

c. Substitution of Non-Specific PNA Probes

350 PNA probes identified by significant alignment scores with 20-base sequences located within the 350 non-specifically captured genomic regions are substituted by 350 new PNA probes, to create a new set of 4,650 existing+350 new PNA probes, equal to 5,000 PNA probes, targeting the same original 2,500 regions of the genome.

d. Determination of Enhanced DNA Capture

Capture and sequencing of fragments of long DNA from a genomic library, using method steps ii.a.-ii.h., as described above is repeated. Sequencing is repeated and analysis is carried out as in method step i. with the new data set. The objective of repeating the experiment with 350 new probes is to ascertain which of the 350 genomic regions that were previously captured due to non-specific hybridization interactions can be identified as having been eliminated in the second iteration of the capture experiment, in which the 350 probes suspected to be nonspecific were substituted for new probes. Optionally, additional iterations of the culling procedure can be carried out as necessary.

In some forms, the disclosed methods have one or more of the following features: (a) the target nucleic acid is not denatured prior to, or during, binding and capture; (b) a multiplicity of long dsDNA fragments are targeted, each by a minimum of two PNA probes; (c) the PNA probes used have a chiral backbone favoring a right-handed helical conformation (such probes are more capable of strand invasion); (d) the PNA probes include chiral monomers modified with short-chain oligoethylene moieties and chiral monomers with positively charged amino acids, preferably lysine; and (e) many thousands or probes can be used in a single capture reaction to capture many thousands of different target nucleic acids.

In some forms, the disclosed methods use two alternative types of chiral PNA, each designed to induce a right-handed helical conformation in the PNA probe. Most preferred is chiral PNA that include a mixture of gamma-L-Lysine monomers and gamma-short-chain oligoethylene PNA monomers (the latter synthesized starting from gamma-L-Serine). Also preferred are chiral PNA probes that include a mixture of alpha-D-Lysine and alpha-short-chain oligoethylene PNA monomers (the latter synthesized starting from alpha-D-serine).

In some forms, the disclosed methods do not use triplex formation and thus avoids having to target only homopurine-homopyrimidine sequences in DNA. Such sequences are often not unique in the human genome. In some forms, the disclosed methods do not use overlapping nor partially-overlapping probes.

In some forms, the disclosed methods do not use pseudo-complementary PNA bases in the PNA probes due to their cost. However, the disclosed methods can use pseudo-complementary PNA bases, preferably in a small subset of PNA probes, for the purpose of reducing the possibility of interactions between particular PNA probes (among thousands of different PNA probes used in combination) that happen to be partially complementary by chance. In other words, pseudocomplementary PNA bases can be used in the PNA probes as an alternative to eliminating all instances of complementary sequences between the PNA probes used in a set of PNA probes.

2. Exemplary Protocols

Exemplary protocols for the capture of specific fragments of long genomic DNA or from a DNA sequencing library according to the described methods are provided. Methods for the capture of specific fragments of long genomic DNA can be carried out as a stand-alone procedure, or they can be integrated into other protocols for the identification and/or manipulation of nucleic acids. Relevant Downstream applications include Integration with PACIFIC BIOSCIENCES® sequencing library preparation, Integration with ILLUMINA® sequencing library preparation, integration with Oxford Nanopore library preparation for nanopore sequencing, integration within protocols for kits for isolation of mitochondrial DNA from total DNA (e.g., DNA obtained from human tissues), integration within protocols for kits for sequence enrichment of specific regions of the genome from DNA obtained from specific subsets of human white blood cells, such as CD4+ T-cells, CD8+ T-cells, or any other subset of white cells, integration within protocols for kits for enrichment of specific microbial genomes from DNA samples obtained from human feces, integration within protocols for kits for enrichment of specific DNA sequences from non-human species (e.g., cats, dogs, horses, cows, chickens, etc.), and integration within protocols for kits for Kits for enrichment of specific DNA sequences from important plant species.

Typically, the precise conditions and reagents used to perform each of the method steps can be modified or optimized for specific enrichment of a given target sequence or group of target sequences.

i. Exemplary Targeted DNA Enrichment Protocol Using PetaOmics Enrichment Technology In some forms, the methods are optimized for enrichment of a desired fragment of double-stranded DNA from a mixture containing multiple restriction fragments of phage lambda DNA. An exemplary phage lambda DNA target fragment size is 8.5 Kb. In some forms the methods are optimized for sequence enrichment of specific fragments of double-stranded genomic DNA from total human genomic DNA. An exemplary genomic DNA target fragment size is 8 Kb.

a. PetaOmics Target Enrichment of DNA Library Material

1. Prepare probes by heating at 65° C. for 10 minutes, then vortex and spin down.
2. Combine 1 μg target DNA (sheared to fragments of a desired size), 20 pmoles each probe, 5× SI buffer, 2.60 μL SSB, 7.2 μL Formamide, and add $H_2O$ to a total volume of 50 μL. Exemplary final concentrations are 400 nM each probe, 41.7 mM total NaCl, 2 μM SSB, 14% formamide.
3. Probe concentration 200 nM each; make 2 samples and do not add probe to one tube ("control")–1 no probe samples+1 samples containing all probes.
4. Briefly vortex each tube and spin down to get all liquid at the bottom.

5. Place tubes in dry bath and incubate at 50° C. for 4 hours for strand invasion (SI), then incubate at 60° C. for 5 minutes.
6. Purify the DNA from the free probe (e.g., using a P100 size exclusion column). Spin at 100×g for 4 minutes.
7. Combine purified SI reaction with BSA passivated C1 magnetic beads+100 μL H₂O.
8. Incubate capture reactions at room temperature on rotator for 2 hours.
9. Take samples of rotator and put on magnet for 3 minutes. Transfer supernatant to new tube.
10. Add 150 μL 0.02% Tween-20 Wash buffer (e.g., containing TWEEN®) to beads, re-suspend by pipetting, vortex for 30 sec, put on magnet for 2 mins. Discard wash buffer.
11. Repeat wash three times and discard washes.
12. Add 150 μL 0.02% Tween-20 Wash buffer, re-suspend and incubate in thermomixer at 50° C.×7 min.
13. Add 100 μL elution buffer (e.g., 10 mM Tris pH 8, 400 mM NaCl, 0.1 mM EDTA, 20% formamide) to washed beads, vortex, spin and incubate at 75° C. for 7 minutes with agitation in thermomixer.
14. Place tubes on magnet for 3 minutes. Transfer eluate to new tube.
15. Purify supernatants and eluted DNA (e.g., using AMPure XP beads), wash 2× with ethanol, elute in 40 μL dH₂O. Purify supernatants and eluted DNA (e.g., with AMPure XP beads), wash 2× with ethanol, elute into suitable volume (e.g., 40 μL) dH₂O.
16. Prepare qPCR using Control sup, Control eluate, PNA sup and PNA eluates as templates.

ii. Incorporation of PetaOmics Enrichment Technology into PACIFIC BIOSCIENCES® Library Preparation Workflow for DNA Library Preparation, Including Ligation of Hairpin Adapters The following protocols (steps a-c) illustrate how the described methods for target sequence enrichment can be incorporated into the workflow of DNA library preparation for sequencing in standard DNA sequencing instruments. While it is of course possible to perform the target enrichment steps prior to DNA sequencing library preparation, in some instances it is actually advantageous to merge the target enrichment methods of this invention into the DNA library preparation work flow. In an exemplary protocol, PNA probes containing PNA residues modified with gamma-L-thialysine are used in a sequence enrichment step embedded in a sequencing library preparation for a PACIFIC BIOSCIENCES® sequencing instrument. In some forms, PNA residues modified with L-lysine are used in the PNA probes for the Example based on ILLUMINAO sequencing.

a. Ligation of PACBIO® Hairpin Adapters

1. Shear 3-5 μg of target DNA (e.g., human genomic DNA) to average fragment length of 20 kb (e.g., using Covaris g-tubes) and centrifuge (e.g., 4,000 rpm for 60 seconds).
2. Concentrate sheared DNA sample (e.g., via 0.45× AMPure PB magnetic beads);
   a. Add volume of AMPure PB beads to 0.45× volume of DNA sample;
   b. Mix to heterogeneity. Shake on vortex mixer at 2,000 rpm for 10 minutes;
   c. Place tubes on magnet until beads collect on side of tube and solution is clear. Aspirate cleared supernatant with pipette carefully to not disturb bead pellet;
   d. Wash AMPure PB beads twice with 70% ethanol;
   e. Remove residual ethanol and air-dry beads for 30-60 seconds;
   f. Resuspend beads in 38 μL PacBio Elution buffer, vortex at 2,000 rpm for 1 minute. Place tubes on magnet until beads collect and solution is clear; and
   g. Transfer supernatant to new 0.5 mL Eppendorf tube.
3. Treat sheared genomic DNA with Exonuclease VII to remove single-stranded ends from DNA fragments.
   a. Add DNA Damage Repair Buffer, NAD+, ATP high, dNTPs and ExoVII enzyme from PACBIO® Template Preparation Kit to 1×; and
   b. Incubate at 37° C. for 15 minutes. Return reaction to 4° C.
4. Repair DNA Damage by adding 2 μL of DNA Damage Repair Enzyme Mix and incubating at 37° C. for 20 minutes. Return reaction to 4° C. for 1-5 minutes.
5. Repair ends of DNA sample by adding 2.5 μL of End Repair Enzyme Mix and incubating at 25° C. for 5 minutes. Return reaction to 4° C.
6. Purify DNA sample via 0.45× AMPure PB magnetic beads as in step #2. Elute in 20 μL PacBio Elution Buffer.
7. Ligate PACBIO® hairpin adapters via blunt-end ligation.
   a. Add Annealed Blunt Hairpin Adapters to end-repaired DNA sample and mix well;
   b. Add Template Prep Buffer and ATP low and mix well;
   c. Add Ligase enzyme and dH₂O and mix well by pipetting; and
   d. Incubate ligation reaction at 25° C. overnight.
8. Inactivate ligase by incubating reaction at 65° C. for 10 minutes. Return reaction to 40° C.
9. Treat ligated DNA with Exonuclease III and Exonuclease VII to remove failed ligation products. Incubate reaction at 37° C. for 1 hour then return reaction to 4° C.
10. Purify ligated DNA sample (e.g., via 0.45× AMPure PB magnetic beads) as in step #2. Elute in suitable volume (e.g., 30 μL) dH₂O.

b. PetaOmics Target Enrichment of DNA Library Material

11. PNA-mediated strand invasion for capture of selected double-stranded DNA targets.
    a. Add 5× Strand Invasion buffer (e.g., 10 mM Tris pH 8.0, 30 mM NaCl, 0.1 mM EDTA, 0.02% TWEEN-20®) to 1×;
    b. Add Taq Single-stranded DNA Binding Protein (SSB) to final concentration of 2 μM;
    c. Add a set of target-directed gamma-PNAs (e.g., 18-mer PNAs with 4 gamma-L-thialysine and 4 gamma-mini-PEG modifications) to final concentration of 400 nM per PNA;
    d. Add formamide to final concentration of 14.4%;
    e. Mix well and incubate reaction at 50° C. for 3 hours; and
    f. Incubate reaction at 60° C. for 5 minutes for stringency step to melt imperfect PNA interactions with the DNA.
12. Remove unbound, free gamma-PNA (e.g., via P100 size-exclusion column).
    a. Add strand invasion reaction to column and spin at 100×g for 4 minutes at room temperature.
13. Capture biotinylated PNA-bound target DNA (e.g., with BSA-passivated C1 streptavidin magnetic beads).
    a. Resuspend washed and BSA-passivated C1 streptavidin magnetic beads in 50 μL strand invasion reaction, 100 μL dH₂O and 50 μL Wash buffer (e.g., 10 mM Tris pH 8.0, 0.25M NaCl, 0.1 mM EDTA, 0.05% Tween-20) to a final volume of 200 μL in a 1.5 mL Eppendorf tube; and
b. Incubate capture reaction on rotating platform for 2 hours at room temperature.
14. Wash streptavidin beads three times in Wash buffer at room temperature. Place on magnet each time until solution is clear. Discard supernatant.
15. Wash streptavidin beads once in Wash buffer by incubating at 50° C. for 7 minutes in thermomixer (agitation=800 rpm). Place on magnet until solution is clear. Discard supernatant.
16. Elute captured target DNA from streptavidin beads by resuspending the beads in Elution buffer (e.g., 10 mM CAPSO pH 9.75, 400 mM NaCl, 0.1 mM EDTA, 20% formamide) to raise the pH above the pKa of the gamma-thialysine groups (pKa=9.5) thus decreasing the PNA melting temperature. Incubate at 75° C. for 7 minutes in thermomixer (agitation=800 rpm). Addition of supercoiled, circular DNA can be added as carrier if capturing very small amounts of DNA.

c. PACIFIC BIOSCIENCES® Library Preparation, Steps after Hairpin Adapter Ligation 17. Purify enriched target DNA (e.g., via 0.45× AMPure PB magnetic beads as in step #2). Elute in 30 μL PACBIO® Elution Buffer.
18. Use Blue Pippin instrument to size-select enriched target DNA.
   a. BP start: 8000; BP end: 50000.
19. Purify and concentrate size-selected target DNA (e.g., via 1× AMPure PB magnetic beads as in step #2). Elute in 10 μL PACBIO® Elution Buffer.
20. Sequence target-enriched DNA using PACIFIC BIOSCIENCES® RSII instrument.

ii. Incorporation of PetaOmics Enrichment Technology into PACIFIC BIOSCIENCES® Library Preparation Workflow for DNA Sequencing, Including On-Bead Hairpin Adapter Ligation The following protocols (steps a-d) illustrate how the described methods for target sequence enrichment can be incorporated into the workflow of DNA sequencing including On-bead Hairpin Adapter Ligation. While it is of course possible to perform the target enrichment steps prior to DNA sequencing, it is actually advantageous to merge the target enrichment methods of this invention into the DNA sequencing work flow.

a. PACIFIC BIOSCIENCES® Library Preparation, Steps 1 to 6, Prior to Adapter Ligation 1. Shear 3-5 μg of target DNA (e.g., human genomic DNA) to average fragment length of 20 kb (e.g., using Covaris g-tubes). Centrifuge at 4000 rpm for 60 seconds.
2. Concentrate sheared DNA sample (e.g., via 0.45× AMPure PB magnetic beads);
   a. Add volume of AMPure PB beads to 0.45× volume of DNA sample
   b. Mix to heterogeneity. Shake on vortex mixer at 2000 rpm for 10 minutes;
   c. Place tubes on magnet until beads collect on side of tube and solution is clear. Aspirate cleared supernatant with pipette carefully to not disturb bead pellet;
   d. Wash AMPure PB beads twice with 70% ethanol;
   e. Remove residual ethanol and air-dry beads for 30-60 seconds;
   f. Resuspend beads in 38 μL PACBIO® Elution buffer. Vortex at 2000 rpm for 1 minute. Place tubes on magnet until beads collect and solution is clear;
   g. Carefully pipet supernatant and transfer to new 0.5 mL Eppendorf tube.
3. Treat sheared genomic DNA with Exonuclease VII to remove single-stranded ends from DNA fragments.
   a. Add DNA Damage Repair Buffer, NAD+, ATP high, dNTPs and ExoVII enzyme from PACBIO® Template Preparation Kit to 1×;
   b. Incubate at 37° C. for 15 minutes. Return reaction to 4° C.
4. Repair DNA Damage by adding 2 μL of DNA Damage Repair Enzyme Mix and incubating at 37° C. for 20 minutes. Return reaction to 4° C. for 1-5 minutes.
5. Repair ends of DNA sample by adding 2.5 μL of End Repair Enzyme Mix and incubating at 25° C. for 5 minutes. Return reaction to 4° C.
6. Purify DNA sample (e.g., via 0.45× AMPure PB magnetic beads) as in step #2. Elute in 30 μL PACBIO® Elution Buffer.

b. PetaOmics Target Enrichment of DNA Library Material

7. PNA-mediated strand invasion for capture of selected double-stranded DNA targets.
   a. Add 5× Strand Invasion buffer (e.g., 10 mM Tris pH 8.0, 30 mM NaCl, 0.1 mM EDTA, 0.02% TWEEN-20®) to 1×;
   b. Add Taq Single-stranded DNA Binding Protein (SSB) to final concentration of 2 μM;
   c. Add a set of target-directed gamma-PNAs (e.g., 18-mer PNAs with 4 gamma-L-thialysine and 4 gamma-mini-PEG modifications) to final concentration of 400 nM per PNA;
   d. Add formamide to final concentration of 14.4%;
   e. Mix well and incubate reaction at 50° C. for 3 hours;
   f. Incubate reaction at 60° C. for 5 minutes for stringency step to melt imperfect PNA interactions with the DNA.
8. Remove unbound, free gamma-PNA (e.g., via P100 size-exclusion column).
   a. Add strand invasion reaction to column and spin at 100×g for 4 minutes at room temperature.
9. Capture biotinylated PNA-bound target DNA with BSA-passivated C1 streptavidin magnetic beads.
   a. Resuspend washed and BSA-passivated C1 streptavidin magnetic beads in 50 μL strand invasion reaction, 100 μL dH$_2$O and 50 μL Wash buffer (e.g., 10 mM Tris pH 8.0, 0.25M NaCl, 0.1 mM EDTA, 0.05% TWEEN-20®) to a final volume of 200 μL in a 1.5 mL Eppendorf tube; and
   b. Incubate capture reaction on rotating platform for 2 hours at room temperature.
21. Wash streptavidin beads three times in Wash buffer at room temp. Place on magnet until solution is clear. Discard supernatant.
22. Wash streptavidin beads once in Wash buffer by incubating at 50° C. for 7 minutes in thermomixer (agitation=800 rpm). Place on magnet until solution is clear. Discard supernatant.

c. On-Bead PacBio Hairpin Adapter Ligation

23. Ligate PACBIO® hairpin adapters via blunt-end ligation on streptavidin beads that contain captured DNA molecules.

a. Resuspend washed streptavidin beads by adding Annealed Blunt Hairpin Adapters, Template Prep buffer, ATP low, dH$_2$O and ligase enzyme. Mix well by pipetting; and
b. Incubate on-bead ligation reaction at 25° C. overnight on rotating platform.

24. Inactivate ligase by incubating reaction at 65° C. for 10 minutes. Return reaction to 4° C.
25. Elute captured, adapter-ligated target DNA from streptavidin beads by resuspending the beads in Elution buffer (e.g., 10 mM CAPSO pH 9.75, 400 mM NaCl, 0.1 mM EDTA, 20% formamide) to raise the pH above the pKa of the gamma-thialysine groups (pKa=9.5) thus decreasing the PNA melting temperature. Incubate at 75° C. for 7 minutes in thermomixer (agitation=800 rpm). Addition of supercoiled, circular DNA can be added as carrier if capturing very small amounts of DNA.

d. PACIFIC BIOSCIENCES® Library Preparation and Sequencing

26. Treat eluted DNA sample with Exonuclease III and Exonuclease VII to remove failed ligation products. Incubate reaction at 37° C. for 1 hour then return reaction to 4° C.
27. Purify ligated DNA sample (e.g., via 0.45× AMPure PB magnetic beads as in step #2). Elute in 30 μL dH$_2$O.
28. Use Blue Pippin instrument to size-select enriched target DNA.
    a. BP start: 8000; BP end: 50000
29. Purify and concentrate size-selected target DNA (e.g., via 1× AMPure PB magnetic beads) as in step #2. Elute in 10 μL PACBIO® Elution Buffer.
30. Sequence target-enriched DNA using PACIFIC BIOSCIENCES® RSII instrument.

iii. Incorporation of PetaOmics Enrichment Technology into ILLUMINA® Library Preparation Workflow for DNA Sequencing, Including Herculase II-Mediated PNA-Displacement and Amplification The following protocols (steps a-d) illustrate how the described methods for target sequence enrichment can be incorporated into the workflow of DNA sequencing including Herculase II-mediated PNA-displacement and amplification. While it is of course possible to perform the target enrichment steps prior to DNA sequencing, it is actually advantageous to merge the target enrichment methods of this invention into the DNA sequencing work flow.

a. ILLUMINA® Library Preparation

1. Shear 3-5 μg of target DNA (e.g., human genomic DNA) to average fragment length of 20 kb (e.g., using Covaris g-tubes). Centrifuge at 4000 rpm for 60 seconds.
2. Concentrate sheared DNA sample (e.g., via 0.8× AMPure XP magnetic beads):
    a. Add volume of AMPure XP beads to 0.45× volume of DNA sample;
    b. Mix to heterogeneity. Shake on vortex mixer at 2,000 rpm for 10 minutes;
    c. Place tubes on magnet until beads collect on side of tube and solution is clear. Aspirate cleared supernatant with pipette carefully to not disturb bead pellet;
    d. Wash AMPure XP beads twice with 70% ethanol;
    e. Remove residual ethanol and air-dry beads for 30-60 seconds;
    f. Resuspend beads in 34 μL TE buffer. Vortex at 2,000 rpm for 1 minute; Place tubes on magnet until beads collect and solution is clear; and
    g. Carefully pipet supernatant and transfer to new 0.5 mL Eppendorf tube.
3. Repair sheared DNA ends
    a. Add 10× End Repair Buffer, dNTPs, ATP and End Repair Enzyme Mix and mix well;
    b. Incubate reaction at room temperature for 45 minutes; and
    c. Incubate at 70° C. for 10 minutes to inactivate enzymes.
4. Purify end-repaired DNA (e.g., via 0.8× AMPure XP magnetic beads as in step #2). Elute in 42 μL TE buffer.
5. Ligate A-tails on to DNA ends
    a. Add NEB Next dA-Tailing buffer and Klenow fragment to final volume of 50 μL. Mix well and incubate at 37° C. for 30 minutes.
6. Purify A-tailed DNA fragments via 0.8× AMPure XP magnetic beads as in step #2. Elute in 8 μL TE buffer.
7. Ligate ILLUMINA-MOLECULO® adapters on to DNA ends via T4 ligase.
    a. Add 2× Rapid Ligation buffer, 50 μM annealed Moleculo Adapters and T4 ligase to final volume of 20 μL. Mix well and incubate at room temperature for 10 minutes.
8. Purify ILLUMINA-MOLECULO® adapter-ligated DNA fragments via 0.8× AMPure XP magnetic beads as in step #2.
9. Elute in 30 μL TE buffer.

b. PetaOmics Target Enrichment of Illumina DNA Library Material

10. Gamma-PNA-mediated strand invasion of Target DNA
    a. Add 5× Strand Invasion buffer (e.g., 10 mM Tris pH 8.0, 30 mM NaCl, 0.1 mM EDTA, 0.02% Tween-20) to 1×;
    b. Add Taq Single-stranded DNA Binding Protein (SSB) to final concentration of 2 μM;
    c. Add a set of target-directed gamma-PNAs (e.g., 18-mer PNAs with 4 gamma-L-lysine and 4 gamma-mini-PEG modifications) to final concentration of 400 nM per PNA;
    d. Add formamide to final concentration of 14.4%;
    e. Mix well and incubate reaction at 50° C. for 3 hours; and
    f. Incubate reaction at 60° C. for 5 minutes for stringency step to melt imperfect PNA interactions with the DNA.
11. Remove unbound, free gamma-PNA (e.g., via P100 size-exclusion column).
    a. Add strand invasion reaction to column and spin at 100×g for 4 minutes at room temperature.
12. Capture biotinylated PNA-bound target DNA with BSA-passivated C1 streptavidin magnetic beads.
    a. Resuspend washed and BSA-passivated C1 magnetic beads in 50 μL strand invasion reaction, 100 μL dH$_2$O and 50 μL Wash buffer (e.g., 10 mM Tris pH 8.0, 0.5M NaCl, 0.1 mM EDTA, 0.05% TWEEN-20®) to a final volume of 200 μL in a 1.5 mL Eppendorf tube; and
    b. Incubate capture reaction on rotating platform for 2 hours at room temperature.
31. Wash streptavidin beads three times in Wash buffer at room temperature. Place on magnet each time until solution is clear. Discard supernatant.

32. Wash streptavidin beads once in Wash buffer by incubating at 45° C. for 7 minutes in thermomixer (agitation=800 rpm). Place on magnet until solution is clear. Discard supernatant.

c. On-Bead Herculase II-Mediated PNA Displacement and Amplification of Target DNA 33. Simultaneously elute target DNA from streptavidin beads and amplify it via Herculase II Fusion DNA Polymerase (Agilent). The Herculase enzyme has been shown to displace bound PNA from DNA (Brudno, et al. *Nature Chemical Biology;* 6 (2): pp. 148-155 (2010))
   a. Resuspend washed streptavidin beads by adding 5× Herculase II reaction buffer, dNTPs, Illumina-Moleculo adapter-specific Primer, Herculase II Fusion DNA polymerase and dH$_2$O to 50 µL final volume. Mix well by pipetting; and
   b. Put reaction in thermocycler with cycling conditions according to Agilent protocol.
34. Purify amplified target DNA fragments (e.g., via 0.8× AMPure XP magnetic beads as in step #2). Elute in 20 µL TE buffer. Determine DNA concentration via Qubit instrument (Life Technologies, Inc.).

d. NEBNext Library Preparation for Illumina Libraries

35. Shear amplified target DNA to ~400 bp (e.g., via sonication).
36. End Repair of fragmented DNA.
   a. Add NEBNext End Repair Reaction buffer 10×, NEBNext End Repair Enzyme Mix and dH$_2$O to final volume of 100 µL; and
   b. Incubate at 20° C. for 30 minutes.
37. Purify end-repaired DNA (e.g., via 1.6× AMPure XP magnetic beads as in step #2). Elute in 47 µL TE buffer.
38. dA-Tailing of End Repaired DNA
   a. Add NEBNext dA-tailing Reaction buffer (10×) and Klenow fragment to final volume of 50 µL; and
   b. Incubate in a thermal cycler for 30 minutes at 37° C.
39. Purify end-repaired DNA (e.g., via 1.6× AMPure XP magnetic beads as in step #2). Elute in 30 µL TE buffer.
40. Indexed Adapter Ligation of dA-tailed DNA.
   a. Add Quick Ligation Reaction Buffer (5×), NEBNext Adaptor and Quick T4 DNA Ligase to final volume of 50 µL;
   b. Incubate at 20° C. for 15 minutes; and
   c. Add USER Enzyme Mix and mix by pipetting. Incubate at 37° C. for 15 minutes.
41. Purify end-repaired DNA (e.g., via 1.6× AMPure XP magnetic beads as in step #2). Elute in 105 µL TE buffer.
42. Size select Adaptor Ligated DNA using AMPure XP beads per NEBNext protocol. Elute in 17 µL TE buffer.
43. PCR enrichment of Adaptor-ligated DNA.
   a. Add indexing primer mix of choice and NEBNext Q5 Hot Start HiFi PCR Master Mix to 50 µL final volume; and
   b. Put reactions in thermal cycler with cycling conditions per NEBNext protocol.
44. Purify indexed, amplified DNA via 0.9× AMPure XP magnetic beads as in step #2. Elute in 30 µL TE buffer.
45. Sequence target-enriched DNA using Illumina MiSeq or NextSeq instrument.

EXAMPLES

Example 1

Use of Two Biotinylated PCR Primers Mediates Capture of 99% of a Long, Double-Stranded PCR Product The ability of a covalently-bound biotin hapten to mediate capture of very long DNA molecules was evaluated. Since the binding capacity of streptavidin-coated magnetic beads is limited, a single biotin residue per DNA molecule may not be sufficient to compete with free biotinylated probes.

To evaluate the capture of biotinylated PCR products, based on the use of one or more biotinylated PCR primers, a single biotinylated PCR primer was used to capture a long, double-stranded PCR product 3,581 base pairs in length in the presence of 0.5 µM biotinylated probe competitor. The experiment was also carried out using two biotinylated PCR primers. DNA material remaining in supernatant after capture of biotinylated PCR products was visualized and quantified on an agarose gel.

Materials and Methods

Two different biotinylated DNA targets were produced via PCR amplification of a 3,581 bp region of the human mitochondrial DNA genome using either forward and reverse biotinylated primers (2× biotin) or a forward biotinylated primer and capture reactions consisted of 100 ng of biotinylated DNA target, 375 ng of unbiotinylated Lambda/HindIII DNA and increasing concentrations of competitor biotinylated probe ("comp") as indicated. The DNA mixture was added to 250 µg of paramagnetic M280 streptavidin DYNABEADS® along with Kilobasebinder Binding Buffer. The mixture was incubated with rotation for 2 hours at room temperature. DYNABEADS® plus any bound biotinylated DNA was separated from the mixture by incubation on a magnet. The unbound DNA mixture was electrophoresed on a 0.5% agarose gel for 16 hours at 60 V. The gel was stained and a digital image was captured. Densitometry was performed using ImageJ software. The ratio of the intensity of the biotinylated target band to the Lambda/HindIII 9416 bp band normalized to input was visualized. A target band at 3581 by corresponded to the biotinylated PCR product.

Results

In the single-biotin capture experiment, about 57% of the PCR product remains in the supernatant in the presence of 0.5 µM competitor biotinylated probe, as determined by quantitation analysis of gel bands. Bands corresponding to a nucleic acid fragment 3,581 bp in length could be observed in the gel in the presence of biotinylated probe competitor at a concentration of 0.25 µM and 0.5 µM. By contrast, the use of two biotinylated PCR primers was sufficient for high yield capture of a long, double-stranded PCR product that is 3,581 base pairs in length, even in the presence of 0.5 µM biotinylated probe competitor.

Only 1% of the PCR product remained in the supernatant, as observed in the gel, corresponding to 99% capture.

Example 2

PNA Probes with Gamma Modifications of the PNA Backbone Capture Long, Double-Stranded DNA The ability of PNA probes including gamma modifications of the PNA backbone to mediate capture of very long DNA molecules was evaluated. DNA material remaining in supernatant after strand invasion and capture of target DNA with one or two biotinylated PNA probes, each 20 bases long, that contain 6 gamma-Lysine modifications and 1 gamma Mini-PEG modification was visualized and quantified on an agarose gel.

Materials and Methods

Strand invasion reactions consisted of 100 ng of 11,970 bp DNA target (PCR product capturing a genomic region that contains the human CCR5 gene), 375 ng of Lambda/HindIII nontarget DNA, 2 µM single-stranded DNA binding protein (SSB), 20 mM Tris-HCl pH 8.0, 20 mM NaCl, 0.1 mM EDTA, and 0.4 µM PNA(s). Controls (Cont.) contained no PNA or SSB. Reactions were incubated at 46° C. for 4 hours, then 55° C. for 5 minutes. To separate DNA from free PNA probe the reactions were run over P100 size exclusion columns (Bio-Rad). Controls and PNA-containing experimental lanes were loaded in duplicate. Capture reactions and collection of unbound DNA were carried out. Samples were analyzed by gel electrophoresis and densitometry.

To assess the efficiency of capture, three rows of densitometry ratios were calculated from the intensity of bands observed in the gel. The fraction of target DNA not bound was calculated as the relative amount of target DNA remaining in solution after capture. The intensity of the target DNA band was normalized to the Lambda/HindIII 2322 bp non-target band. Actual capture was calculated as 1−(Fraction of Target Not Bound). Each ratio was determined relative to one of the controls in that set.

The Fraction of Non-target Not Bound was calculated as a function of the specificity of capture by the PNA probe(s). This value was determined as the ratio of the Lambda/HindIII 9416 bp non-target band to the 2322 bp non-target band. The Non-target Normalized Recovery was calculated as the ratio of the "Fraction of Target Not Bound" value over the "Fraction of Non-target Not Bound" value. This value provided the fraction of the total captured material that was specific to the target band at 11,970 bp (i.e., DNA specifically targeted by PNA probes).

Results

The use of a single biotinylated PNA capture probe was not sufficient for double-stranded DNA capture for a target DNA that is 11,970 base pairs in length. By contrast, the use of two (or more) biotinylated PNA capture probes was sufficient for high-yield double-stranded DNA capture for a target DNA that is 11,970 base pairs in length. The material remaining in the supernatant after capture, visualized in a gel band at 11,970 kb ranged from 1.4% to 14.9%. Thus, capture yield from two biotinylated PNA probes within the DNA fragment ranged from 98.5% to 85.1%.

Example 3

A Single Target Gene can be Captured from a Preparation of Genomic DNA with an Average Size of 10 kb Capture of long, double stranded DNA by strand-invading PNA probes was utilized to isolate DNA segments of interest from total genomic DNA. An experiment was carried out to determine whether a genomic region containing the CCR5 gene can be captured from a preparation of genomic DNA with an average size of 10 kb.

Materials and Methods

A single PNA probe 20 bases long containing 6 gamma-Lysine modifications and 1 gamma Mini-PEG modification was used. Semi-quantitative PCR was carried out using sheared genomic DNA captured by one PNA probe as template. 3 µg of human genomic DNA (Coriell #NA23248) was sheared to an average size of 10 kb using the Covaris g-TUBE™. Sheared genomic DNA was combined with 2 µM single-strand binding protein (SSB), 20 mM Tris-HCl pH 8.0, 20 mM NaCl, 0.1 mM EDTA and 0.4 µM CCR 6K PNA and incubated at 46° C. for four hours, followed by 55° C. for 5 minutes. A control sample containing no PNA was also included. Size exclusion was performed via a P100 column and biotinylated DNA was captured with M280 streptavidin DYNABEADS®. The DYNABEADS® and bound DNA were separated via magnet and unbound DNA from the supernatant was saved ("supernatant"). DYNABEADS® and bound DNA were washed twice with wash buffer and bound DNA was eluted from the beads in 20 mM Tris-HCl, 200 mM NaCl, 0.1 mM EDTA and 20% formamide by incubating at 65° C. for 5 minutes with agitation ("eluate").

Bound DNA "eluate" and "supernatant" samples were concentrated and purified via AMPure XP beads and eluted in dH$_2$O. Alternative methods of concentrating and purifying these samples include, but are not limited to, Qiagen PCR Purification Kit (catalog #28104) and traditional phenol-chloroform extraction. Semi-quantitative PCR using primers for the specific genomic target (CCR5 gene region, chromosome 3, "CCR 11055s") and a control non-target genomic region (AR gene region, chromosome X, "AR 9827s") was performed with Phusion DNA polymerase. Semi-quantitative PCR products were electrophoresed on 0.8% agarose gels, stained and a digital image was captured. Semi-quantitative PCR using the aforementioned primers and sheared genomic DNA starting material as template was also carried out ("Input").

Results

Based on electrophoresis of semi-quantitative PCR products, the "supernatant" contained about 50% of the CCR5 genomic DNA, indicating PNA-based capture of the genomic DNA fragment is incomplete because a single PNA probe was used.

Example 4

Figure 3:
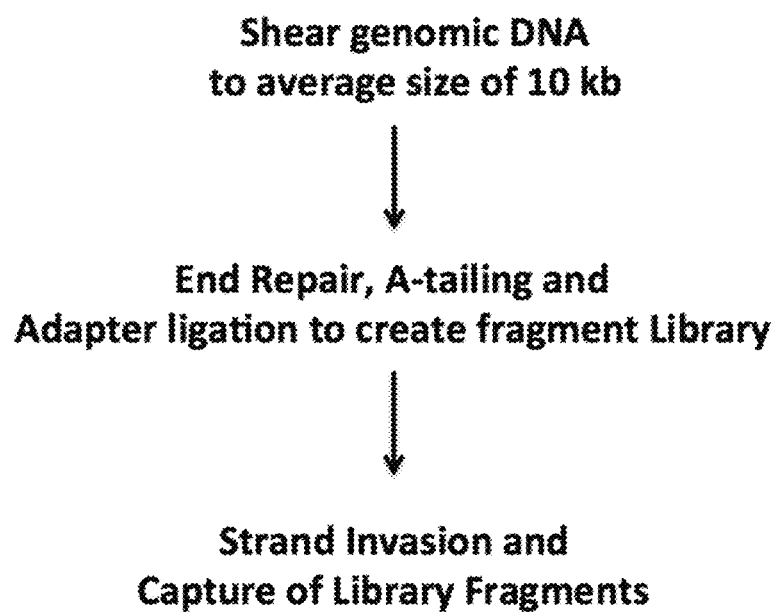
FIG. 3 is a schematic representation of the methodology for strand invasion and capture of a specific double-stranded DNA fragment from a sequencing library.
Figure 4A:
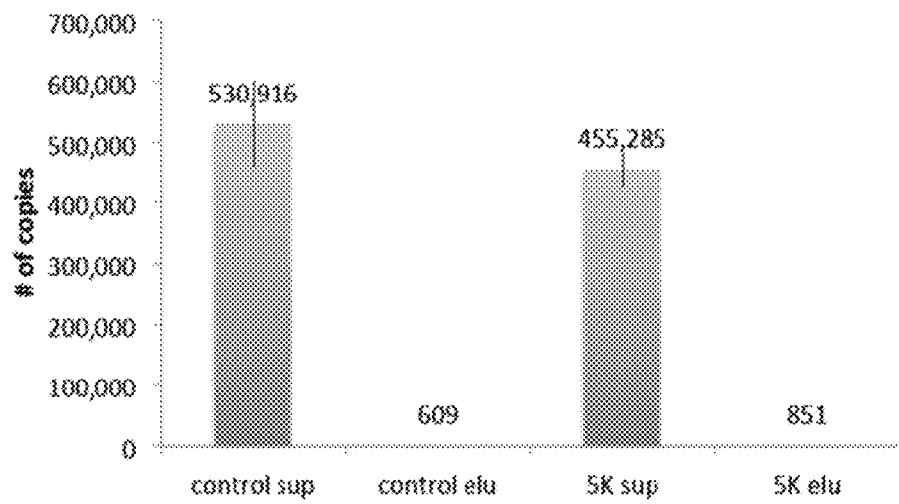
FIGS. 4A-4D are histograms showing the comparative number of copies of DNA fragments in solutions of no PNA control supernatant (control sup), no PNA control elution (control elu), 5K/2 MP PNA supernatant (5K sup) and 5K/2 MP PNA elution (5K elu) respectively, for each of four genomic amplicons analyzed via quantitative real-time PCR, 18S 50 w/75e (FIG. 4A); 5S 50 w/75e (FIG. 4B); CCR 50 w/75e (FIG. 4C); and AR 50 w/75e (FIG. 4D), respectively. Numerical values of copies of DNA fragments in each solution are indicated above each bar.
Figure 4B:
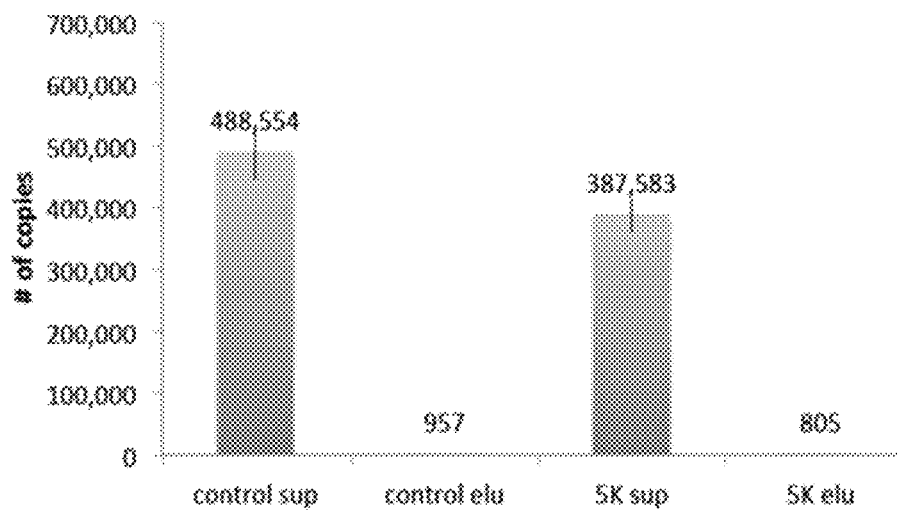
Figure 4C:
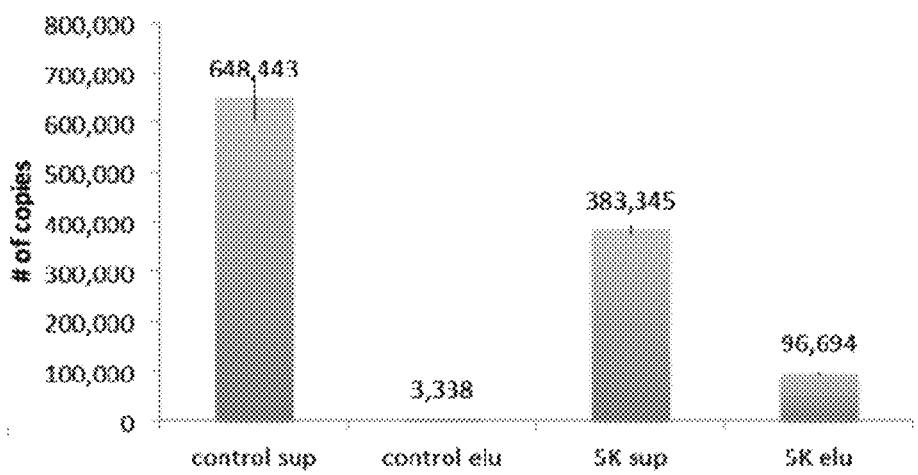
Figure 4D:
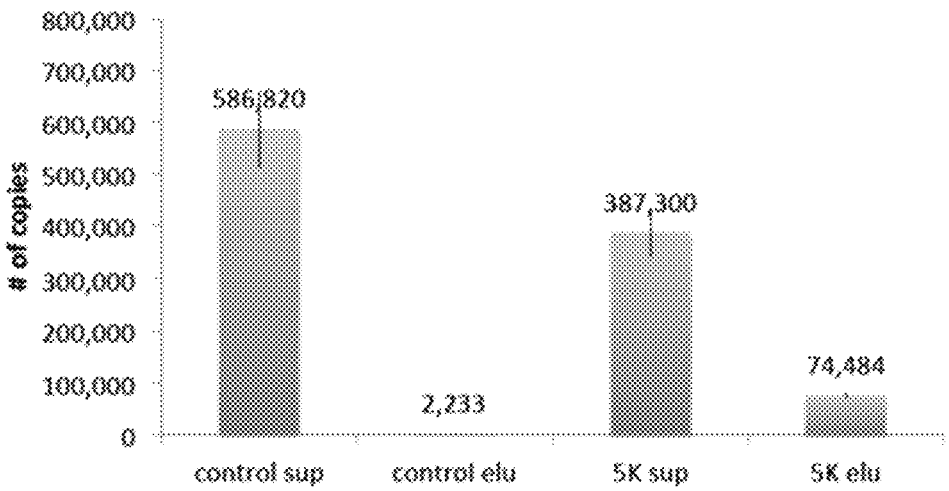
Figure 5:
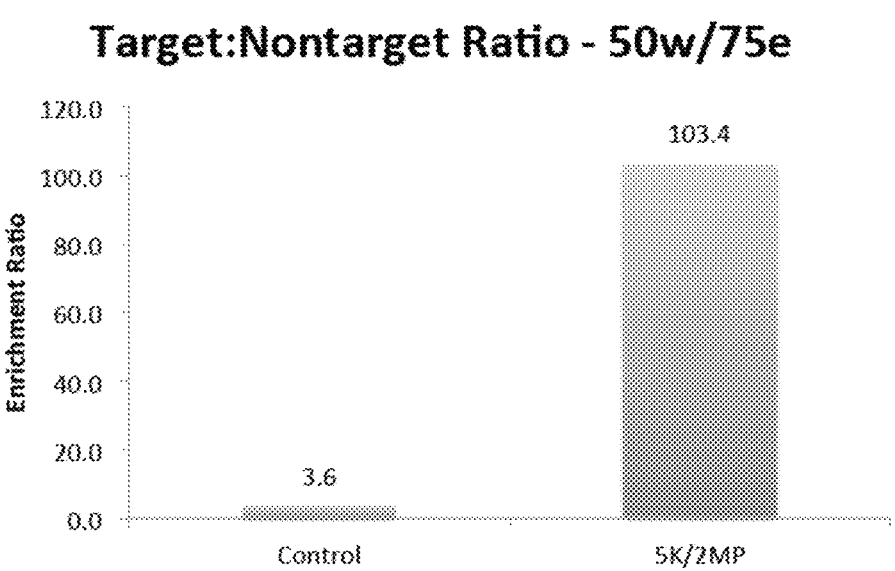
FIG. 5 is a histogram showing the enrichment ratio of target (CCR+AR) to Non-target (18S+5S) comparative number of copies of DNA fragments in solutions of control eluate (control), and using the 5K/2MP PNA set targeting the CCR5 and AR1 regions, respectively. Numerical values of ratios in each solution are indicated above each bar.

PNA Probes can Isolate DNA Segments of Interest from Genomic Library Constructed Using DNA Sequencing Protocols Capture of long, double stranded DNA by strand-invading PNA probes can be utilized to isolate DNA segments of interest from a genomic library constructed using DNA sequencing protocols. For example, this procedure can be carried out using the experimental workflow shown in FIG. 3.

Materials and Methods

A single PNA probe was used in the experiment. The probe was 20 bases long, and contained 6 gamma-Lysine modifications and 1 gamma Mini-PEG modification. Semi-quantitative PCR was carried out using genomic library DNA captured by one PNA probe as template.

Briefly, 3 µg of human genomic DNA (Coriell #NA23248) was sheared to an average size of 10 kb with Covaris g-TUBE™. DNA adapters were ligated onto repaired DNA ends. Adapter-ligated genomic DNA was combined with 2 µM single-strand binding protein (SSB) in 20 mM Tris-HCl (pH 8.0), 20 mM NaCl, 0.1 mM EDTA and 0.4 µM PNA. A control sample containing no PNA was also included.

Size exclusion was performed via a P100 column and biotinylated DNA was captured with M280 streptavidin DYNABEADS®. The DYNABEADS® and bound DNA were separated via magnet and unbound DNA from the supernatant was saved ("supernatant"). DYNABEADS® and bound DNA were washed twice with wash buffer and bound DNA was eluted from the beads in 20 mM Tris-HCl, 200 mM NaCl, 0.1 mM EDTA and 20% formamide by incubating at 65° C. for 5 minutes with agitation ("eluate").

Bound DNA "eluate" and "supernatant" samples were concentrated and purified via AMPure XP beads and eluted in $dH_2O$. Alternative methods of concentrating and purifying these samples include, but are not limited to, Qiagen PCR Purification Kit (catalog #28104) and traditional phenol-chloroform extraction.

Semi-quantitative PCR using primers for the specific genomic target (CCR5 gene region, chromosome 3, "CCR 11055s") and a control non-target genomic region (AR gene region, chromosome X, "AR 9827s") was performed with Phusion® DNA polymerase. Semi-quantitative PCR products were electrophoresed on 0.8% agarose gels, stained and a digital image was captured.

Results

To demonstrate that PNA probes can isolate DNA segments of interest from a genomic library, a genomic region containing the CCR5 gene was specifically captured from a genomic sequencing library that was constructed from fragments of 10 kilobases in length.

The captured material contains CCR5 genomic DNA, but capture is incomplete because only a single PNA probe was used. DNA from the AR gene region of the genome was absent in the "eluate" fraction.

Example 5

Use of Three PNA Probes in Combination Yield Highly Efficient Sequence-Specific Capture of Genomic Library DNA Experiments were conducted to determine whether a genomic region containing the androgen receptor (AR) gene can be specifically captured from a genomic sequencing library that was constructed from fragments 10 kilobases in length. The amount of DNA captured by three PNA probes as template was determined by semi-quantitative PCR.

Materials and Methods

3 µg of human genomic DNA (Coriell #NA23248) was sheared to an average size of 10 kb with Covaris g-TUBE™. DNA adapters were ligated onto repaired DNA ends. Adapter-ligated genomic DNA was combined with 2 µM single-strand binding protein (SSB), 20 mM Tris-HCl (pH 8.0), 20 mM NaCl, 0.1 mM EDTA and 0.4 µM of each of three PNAs targeting a region of the human AR gene and incubated at 46° C. for four hours and then at 55° C. for 5 minutes.

Each of the three PNA probes used in this experiment was 20 bases long, and contained 6 gamma-Lysine modifications and 1 gamma Mini-PEG modification.

A control sample containing no PNA was also included. Size exclusion was performed via a P100 column and biotinylated DNA was captured with M280 streptavidin DYNABEADS®. The DYNABEADS® and bound DNA were separated via magnet and unbound DNA from the supernatant was saved ("supernatant"). DYNABEADS® and bound DNA were washed twice with wash buffer and bound DNA was eluted from the beads in 20 mM Tris-HCl, 200 mM NaCl, 0.1 mM EDTA and 20% formamide by incubating at 65° C. for 5 minutes with agitation ("eluate").

Bound DNA eluate and supernatant samples were concentrated and purified via AMPure XP beads and eluted in $dH_2O$. Alternative methods of concentrating and purifying these samples include, but are not limited to, Qiagen PCR Purification Kit (catalog #28104) and traditional phenol-chloroform extraction.

Semi-quantitative PCR using primers for one of the specific genomic targets (AR gene region, chromosome X, "AR 9827s") and two different control non-target genomic regions (CCR5 gene region, chromosome 3, "CCR 8925s" and GAPDH gene region, chromosome 12, "GAPDH 281s") was performed with Phusion® DNA polymerase. Semi-quantitative PCR products were electrophoresed on 0.8% agarose gels, stained and a digital image was captured.

Results

Based on semi-quantitative PCR products visualized and quantified on an agarose gel, the captured material contained AR genomic DNA. There was no PCR amplification of AR genomic material in the supernatant. Thus, the use of three PNA probes in combination yields highly efficient capture. Controls included DNA from the CCR region as well as DNA from the GAPDH region of the genome, both of which were absent in the eluate. Thus DNA capture was highly specific.

Example 6

Three PNA Probes in Combination Yield Targeted dsDNA that Maintains the Original Size and Double-Stranded Helical Conformation of the DNA An experiment was performed to evaluate the size and structural integrity of double-stranded DNA molecules after they had been subjected to the process of strand invasion by two biotinylated PNA probes, A9827 and A2486, captured on streptavidin-coated paramagnetic beads, and released under partially denaturing conditions.

Materials and Methods

Capture reactions consisted of 2 different biotinylated PNA probes specific for the AR region of the human genome. Each PNA probe was 20 bases long, and contained 6 gamma-Lysine modifications and 1 gamma Mini-PEG modification. Strand invasion reactions consisted of 400 ng of 11,942 bp DNA target (PCR product capturing a genomic region that contains the human AR gene), 2 µM single-stranded DNA binding protein (SSB), 20 mM Tris-HCl pH 8.0, 20 mM NaCl, 0.1 mM EDTA, and 0.4 µM PNA(s). Controls contained no PNA probes. Reactions were incubated at 46° C. for 4 hours, followed by 55° C. for 5 minutes. To separate DNA from free PNA probe the reactions were run over P100 size exclusion columns (Bio-Rad). The DNA mixture was added to 250 µg of paramagnetic DYNABEAD® M280 streptavidin along with Kilobasebinder Binding Buffer. The mixture was incubated with rotation for 2 hours at room temperature. DYNABEADS® plus any bound biotinylated DNA was separated from the mixture by incubation on a magnet.

The captured DNA was released from the magnetic beads using a denaturing buffer consisting of 20 mM Tris pH 8.0, 200 mM NaCl, 0.1 mM EDTA, 20% formamide, at 65° C. for 5 minutes. The DNA eluted from the DYNABEADS® and the DNA present in the supernatant were concentrated and purified with AMPure XP beads (Agencourt). Alternative methods of concentrating and purifying these samples include, but are not limited to, Qiagen PCR Purification Kit (catalog #28104) and traditional phenol-chloroform extraction. Gel electrophoresis analysis was used to compare the size of captured DNA to the size of the original long double-stranded DNA material. DNA samples were electrophoresed on a 0.7% agarose gel for 3 hours at 125V. The gel was stained and a digital image was captured.

Results

The results demonstrated that the AR DNA (a long, double stranded DNA generated by PCR) migrates at the same position (i.e., a band of 11942 base pairs) in a non-denaturing agarose gel as the original DNA, still present in the supernatant of the capture reactions.

Thus, the method of DNA enrichment, based on strand invasion and capture of double-stranded DNA by a multiplicity of PNA probes yields material after capture and release that maintains the original size and double-stranded helical conformation of the DNA target.

Example 7

Ratios of Gamma-Modified Mini-Peg Residues in PNA Probes can be Optimized for Strand Invasion of Short Double-Stranded DNA Targets A simple strand invasion assay was devised, using short PCR products as DNA strand invasion targets. PNA probes, targeting the same sequence, but having different ratios of mini-peg and 1-lysine modifications were tested.

Materials and Methods

DNA target at a concentration of 8 nanoMolar was placed in a 50 µl reaction volume in a buffer consisting of 20 mM Tris pH 8, 20 mM NaCl, 0.1 mM EDTA. PNA probes were added at a concentration of 0.3 µM. The samples were incubated for 30, 60, 120 or 180 minutes at 52° C. Following incubation samples were chilled, and separated in a 1% agarose non-denaturing gel for 3.5 hours at 125V. The 19-base PNA probes used in the second gel-shift experiment are as provided in Table 5, below.

TABLE 5

19-base PNA probes used in the first gel-shift experiment are as follows:

| Probe ID | Probe Sequence | γ-Lysine | γ-Mini-PEG |
|---|---|---|---|
| C4902/4K/10MP | Biotin-O-O-T*CCCaTgC*aCTTT*TCgaTT* | 4 | 10 |
| C4902/3K/11MP | Biotin-O-O-T*CCCaTgCaC*TTTTCgaTT* | 3 | 11 |
| C4902/2K/12MP | Biotin-O-O-TCCCaT*gCaCTTTTC*gaTT | 2 | 12 |

Standard PNA residues are represented by lowercase font;
PNA residues modified with mini PEG at the gamma-carbon are represented by uppercase font (no asterix; C*, or T*, or A*); and
PNA residues modified with L-lysine at the gamma-carbon are represented by uppercase font (followed by an asterisks; C*, or T*, or A*).

Results

The results of the gel shift analysis using each of the 19-base probes in Table 2 indicated that the C4902/4K/10 MP (21% lysine) probes are more efficient at invading DNA and shifting-up the double-stranded DNA band than C4902/3K/11 MP (16% lysine) probes. The C4902/2K/12 MP probes (10.5% lysine) were the least efficient, producing no observable strand invasion under these conditions.

Example 8

Content of Positively-Charged Gamma-L-Lysine Residues in PNA Probes can be Optimized for Strand Invasion To determine the impact of gamma-lysine versus minipeg content, PNA probes targeting the same sequence, but having different ratios of mini-peg with the same or subtly different content of 1-lysine modifications were tested.

Methods

In a similar experiment as in Example 7, but utilizing a slightly higher probe concentration, a DNA target at a concentration of 14 nanoMolar was placed in a 50 µl reaction volume in a buffer consisting of 20 mM Tris pH 8, 20 mM NaCl, 0.1 mM EDTA. PNA probes were added at a concentration of 0.5 µM. The samples were incubated for 30, 60, 120 or 180 minutes at 52° C. Following incubation the samples were chilled, and separated in a 1% agarose non-denaturing gel for 3.5 hours at 125V. The 19-base PNA probes used in the second gel-shift experiment are as provided in Table 6, below.

TABLE 6

19-base PNA probes used in the first gel-shift experiment

| Probe ID | Probe Sequence | γ-Lysine | γ-Mini-PEG |
|---|---|---|---|
| C4902/4K/10MP | Biotin-O-O-T*CCCaTgC*aCTTT*TCgaTT* | 4 | 10 |
| C4902/5K/4MP | Biotin-O-O-tC*cCaT*gCaC*tTtT*CgaT*t | 5 | 4 |
| C4902/5K/1MP | Biotin-O-O-tC*ccAtgC*acT*ttT*cgA*tt | 5 | 1 |

Standard PNA residues are represented by lowercase font;
PNA residues modified with mini PEG at the gamma-carbon are represented by uppercase font (no asterix; C*, or T*, or A*); and
PNA residues modified with L-lysine at the gamma-carbon are represented by uppercase font (followed by an asterix; C*, or T*, or A*).

Results

The results of the gel shift analysis with the 19-base probes in Table 5 indicated that 5K/1MP (26% lysine) and 5K/4 MP (26% lysine) probes are equally efficient at invading DNA and shifting-up the double-stranded DNA band. The 4K/10 MP (21% lysine) probes are somewhat less efficient that the 5K/1 Mp and the 5K/4 MP probes.

These results suggest that the content of positively charged gamma-L-lysine residues in the PNA is at least as influential as the content of the mini-PEG content for producing efficient strand invasion. The invasion reaction is essentially complete after 2 hours of incubation at 52° C.

Example 9

Protocol for Sequence Enrichment of a Desired Fragment of Double-Stranded DNA from a Mixture Containing Multiple Restriction Fragments of Phage Lambda DNA To demonstrate the ability of the methods to enrich a desired fragment of 8500 from a DNA sample containing multiple restriction fragments of phage lambda DNA base pairs, the following protocol was designed.

Methods

Pairs of PNA Probes used included either 4 gamma-L-Lysine modifications and 3 gamma-Mini-Peg modifications (C5391 4K/3 MP+C8925 4K/3 MP; 4K Pair), or 6 gamma-L-Lysine modifications and 1 gamma-Mini-Peg modification (C5391 6K/1MP+C8925 6K/1MP; 6K Pair).

1. Prepare probes by heating at 65° C. for 10 minutes. Vortex and spin down.
2. Combine 375 ng Lambda/HindIII DNA, 200 ng CCR 8500 target, 20 pmol per probe, 5× SI buffer, 1.95 µL SSB, 7. 2 µL Formamide and H$_2$O to a total volume of 50 µL; final concentrations are 400 nM of each probe, 41.7 mM NaCl, 1.5 µM M SSB, 14% formamide.
3. Make 5 samples as above but do not add probe to one tube ("– control")
4. Briefly vortex each tube and spin down to get all liquid at the bottom.
5. Incubate at 46° C. or 50° C. for 4 hours then incubate at 55° C. or 60° C. for 5 minutes.
6. Purify the DNA from the free probe by AMPure XP beads. Elute in 50 µL TE.
7. Combine purified reaction with BSA passivated C1 beads+50 µL binding buffer+100 µL H$_2$O.
8. Incubate capture reactions at room temperature on rotator for 2 hours.
9. Take samples off of rotator and put on magnet for 3 minutes. (Transfer supernatant to new tube.)
10. Add 150 µL 0.02% TWEEN® Wash buffer to beads, resuspend by pipetting, mix for 30 seconds, put on magnet for 2 mins. Discard wash buffer.
11. Repeat wash step four times, and discard wash.
12. Add 100 µL elution buffer (10 mM Tris pH 8, 400 mM NaCl, 0.1 mM EDTA, 20% formamide) to washed beads, vortex, spin, and incubate at 65° C. for 5 minutes with agita-on (800) in thermomixer.
13. Place tubes on magnet for 3 minutes. Transfer eluted material to new tube.
14. Purify DNA with AMPure XP beads (0.8:1 ratio), wash 2× with 80% ethanol, elute in 40 µL dH$_2$O.
15. In 0.2 mL plastic tubes, mix 20 µL of supernatant or purified eluate with 5 µL loading dye.
16. Load DNA samples on 0.5% agarose gel and run at 60V for 16 hours with water chiller at 5° C.
17. Stain gel with Diamond Nucleic Acid Stain (e.g., for 45 minutes).
18. Rinse gel and visualize (e.g., on Enduro Gel Doc System).

Results

The best enrichment (83:1) was obtained with the 4K/3 MP PNA probes. Although the 6K/1MP probes were competent for target capture, they also non-specifically captured the lambda DNA, and bands appeared in the eluate. This non-specific capture can be seen clearly on a gel.

Example 10

Protocol for Sequence Enrichment of Specific Fragments of 8 Kb, Double-Stranded Genomic DNA from Total Human Genomic DNA To demonstrate the ability of the methods to enrich a desired fragment of 8,000 base pairs from total human genomic DNA, the following protocol was designed.

Methods

Pairs of PNA Probes used included either 5 gamma-L-Lysine modifications and 1 or 2 gamma-Mini-Peg modifications (C4902 5K/1MP+C5391 5K/2MP+A1767 5K/1MP+ A2486 5K/2MP; 5K/2MP Pairs). Controls for non-specific capture were 18S and 5S ribosomal DNA. The experiment was conducted according to the following conditions:

1. Prepare probes by heating at 65° C. for 10 minutes, then vortex and spin down.
2. Combine 1 µg NA23248 g DNA (sheared to 15 kb fragments), 1.5 ng CCR8250 target DNA, 1.5 ng AR9127 target, 20 pmoles each probe, 5× SI buffer, 2.60 µL SSB, 7.2 µL Formamide and add H$_2$O to a total volume of 50 µL. Final concentrations were 400 nM each probe, 41.7 mM total NaCl, 2 µM SSB, 14% formamide
3. Probe concentration 200 nM each; make 2 samples and do not add probe to one tube ("control")–1 no probe samples+1 samples containing all probes.
4. Briefly vortex each tube and spin down to get all liquid at the bottom.
5. Place tubes in dry bath and incubate at 50° C. for 4 hours then incubate at 60° C. for 5 minutes.
6. Purify the DNA from the free probe by 1i xX P100 column. Spin at 100×g for 4 minutes.
7. Combine purified SI reaction with BSA passivated C1 magnetic beads+100 µL H$_2$O.
8. Incubate capture reactions at room temperature on rotator for 2 hours.
9. Take samples of rotator and put on magnet for 3 minutes. Transfer supernatant to new tube.
10. Add 150 µL 0.02% Tween Wash buffer to beads, resuspend by pipetting, vortex for 30 sec, put on magnet for 2 mins. Discard wash buffer.
11. Repeat wash three times and discard washes.
12. Add 150 µL 0.02% Tween Wash buffer, re-suspend and incubate in thermomixer at 50° C.×7 min.
13. Add 100 µL elution buffer (10 mM Tris pH 8, 400 mM NaCl, 0.1 mM EDTA, 20% formamide) to washed beads, vortex, spin and incubate at 75° C. for 7 minutes with agitation in thermomixer.
14. Place tubes on magnet for 3 minutes. Transfer eluate to new tube.
15. Purify supernatants and eluted DNA with AMPure XP beads, wash 2× with ethanol, elute in 40 µL dH$_2$O. Purify supernatants and eluted DNA with AMPure XP beads, wash 2× with ethanol, elute in 40 µL dH$_2$O.
16. Prepare qPCR using Control sup, Control eluate, PNA sup and PNA eluates as templates.

Results

In this experiment the human DNA was spiked with 9,000 base PCR products for the target genes, in order to attain a target gene copy number identical to the number of copies of the ribosomal genes.

Results are illustrated as histograms depicting numerical values of copies of DNA in each sample in FIGS. 4A-4D. The histogram bars labeled "control sup" refer to material remaining in the supernatant, while "control elu" refers to captured DNA detected in the eluate in the experiments where PNA probes are omitted.

The four different PNA probes used, two targeted the Androgen Receptor (AR) gene, and another two targeting the CCR5 gene. All probes have 5 gamma-L-lysine residues and either one or two gamma-mini-PEG residues. The histogram bars labeled "5K sup" refer to material remaining in the supernatant, while "5K elu" refers to captured DNA detected in the eluate in the experiments where 5K-PNA probes are present.

The control eluates for 18S and 5S ribosomal DNA contained less than 1,000 captured molecules. By contrast, the 5K eluates contained 96,694 and 74,484 captured target molecules for the CCR5 and AR gene regions, respectively.

These numbers corresponded to an average target enrichment level of 103.4-fold for both genes.

REFERENCES

Bahal R, Sahu B, Rapireddy S, Lee C M, Ly D. Sequence-Unrestricted, Watson-Crick Recognition of Double Helical B-DNA by (R)-MiniPEG-gPNAs ChemBioChem 2012, 13, 56-60.

Bahal R, McNeer N A, Ly D H, Saltzman W M, Glazer P M. Nanoparticle for delivery of antisense γPNA oligomers targeting CCR5. Artificial DNA PNA XNA. 2013 April-June; 4(2):49-57.

Bahal R, Quijano E, McNeer N A, Liu Y, Bhunia D C, Lopez-Giraldez F, Fields R J, Saltzman W M, Ly D H, Glazer P M. Single-stranded γPNAs for in vivo site-specific genome editing via Watson-Crick recognition. Curr Gene Ther. 2014; 14(5):331-42.

Brudno Y, Birnbaum M E, Kleiner R E, Liu D R. An in vitro translation, selection and amplification system for peptide nucleic acids. Nat Chem Biol. 2010 February; 6(2):148-155.

Burgtorf C1, Kepper P, Hoehe M, Schmitt C, Reinhardt R, Lehrach H, Sauer S. Clone-based systematic haplotyping (CSH): a procedure for physical haplotyping of whole genomes. Genome Res. 2003 December; 13(12):2717-24.

Buske F A1, Bauer D C, Mattick J S, Bailey T L. Triplex-Inspector: an analysis tool for triplex-mediated targeting of genomic loci. Bioinformatics. 2013 Aug. 1; 29(15): 1895-7. doi: 10.1093/bioinformatics/btt315. Epub 2013 Jun. 5.

Cantor, C R, Smith, C L. Sequence-specific manipulation of DNA. Chapter 14 pp. 470-525 in Genomics: The Science and Technology Behind the Human Genome Project. Charles R. Cantor, Cassandra L. Smith, authors, Publisher: Wiley-Interscience; 1 edition (Feb. 2, 1999) ISBN: 978-0-471-59908-1

Chung, W Y, Schmitz, R J, Biorac, T, Ye, D, Dudas, M, Meredith, G D, Adams, C C Ecker, J R and Zhang, M Q. Constructing Hepitypes: Phasing Local Genotype and DNA Methylation. Journal of Neuroscience and Neuroengineering Vol. 2, pp. 1-12, 2013.

Clark T A, Lu X, Luong K, Dai Q, Boitano M, Turner S W, He C, Korlach J. Enhanced 5-methylcytosine detection in single-molecule, real-time sequencing via Tet1 oxidation. BMC Biol. 2013 Jan. 22; 11:4. doi: 10.1186/1741-7007-11-4.

De Costa N T, Heemstra J M. Evaluating the effect of ionic strength on duplex stability for PNA having negatively or positively charged side chains. PLoS One. 2013; 8(3): e58670. doi: 10.1371/journal.pone.0058670. Epub 2013 Mar. 6.

De Costa N T, Heemstra J M. Differential DNA and RNA sequence discrimination by PNA having charged side chains. Bioorg Med Chem Lett. 2014 May 15; 24(10): 2360-3. doi: 10.1016/j.bmcl.2014.03.059. Epub 2014 Mar. 28.

Demidov V V, Bukanov N O, Frank-Kamenetskii D. Duplex DNA capture. Curr Issues Mol Biol. 2000 January; 2(1): 31-5. Review.

Dueholm, K. L.; Petersen, K. H.; Jensen, D. K.; Egholm, M.; Nielsen, P. E.; Buchardt, O. Peptide nucleic acid (PNA) with a chiral backbone based on alanine. Bioorg. Med. Chem. Lett. 1994, 4, 1077-1080.

Dragulescu-Andrasi A, Rapireddy S, Frezza B M, Gayathri C, Gil R R, Ly D H. A simple gamma-backbone modification preorganizes peptide nucleic acid into a helical structure. J Am Chem Soc. 2006 Aug. 9; 128(31):10258-67.

Edgar R C. Search and clustering orders of magnitude faster than BLAST. Bioinformatics. 2010 Oct. 1; 26(19):2460-1. doi: 10.1093/bioinformatics/btq461. Epub 2010 Aug. 12.

Egholm, M., Buchardt, O., Nielsen, P. E., and Berg, R. H. (1992) Peptide nucleic acids (PNA). Oligonucleotide analogues with an achiral peptide backbone. J. Am. Chem. Soc. 114:1895-1897.

Englund, E. A.; Appella, D. H. Synthesis of γ-substituted peptide nucleic acids: A new place to attach fluorophores without affecting DNA binding. Org. Left. 2005, 7, 3465-3467.

Gambari R. Peptide nucleic acids: a review on recent patents and technology transfer, Expert Opinion Ther. Pat. 24(3): 267-294 (2014).

Expert Opin Ther Pat. 2014 March; 24(3):267-94. doi: 10.1517/13543776.2014.863874. Epub 2014 Jan. 3. Review.

Gnirke A, Melnikov A, Maguire J, Rogov P, LeProust E M, Brockman W, Fennell T, Giannoukos G, Fisher S, Russ C, Gabriel S, Jaffe D B, Lander E S, Nusbaum C, Solution hybrid selection with ultra-long oligonucleotides for massively parallel targeted sequencing. Nat Biotechnol. 2009 February; 27(2):182-9. doi: 10.1038/nbt.1523.

Hansen M E, Bentin T, Nielsen P E. High-affinity triplex targeting of double stranded DNA using chemically modified peptide nucleic acid oligomers. Nucleic acids Res. 2009 July; 37(13):4498-507. doi: 10.1093/nar/gkp437. Epub 2009 May 27.

Hasmats J, Gréen H, Orear C, Validire P, Huss M, Käller M, Lundeberg J. Assessment of whole genome amplification for sequence capture and massively parallel sequencing. PLoS One. 2014 Jan. 7; 9(1):e84785. doi: 10.1371.

He G, Rapireddy S, Bahal R, Sahu B, Ly D H. Strand invasion of extended, mixed-sequence B-DNA by gammaPNAs. J Am Chem Soc. 2009 Sep. 2; 131(34):12088-90. doi: 10.1021/ja900228j.

He W, Crawford M J, Rapireddy S, Madrid M, Gil R R, Ly D H, Achim C. The structure of a gamma-modified peptide nucleic acid duplex. Mol Biosyst. 2010 September; 6(9):1619-29. doi: 10.1039/c002254c. Epub 2010 Apr. 13.

Herrmann A, Haake A, Ammerpohl O, Martin-Guerrero I, Szafranski K, Stemshorn K, Nothnagel M, Kotsopoulos S K, Richter J, Warner J, Olson J, Link D R, Schreiber S, Krawczak M, Platzer M, Nürnberg P, Siebert R, Hampe J. Pipeline for large-scale microdroplet bisulfate PCR-based sequencing allows the tracking of hepitype evolution in tumors. PLoS One. 2011; 6(7):e21332. doi: Epub 2011 Jul. 5.

Hodges E, Rooks M, Xuan Z, Bhattacharjee A, Benjamin Gordon D, Brizuela L, Richard McCombie W, Hannon G J. Hybrid selection of discrete genomic intervals on custom-designed microarrays for massively parallel sequencing. Nat Protoc. 2009; 4(6):960-74. doi: 10.1038/nprot.2009.68. Epub 2009 May 28.

Hodges E, Xuan Z, Balija V, Kramer M, Molla M N, Smith S W, Middle C M, Rodesch M J, Albert T J, Hannon G J, McCombie W R. Genome-wide in situ exon capture for selective re-sequencing. Nat Genet. 2007 December; 39(12):1522-7. Epub 2007 Nov. 4.

Huang H, Joe, G H, Choi, S R, Kim, S N, Kim, Y T, Pak, H S, Kim, S K, Hong, J H, Han, H K, Kang, J S, and Lee, W. Preparation and Determination of Optical Purity of γ-Lysine Modified Peptide nucleic acid Analogues. Arch Pharm Res Vol 35, No 3, 517-522, 2012 DOI 10.1007/s12272-012-0315-4

Ishizuka, T.; Yoshida, J.; Yamamoto, Y.; Sumaoka, J.; Tedeschi, T.; Corradini, R.; Sforza, S.; Komiyama, M. Chiral introduction of positive charges to PNA for double-duplex invasion to versatile sequences. Nucleic acids Res. 2008, 36, 1464-1471.

Ishizuka T, Otani K, Sumaoka J, Komiyama M. Strand invasion of conventional PNA to arbitrary sequence in DNA assisted by single-stranded DNA binding protein. Chem Commun (Camb). 2009 Mar. 14; (10):1225-7. Epub 2009 Jan. 14.

Ishizuka T, Tedeschi T, Corradini R, Komiyama M, Sforza S, Marchelli R. SSB-assisted duplex invasion of preorganized PNA into double-stranded DNA. Chembiochem. 2009 Nov. 2; 10(16):2607-12.

Ito T, Smith C L, Cantor C R. Sequence-specific DNA purification by triplex affinity capture. Proc Natl Acad Sci USA. 1992a Jan. 15; 89(2):495-8.

Ito T, Smith C L, Cantor C R. Triplex affinity capture of a single copy clone from a yeast genomic library. Nucleic acids Res. 1992b Jul. 11; 20(13):3524.

Kuhn H, Sahu B, Rapireddy S, Ly D H, Frank-Kamenetskii M D. Sequence specificity at targeting double-stranded DNA with a γ-PNA oligomer modified with guanidinium G-clamp nucleobases. Artif DNA PNA XNA. 2010 July; 1(1):45-53.

Kuleshov, V, Xie, D, Chen R, Pushkarev, D, Ma, Z, Blawkamp, T, Kertesz, M, Snyder, M. Wholoe-genome haplotyping using ong reads and statistical methods. Nat. Biotechnology. 2014

Lohse J, Dahl O, Nielsen P E. Double duplex invasion by peptide nucleic acid: a general principle for sequence-specific targeting of double-stranded DNA. Proc Natl Acad Sci USA. 1999 Oct. 12; 96(21):11804-8.

Lonkar P, Kim K H, Kuan J Y, Chin J Y, Rogers F A, Knauert M P, Kole R, Nielsen P E, Glazer P M. Targeted correction of a thalassemia-associated beta-globin mutation induced by pseudo-complementary peptide nucleic acids. Nucleic acids Res. 2009 June; 37(11):3635-44. doi: 10.1093/nar/gkp217. Epub 2009 Apr. 13.

Murphy, N. M., Pouton, C. W., Irving, H. R., Human leukocyte antigen haplotype phasing by allele-specific enrichment with peptide nucleic acid probes, Molecular Genetics & Genomic Medicine, 2(3):245-253 (2014).

Nielsen, P. E, Apella, D., 2014. Peptide nucleic acids, Methods and Protocols, 2nd Edition ed. (Eds. P. E. Nielsen, D. Appella). Humana Press, Springer media, 2014.

Nielsen, P. E., Egholm, M., Berg, R. H., and Buchardt, O. (1991) Sequence selective recognition of DNA by strand displacement with a thymine substituted polyamide. Science 254, 1497-1500

Ørum H. Purification of nucleic acids by hybridization to affinity tagged PNA probes. Curr Issues Mol Biol. 1999; 1(1-2):105-10.

Ray A, Nordén B. Peptide nucleic acid (PNA): its medical and biotechnical applications and promise for the future. FASEB J. 2000 June; 14(9):1041-60. Review. Chem. Soc. 114, 1895-1897

Sahu B, Sacui I, Rapireddy S, Zanotti K J, Bahal R, Armitage B A, Ly D H. Synthesis and characterization of conformationally preorganized, (R)-diethylene glycol-containing γ-peptide nucleic acids with superior hybridization properties and water solubility. J Org Chem. 2011 Jul. 15; 76(14):5614-27. doi: 10.1021/jo200482d. Epub 2011 Jun. 15.

Santa Lucia J Jr. A unified view of polymer, dumbbell, and oligonucleotide DNA nearest-neighbor thermodynamics. Proc Natl Acad Sci USA. 1998 Feb. 17; 95(4):1460-5.

Schleifman E B, Glazer P M. Peptide nucleic acid-mediated recombination for targeted genomic repair and modification. Methods Mol Biol. 2014; 1050:207-22. doi: 10.1007/978-1-62703-553-8_17.

Schleifman E B, McNeer N A, Jackson A, Yamtich J, Brehm M A, Shultz L D, Greiner D L, Kumar P, Saltzman W M, Glazer P M. Site-specific Genome Editing in PBMCs With PLGA Nanoparticle-delivered PNAs Confers HIV-1 Resistance in Humanized Mice. Mol Ther Nucleic acids. 2013 Nov. 19; 2:e135. doi: 10.1038/mtna.2013.59.

Sugiyama T, Kittaka A. Chiral peptide nucleic acids with a substituent in the N-(2-aminoethy)glycine backbone. Molecules. 2013 Dec. 27; 18(1):287-310. doi: 10.3390/molecules 18010287. Review.

Tedeschi, T.; Sforza, S.; Corradini, R.; Marchelli, R. Synthesis of new chiral PNAs bearing a dipeptide-mimic monomer with two lysine-derived stereogenic centres. Tetrahedron Lett. 2005, 46, 8395-8399.

Tewhey R, Nakano M, Wang X, Pabón-Peña C, Novak B, Giuffre A, Lin E, Happe S, Roberts D N, LeProust E M, Topol E J, Harismendy O, Frazer K A. Enrichment of sequencing targets from the human genome by solution hybridization. Genome Biol. 2009; 10(10):R116. doi: 10.1186/gb-2009-10-10-r116. Epub 2009 Oct. 16.

Tilani N, De Costa S, Heemstra J. Differential DNA and RNA sequence discrimination by PNA having charged side chains. Bioorganic & Medicinal Chemistry Lett. 2014, 24, 2360-2363.

Totsingan F, Jain V, Green M M. Helix control in polymers: case of peptide nucleic acids (PNAs) Artif DNA PNA XNA. 2012 April-June; 3(2):31-44. doi: 10.4161/adna.20572. Epub 2012 Apr. 1. REVIEW Wang M, Beck C R, English A C, Meng Q, Buhay C, Han Y, Doddapaneni H V, Yu F, Boerwinkle E, Lupski J R, Muzny D M, Gibbs R A. PacBio-LITS: a large-insert targeted sequencing method for characterization of human disease-associated chromosomal structural variations. BMC Genomics. 2015 Mar. 19; 16(1):214.

Yeh, J. I.; Boris Shivachev, B.; Rapireddy, S.; Crawford, M. J.; Gil, R. R.; Du, S.; Madrid, M.; Ly, D. H. Crystal structure of chiral γPNA with complementary DNA strand: Insights into the stability and specificity of recognition and conformational preorganization. J. Am. Chem. Soc. 2010, 132, 10717-10727.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Throughout the description and claims of this specification, the word "comprise" and variations of the word, such as "comprising" and "comprises," means "including but not limited to," and is not intended to exclude, for example, other additives, components, integers or steps. Analogously, the word "include" and variations of the word, such as "including" and "includes," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different compositions and methods of use thereof does not indicate that the listed compositions and methods are obvious one to the other, nor is it an admission of equivalence or obviousness.

Those skilled in the art will recognize, or be able to ascertain using no more than routine experimentation, many equivalents to the specific embodiments of the method and compositions described herein. Such equivalents are intended to be encompassed by the following claims.

We claim:

1. A peptide nucleic acid (PNA) hybridization probe comprising at or between 10 to 26 peptide nucleic acid residues,
    wherein the PNA probe is designed to target a sequence in a nucleic acid fragment,
    wherein the PNA probe comprises two or more peptide nucleic acid residues that are derivatized with a charged moiety on, independently for each of the peptide nucleic acid residues derivatized with a charged moiety, the alpha, beta, or gamma carbon, and one or more peptide nucleic acid residues that are derivatized with a neutral moiety on, independently for each of the peptide nucleic acid residues derivatized with a neutral moiety, the alpha, beta, or gamma carbon,
    wherein there is an average of at or between 1.8 to 4.0 peptide nucleic acid residues that are not derivatized with a charged moiety between every peptide nucleic acid residue that is derivatized with a charged moiety, and
    wherein the PNA probe comprises one or more capture tags.

2. The PNA probe of claim 1, wherein the probe comprises at or between 16 to 22 peptide nucleic acid residues.

3. The PNA probe of claim 1, wherein the probe comprises 18 or 19 peptide nucleic acid residues.

4. The PNA probe of claim 1, wherein three, four, five, or six of the peptide nucleic acid residues are derivatized with the charged moieties, wherein one or more of the peptide nucleic acid residues derivatized with the charged moieties are selected from the group consisting of gamma-L-lysine PNA, gamma-L-thialysine PNA, and combinations thereof, wherein at or between two to six of the peptide nucleic acid residues that are not derivatized with the charged moieties are derivatized with diethylene glycol, and wherein the capture tag is biotin.

5. The PNA probe of claim 1, wherein four of the peptide nucleic acid residues are gamma-L-lysine PNA, wherein four of the peptide nucleic acid residues are derivatized with diethylene glycol, and wherein the capture tag is biotin.

6. The PNA probe of claim 1, wherein four of the peptide nucleic acid residues are gamma-L-thialysine PNA, wherein four of the peptide nucleic acid residues are derivatized with diethylene glycol, and wherein the capture tag is biotin.

7. The PNA probe of claim 1, wherein there is an average of at or between 0.4 to 1.5 peptide nucleic acid residues that are not derivatized with a moiety between every peptide nucleic acid residue that is derivatized with a moiety.

8. The PNA probe of claim 1, wherein every peptide nucleic acid residue is derivatized with a charged moiety or a neutral moiety.

9. The PNA probe of claim 1, wherein at or between 15% to 28% of the peptide nucleic acid residues of the PNA probe are derivatized with a charged moiety.

10. The PNA probe of claim 1, wherein there are at least two peptide nucleic acid residues that are not derivatized with a charged moiety between every peptide nucleic acid residue that is derivatized with a charged moiety.

11. The PNA probe of claim 1, wherein one or more of the peptide nucleic acid residues that are derivatized with the charged moiety are derivatized with the charged moiety on the gamma carbon.

12. The PNA probe of claim 1, wherein one or more of the peptide nucleic acid residues that are derivatized with the charged moieties are L-thialysine peptide nucleic acid residues.

13. The PNA probe of claim 1, wherein one or more of the peptide nucleic acid residues that are derivatized with the charged moieties are L-lysine peptide nucleic acid residues.

14. The PNA probe of claim 1, wherein at or between 4% to 85% of the peptide nucleic acid residues of the PNA probe are derivatized with a neutral moiety.

15. The PNA probe of claim 1, wherein one or more of the peptide nucleic acid residues that are derivatized with a neutral moiety are derivatized on the gamma carbon.

16. The PNA probe of claim 1, wherein one or more of the neutral moieties is a short-chain oligoethylene moiety.

17. The PNA probe of claim 16, wherein one or more of the short-chain oligoethylene moieties are diethylene glycol.

18. The PNA probe of claim 1, wherein the capture tag is biotin or streptavidin.

19. The PNA probe of claim 1, wherein the PNA probe targets (a) a sequence in human genomic DNA located in the MHC region of chromosome 6; (b) a sequence in human genomic DNA associated with one or more diseases or conditions or having a known correlation with development of one or more disease or conditions, wherein the diseases or conditions are selected from the group consisting of autoimmune diseases, diabetes, metabolic syndrome, and cancer; (c) a sequence in human genomic DNA at different positions that map to a multiplicity of enhancer elements associated with disease risk for autoimmune diseases; (d) a sequence in human genomic DNA at different positions that map to a multiplicity of enhancer elements associated with disease risk for diabetes and the metabolic syndrome; (e) a sequence in human genomic DNA at different positions that map to a multiplicity of enhancer elements associated with the differentiation of different subsets of white blood cells; (f) a sequence in human mitochondrial DNA; (g) a sequence in dog mitochondrial DNA; or (h) a sequence in genomic DNA of one or more parasites selected from the group consisting of bacteria, archaea, fungi, protozoa, or mixtures thereof.

20. The PNA probe of claim 1, wherein the PNA probe targets a sequence in genomic DNA of one or more parasites selected from the group consisting of bacteria, archaea, fungi, protozoa, or mixtures thereof, wherein the bacteria is one or more species of bacteria present in human oral cavity, human airway, human urogenital tract, human blood, or human feces.

21. A set of two or more PNA probes, wherein at least one of the PNA probes is a PNA probe of claim 1, wherein the PNA probes in the same set of two or more PNA probes are designed to target a different sequence in the same nucleic acid fragment, wherein the PNA probes in different sets of two or more PNA probes are designed to target different nucleic acid fragments.

22. The set of claim 21, wherein all of the PNA probes are a PNA probe, wherein each PNA probe independently (a) comprises at or between 10 to 26 peptide nucleic acid residues, (b) is designed to target a sequence in a nucleic acid fragment, (c) comprises one or more peptide nucleic acid residues that are derivatized with a charged moiety on the alpha, beta, or gamma carbon or combinations thereof, and one or more peptide nucleic acid residues that are derivatized with a neutral moiety on the alpha, beta, or gamma carbon, or combinations thereof, and (d) comprises one or more capture tags.

23. The set of claim 21, wherein in one or more of the PNA probes there is an average of at or between 1.0 to 5.0 peptide nucleic acid residues that are not derivatized with a charged moiety between every peptide nucleic acid residue that is derivatized with a charged moiety.

24. The set of claim 21, wherein in one or more of the PNA probes there is an average of at or between 0.5 to 1.5 peptide nucleic acid residues that are not derivatized with a moiety between every peptide nucleic acid residue that is derivatized with a moiety.

25. The set of claim 21, wherein independently in one or more of the PNA probes one or more of the peptide nucleic acid residues that are derivatized with the charged moiety are derivatized with the charged moiety on the gamma carbon.

26. The set of claim 21, wherein in all of the PNA probes one or more of the peptide nucleic acid residues that are derivatized with the charged moiety are derivatized with the charged moiety on the gamma carbon.

27. The set of claim 21, wherein in one or more of the PNA probes one or more of the peptide nucleic acid residues that are derivatized with the charged moieties are L-thialysine peptide nucleic acid residues.

28. The set of claim 21, wherein in one or more of the PNA probes one or more of the peptide nucleic acid residues that are derivatized with the charged moieties are L-lysine peptide nucleic acid residues.

29. The set of claim 21, wherein in all of the PNA probes one or more of the peptide nucleic acid residues that are derivatized with the charged moieties are L-thialysine peptide nucleic acid residues.

30. The set of claim 21, wherein in all of the PNA probes one or more of the peptide nucleic acid residues that are derivatized with the charged moieties are L-lysine peptide nucleic acid residues.

31. The set of claim 21, wherein independently in one or more of the PNA probes one or more of the peptide nucleic acid residues that are derivatized with the short-chain oligoethylene moiety are derivatized with the short-chain oligoethylene moiety on the gamma carbon.

32. The set of claim 21, wherein in all of the PNA probes one or more of the peptide nucleic acid residues that are derivatized with the short-chain oligoethylene moiety are derivatized with the short-chain oligoethylene moiety on the gamma carbon.

33. The set of claim 21, wherein in one or more of the PNA probes one or more of the short-chain oligoethylene moieties are diethylene glycol.

34. The set of claim 21, wherein in all of the PNA probes one or more of the short-chain oligoethylene moieties are diethylene glycol.

35. The set of claim 21, wherein the capture tag is biotin or streptavidin.

36. The set of claim 21, wherein the PNA probes target (a) sequences in human genomic DNA located in the MHC region of chromosome 6; (b) sequences in human genomic DNA associated with one or more diseases or conditions or having a known correlation with development of one or more disease or conditions, wherein the diseases or conditions are selected from the group consisting of autoimmune diseases, diabetes, metabolic syndrome, and cancer; (c) sequences in human genomic DNA at different positions that map to a multiplicity of enhancer elements associated with disease risk for autoimmune diseases; (d) sequences in human genomic DNA at different positions that map to a multiplicity of enhancer elements associated with disease risk for diabetes and the metabolic syndrome; (e) sequences in human genomic DNA at different positions that map to a multiplicity of enhancer elements associated with the differentiation of different subsets of white blood cells; (f) sequences in human mitochondrial DNA; (g) sequences in dog mitochondrial DNA; or (h) sequences in genomic DNA of one or more parasites selected from the group consisting of bacteria, archaea, fungi, protozoa, or mixtures thereof.

37. The set of claim 21, wherein the PNA probes target sequences in genomic DNA of one or more parasites selected from the group consisting of bacteria, archaea, fungi, protozoa, or mixtures thereof, wherein the bacteria is one or more species of bacteria present in human oral cavity, human airway, human urogenital tract, human blood, or human feces.

38. A method of selectively enriching one or more nucleic acid fragments from a mixture of nucleic acid fragments, the method comprising:
(a) bringing into contact one or more sets of two or more PNA probes of claim 21 with a first nucleic acid sample to form a reaction mix;
(b) incubating the reaction mix under conditions that allow target-specific strand invasion binding by the PNA probes to their target sequence in a nucleic acid fragment, thereby forming nucleic acid fragments bound by invading PNA probes;
(c) capturing the nucleic acid fragments bound by PNA probes via the capture tag and removing the uncaptured components of the reaction mix from the captured nucleic acid fragments bound by PNA probes;
(d) eluting the captured nucleic acid fragments from the PNA probes to form an enriched nucleic acid sample, wherein nucleic acid fragments targeted by the PNA probes are enriched in the enriched nucleic acid sample as compared to the first nucleic acid sample.

39. The method of claim 38 wherein the reaction mix further comprises a single-strand binding protein.

40. The method of claim 38, wherein the first nucleic acid sample has high sequence complexity.

41. The method of claim 38, wherein the first nucleic acid sample includes double stranded DNA.

42. The method of claim 41, wherein the double stranded DNA has never been completely denatured or never been substantially denatured.

43. The method of claim 38, wherein the first nucleic acid sample includes genomic DNA.

44. The method of claim 38, wherein the enriched nucleic acid fragments have an average length of at least 2,000 base pairs.

45. The method of claim 38, wherein the enriched nucleic acid fragments have an average length of at least 10,000 base pairs.

46. The method of claim 38, wherein the enriched nucleic acid fragments have an average length of at least 15,000 base pairs.

47. The method of claim 38, wherein each of the enriched nucleic acid fragments has a length of at least 2,000 base pairs.

48. The method of claim 38, wherein the enriched nucleic acid sample comprises a molar ratio of targeted to non-targeted nucleic acid fragments that is between 50:1 and 150:1.

49. The method of claim 38 further comprising, following step (b) and prior to step (c), removing unbound PNA probes from the reaction mix.

50. The method of claim 38 further comprising, simultaneous with capturing the nucleic acid fragments bound by PNA probes, capturing unbound PNA probes via the capture tag.

51. The method of claim 38, wherein eluting the bound nucleic acid fragments in step (d) is carried out using Herculase II DNA polymerase.

52. The method of claim 38, wherein eluting the bound nucleic acid fragments in step (d) is carried out by de-protonation of the charged moiety by raising the pH.

53. The method of claim 38 further comprising amplifying one or more of the nucleic acid fragments in the enriched nucleic acid sample.

54. The method of claim 53, wherein substantially all of the nucleic acid fragments in the enriched nucleic acid sample are amplified.

55. The method of claim 53, wherein the nucleic acid fragments are amplified by whole genome amplification.

56. The method of claim 38, wherein the nucleic acid sample comprises ILLUMINA-MOLECULO® adapter-ligated nucleic acid fragments.

57. The method of claim 38, wherein the nucleic acid sample comprises nucleic acid fragments that have been end-repaired and purified according to one or more protocols for PACIFIC BIOSCIENCES® Library Preparation.

58. The method of claim 38, wherein the nucleic acid sample comprises PACBIO® hairpin adapter-ligated nucleic acid fragments.

59. The method of claim 38, further comprising, following step (c) and prior to step (d), ligating PACBIO® hairpin adapters to the captured nucleic acid.

60. A kit comprising
(a) the set of two or more PNA probes of claim 21; and
(b) instructions for performing a method, wherein the method comprises
(i) bringing into contact the set with a first nucleic acid sample to form a reaction mix;
(ii) incubating the reaction mix under conditions that allow target-specific strand invasion binding by the PNA probes to their target sequence in a nucleic acid fragment, thereby forming nucleic acid fragments bound by invading PNA probes;
(iii) capturing the nucleic acid fragments bound by PNA probes via the capture tag and removing the uncaptured components of the reaction mix from the captured nucleic acid fragments bound by PNA probes;
(iv) eluting the captured nucleic acid fragments from the PNA probes to form an enriched nucleic acid sample, wherein nucleic acid fragments targeted by the PNA probes are enriched in the enriched nucleic acid sample as compared to the first nucleic acid sample.

61. The kit of claim 60 further comprising one of more enzymes or proteins for performing one or more steps in the method.

62. A method of selectively enriching one or more nucleic acid fragments from a mixture of nucleic acid fragments, the method comprising:
(a) bringing into contact one or more sets of two or more peptide nucleic acid (PNA) hybridization probes with a first nucleic acid sample to form a reaction mix, wherein the PNA probes in the same set of two or more PNA probes are designed to target a different sequence in the same nucleic acid fragment, wherein the PNA probes in different sets of two or more PNA probes are designed to target different nucleic acid fragments, wherein the PNA probes each comprise one or more capture tags, wherein at least one of the PNA probes includes two or more peptide nucleic acid residues that are derivatized with a charged moiety on the alpha carbon, beta carbon, gamma carbon, or combinations thereof and one or more peptide nucleic acid residues that are derivatized with a neutral moiety on the alpha carbon, beta carbon, gamma carbon, or combinations thereof, and wherein there is an average of at or between 1.8 to 4.0 peptide nucleic acid residues that are not derivatized with a charged moiety between every peptide nucleic acid residue that is derivatized with a charged moiety;
(b) incubating the reaction mix under conditions that allow target-specific strand invasion binding by the PNA probes to their target sequence in a nucleic acid fragment, thereby forming nucleic acid fragments bound by invading PNA probes;
(c) capturing the nucleic acid fragments bound by PNA probes via the capture tag and removing the uncaptured components of the reaction mix from the captured nucleic acid fragments bound by PNA probes;
(d) eluting the captured nucleic acid fragments from the PNA probes to form an enriched nucleic acid sample, wherein nucleic acid fragments targeted by the PNA probes are enriched in the enriched nucleic acid sample as compared to the first nucleic acid sample.

63. The method of claim 62, wherein the PNA probes in at least one of the sets of two or more PNA probes have 18 or 19 peptide nucleic acid residues, wherein at or between three to five of the peptide nucleic acid residues of the PNA probes in the at least one of the sets of two or more PNA probes are derivatized with the charged moieties, wherein one or more of the peptide nucleic acid residues derivatized with charged moieties are selected from the group consisting of gamma-L-lysine PNA, gamma-L-thialysine PNA, and combinations thereof, wherein at or between two to six of the peptide nucleic acid residues of the PNA probes in the at least one of the sets of two or more PNA probes that are not derivatized with the charged moieties are derivatized with diethylene glycol, and wherein the capture tag of the PNA probes in at least one of the sets of two or more PNA probes is biotin.

64. The PNA probe of claim 1, wherein the probe comprises one or more peptide nucleic acid residues that are derivatized with a negatively charged moiety on the alpha, beta, or gamma carbon or combinations thereof.

65. The PNA probe of claim 64, wherein the negatively charged moiety is glutamic acid or derivatives and variants thereof.

66. The PNA probe of claim 1, wherein one or more of the peptide nucleic acid residues that are derivatized with the charged moieties are glutamic acid peptide nucleic acid residues.

67. The PNA probe of claim 1, wherein the probe comprises 18, 19, or 20 peptide nucleic acid residues.

68. The PNA probe of claim 67, wherein five or six of the peptide nucleic acid residues are derivatized with the charged moieties.

69. The PNA probe of claim 68, wherein one or more of the peptide nucleic acid residues derivatized with the charged moieties are selected from the group consisting of gamma-L-lysine PNA, gamma-L-thialysine PNA, and combinations thereof.

70. The PNA probe of claim 69, wherein one or more of the peptide nucleic acid residues that are derivatized with the charged moieties are glutamic acid peptide nucleic acid residues.

71. The PNA probe of claim 70, wherein at or between two to six of the peptide nucleic acid residues that are not derivatized with the charged moieties are derivatized with diethylene glycol, and wherein the capture tag is biotin.

72. The PNA probe of claim 1, wherein the probe comprises at or between 15 to 25 peptide nucleic acid residues.

73. The PNA probe of claim 1, wherein there is an average of at or between 0.8 to 2.0 peptide nucleic acid residues that are not derivatized with a moiety between every peptide nucleic acid residue that is derivatized with a moiety.

74. The PNA probe of claim 1, wherein at or between 31% to 50% of the peptide nucleic acid residues of the PNA probe are derivatized with a charged moiety or a neutral moiety.

75. The PNA probe of claim 1, wherein at or between 15% to 32% of the peptide nucleic acid residues of the PNA probe are derivatized with a charged moiety.

76. The set of claim 21, wherein all of the PNA probes are a PNA probe, wherein each PNA probe independently (a) comprises at or between 15 to 25 peptide nucleic acid residues, (b) is designed to target a sequence in a nucleic acid fragment, (c) comprises one or more peptide nucleic acid residues that are derivatized with a charged moiety on the alpha, beta, or gamma carbon or combinations thereof, and one or more peptide nucleic acid residues that are derivatized with a neutral moiety on the alpha, beta, or gamma carbon, or combinations thereof, and (d) comprises one or more capture tags.

77. The set of claim 21, wherein in one or more of the PNA probes there is an average of at or between 0.8 to 2.0 peptide nucleic acid residues that are not derivatized with a moiety between every peptide nucleic acid residue that is derivatized with a moiety.

78. The set of claim 21, wherein in one or more of the PNA probes at or between 31% to 50% of the peptide nucleic acid residues of the PNA probe are derivatized with a charged moiety or a neutral moiety.

79. The PNA probe of claim 1, wherein three, four, five, or six of the peptide nucleic acid residues are derivatized with the charged moieties on, independently for each of the peptide nucleic acid residues derivatized with a charged moiety, the alpha, beta, or gamma carbon.

* * * * *

UNITED STATES PATENT AND TRADEMARK OFFICE
CERTIFICATE OF CORRECTION

PATENT NO. : 11,046,999 B2  
APPLICATION NO. : 15/268403  
DATED : June 29, 2021  
INVENTOR(S) : Lizardi et al.

Page 1 of 1

It is certified that error appears in the above-identified patent and that said Letters Patent is hereby corrected as shown below:

In the Specification

Column 09, Line 34, replace "PNA molecule" with --PNA molecules--.
Column 13, Line 38, replace "Example" with --examples--.
Column 19, Line 4, replace "Thus, is this" with --Thus, in this--.
Column 19, Lines 32-38, replace "In some forms, the PNA probe includes one or more capture tags. In some forms, the PNA probe is designed to target a sequence in a nucleic acid. In some forms, the PNA probe includes one or more capture tags. In some forms, the PNA probe is designed to target a sequence in a nucleic acid fragment." with --In some forms, the PNA probe includes one or more capture tags. In some forms, the PNA probe is designed to target a sequence in a nucleic acid fragment. In some forms, the PNA probe includes one or more capture tags.--.
Column 25, Line 60, replace "target sequences" with --target sequence--.
Column 25, Lines 63-64, replace "A particularly" with --A particular--.
Column 25, Line 64, replace "target sequences" with --target sequence--.
Column 35, Line 57, replace "base paring" with --base pairing--.
Column 44, Line 61, replace "sequence" with --sequences--.
Column 57, Line 1, replace "or residues" with --residues--.
Column 67, Line 49, replace "zero or one residues" with --zero or one residue--.
Column 71, Line 32, replace "zero or one residues" with --zero or one residue--.
Column 72, Line 41, replace "zero or one residues" with --zero or one residue--.
Column 90, Line 25, replace "in the study phylogenetic" with --in studying phylogenetic--.
Column 96, Line 27, replace "PNA robes" with --PNA probes--.
Column 96, Line 40, replace "ds DNA" with --dsDNA--.
Column 106, Lines 31-32, replace "for kits for Kits" with --for kits--.

In the Claims

Claim 61, Column 143, Line 4, replace "one of more" with --one or more--.

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
tcccatgcac ttttcgatt                                                       19

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2 cttttacag cccgtctcac                                                       20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
tttatttggc gtttgtaatt                                                      20

<210> SEQ ID NO 4

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
tatccgtatt acttctctgg                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
caggtattcc tatcgtcctt                                              20

<210> SEQ ID NO 6
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 6
tgtgcctccc gttttgtcc                                               19

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 7
tgtccgattg ttcttatac                                               19

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 8
ctcggcatgt attttgctc                                               19

<210> SEQ ID NO 9
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 9
cacttgaccc tgctcgcct                                               19

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 10
```
cttcatctcg tctacaata                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
ctgcgttctt tgtactata                                                19

<210> SEQ ID NO 12
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 12
tctccgtatt tcctcgcta                                                19

<210> SEQ ID NO 13
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 13
atagtgtctc gtttactttt                                               19

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 14
ctgtaccaac ttctcaatc                                                19

<210> SEQ ID NO 15
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 15
cgctgactgt taccaccct                                                19

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 16
ctgattcacg ctctacatt                                                19

<210> SEQ ID NO 17
<211> LENGTH: 19
<212> TYPE: DNA

```
<213> ORGANISM: Artificial Sequence
<220> FEATURE:
<223> OTHER INFORMATION: Synthetic Oligonucleotide

<400> SEQUENCE: 17
tctcgtatat ttttcatgt                                              19

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
gttaactgtc cgtttttct                                              19

<210> SEQ ID NO 19
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 19
gttaaccgca cctctcttc                                              19

<210> SEQ ID NO 20
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 20
agtcgttctt ctatcatct                                              19

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 21
attacttttg ccgatgcct                                              19

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 22
acccatccct cttgcgact                                              19

<210> SEQ ID NO 23
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 23
ctacaactct accgctgct                                              19
```

```
<210> SEQ ID NO 24
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 24
ttactccgct tcttttcaa                                                19

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
ccattcaccg tccatacct                                                19

<210> SEQ ID NO 26
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 26
attccggttg tttctcgtt                                                19

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 27
tcctgacccg tttaatctt                                                19

<210> SEQ ID NO 28
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 28
ctttactctt atcccgtaa                                                19

<210> SEQ ID NO 29
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 29
acttgtcccg ttcaactcc                                                19

<210> SEQ ID NO 30
<211> LENGTH: 19
<212> TYPE: DNA
<213> ORGANISM: Artificial Sequence
<220> FEATURE:
```

```
<223> OTHER INFORMATION: Synthetic Oligonucleotide

<400> SEQUENCE: 30
gtccctatgc taaccctct                                                    19

<210> SEQ ID NO 31
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 31
acccgccaca tctaccatc                                                    19

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 32
cacgctactc ctacctatc                                                    19

<210> SEQ ID NO 33
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 33
ctcgctaacc tcgccttac                                                    19

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 34
acttactatc cgccatccc                                                    19
```